US012559867B2

(12) United States Patent
Ma et al.

(10) Patent No.: US 12,559,867 B2
(45) Date of Patent: Feb. 24, 2026

(54) FIBERS OF POLYMERS THAT HAVE A BACKBONE INCLUDING A POSITIVELY CHARGED COMPONENT OF A ZWITTERIONIC MOIETY, AND THEIR USE IN IMPLANTABLE THERAPEUTIC DELIVERY SYSTEMS

(71) Applicant: Cornell University, Ithaca, NY (US)

(72) Inventors: Minglin Ma, Ithaca, NY (US); Qingsheng Liu, Ithaca, NY (US); Xi Wang, Ithaca, NY (US); James A. Flanders, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 963 days.

(21) Appl. No.: 17/607,896

(22) PCT Filed: Apr. 30, 2020

(86) PCT No.: PCT/US2020/030798
§ 371 (c)(1),
(2) Date: Oct. 31, 2021

(87) PCT Pub. No.: WO2020/223525
PCT Pub. Date: Nov. 5, 2020

(65) Prior Publication Data

US 2022/0380944 A1 Dec. 1, 2022

Related U.S. Application Data

(60) Provisional application No. 62/840,827, filed on Apr. 30, 2019.

(51) Int. Cl.
*D01F 6/70* (2006.01)
*A61L 17/00* (2006.01)
(Continued)

(52) U.S. Cl.
CPC .............. *D01F 6/70* (2013.01); *A61L 17/005* (2013.01); *A61L 17/10* (2013.01); *A61L 17/145* (2013.01);
(Continued)

(58) Field of Classification Search
None
See application file for complete search history.

(56) References Cited

U.S. PATENT DOCUMENTS 5,534,404 A 7/1996 Laurance et al.
8,308,699 B2 11/2012 Zhang et al.
(Continued)

FOREIGN PATENT DOCUMENTS

CN 103724595 B 10/2015
CN 104031236 B 6/2016
WO WO-2019071135 A1 * 4/2019 ............ A61F 2/022

OTHER PUBLICATIONS

ThermoFisher.www.thermofisher.com/order/catalog/product/183215000?gclid=&EAlalQobChMl5oGUyeGjiwMVzVZHAR2JliDpEAQYAyABEgK7ovD_BwE&source=google_shopping&ISO_CODE=us&LANG_CODE=en&ef_id=EAlalQobChMI50GUyeGjiwMVzVZHAR2JliDpEAQYAyABEgK7ovD_BwE:G:s&s_kwcid=AL!3652!3 !!!!x !!!21671814368!&gad_source=1. Published: 2025.*
(Continued)

*Primary Examiner* — Nicole P Babson
*Assistant Examiner* — Lori K Mattison
(74) *Attorney, Agent, or Firm* — Troutman Pepper Locke LLP (Rochester)

(57) ABSTRACT

The present application relates to fibers having a diameter of 1 nm to 10,000 nm, of one or more biocompatible polymers, wherein the polymers have a backbone which includes a positively charged component from a zwitterionic moiety.
(Continued)

Additionally, this application discloses an implantable therapeutic delivery system and its method of formation, comprising a housing defining a chamber, wherein said housing is porous and formed from the fibers. Inside of the housing includes a preparation of cells which release a therapeutic agent from the chamber. The implantable therapeutic delivery system can be used in the treatment of diabetes.

15 Claims, 25 Drawing Sheets

(51) Int. Cl.

| | |
|---|---|
| ***A61L 17/10*** | (2006.01) |
| ***A61L 17/14*** | (2006.01) |
| ***A61L 27/18*** | (2006.01) |
| ***A61L 27/52*** | (2006.01) |
| ***A61L 27/54*** | (2006.01) |
| ***A61L 27/56*** | (2006.01) |
| ***D01F 6/80*** | (2006.01) |

(52) U.S. Cl.
CPC ............... *A61L 27/18* (2013.01); *A61L 27/52* (2013.01); *A61L 27/54* (2013.01); *A61L 27/56* (2013.01); *D01F 6/80* (2013.01)

(56) References Cited

U.S. PATENT DOCUMENTS

| | | | |
|---|---|---|---|
| 9,598,544 | B2 | 3/2017 | Jiang et al. |
| 9,808,560 | B2 | 11/2017 | Hong et al. |
| 10,189,944 | B2 | 1/2019 | Minagawa |
| 10,272,180 | B2 | 4/2019 | Jiang et al. |
| 10,493,107 | B2 | 12/2019 | Ma et al. |
| 11,903,976 | B2 | 2/2024 | Ma et al. |
| 2005/0002981 | A1 | 1/2005 | Lahtinen et al. |
| 2014/0024768 | A1 | 1/2014 | Coneski et al. |
| 2014/0248232 | A1 | 9/2014 | Hong et al. |
| 2017/0108492 | A1 | 4/2017 | Jiang et al. |
| 2019/0191703 | A1 | 6/2019 | Day et al. |
| 2019/0389979 | A1 | 12/2019 | Ma et al. |
| 2021/0002493 | A1 | 1/2021 | Lawin et al. |
| 2021/0163657 | A1 | 6/2021 | Cheng et al. |

OTHER PUBLICATIONS

Hong. Biomaterials 30 (2009) 2457-2467.*
International Preliminary Report on Patentability for corresponding Application No. PCT/US2020/030798 (Nov. 2, 2021).
International Search Report and Written Opinion for PCT/US2020/030798 (Jul. 29, 2020).
Ma et al., “Preparation of Polyurethane with Zwitterionic Side Chains and Their Protein Resistance,” ACS Appl. Mater. Interfaces 3(2):455-461 (2011).
English Translation of First Office Action for Chinese Application No. 202080048213.5 (Dated Jun. 20, 2024).
International Search Report and Written Opinion for PCT/US2020/030798, dated Jul. 29, 2020.
Lalani and Liu, “Electrospun Zwitterionic Poly(Sulfobetaine Methacrylate) for Nonadherent, Superabsorbent, and Antimicrobial Wound Dressing Applications,” Biomacromolecules, 13:1853-1863 (2012).
Wang, et al., “Zwitterionic Polyurethanes with Tunable Surface and Bulk Properties,” ACS Applied Materials & Interfaces, 10:37609-37617 (2018).
Ye, et al., “Nonthrombogenic Biodegradable Elastomeric Polyurethanes with Variable Sulfobetaine Content,” ACS Applied Materials & Interfaces, 6:22796-22809 (2014).
An et al., “Developing Robust, Hydrogel-Based, Nanofiber-Enabled Encapsulation Devices (NEEDs) for Cell Therapies,” Biomaterials 37(23):40-48 (2014).
Extended European Search Report for corresponding Application No. 20798349.5 (Jun. 22, 2023).

* cited by examiner

FIBERS OF POLYMERS THAT HAVE A BACKBONE INCLUDING A POSITIVELY CHARGED COMPONENT OF A ZWITTERIONIC MOIETY, AND THEIR USE IN IMPLANTABLE THERAPEUTIC DELIVERY SYSTEMS

This application is a national stage application under 35 U.S.C. § 371 of PCT Application No. PCT/US2020/030798, filed Apr. 30, 2020, which claims the priority benefit of U.S. Provisional Patent Application Ser. No. 62/840,827, filed Apr. 30, 2019, which is hereby incorporated by reference in its entirety.

This invention was made with government support under grant number 1R01DK105967-01A1 awarded by the National Institutes of Health. The government has certain rights in the invention.

FIELD

The present application relates to fibers of polymers that have a backbone including a positively charged component of a zwitterionic moiety, and their use in implantable therapeutic delivery systems.

BACKGROUND

Type 1 diabetes (T1D) affects millions of people worldwide. It is an autoimmune disease in which insulin-producing pancreatic β-cells are mistakenly destroyed by the body's immune system (Atkinson et al., "Type 1 Diabetes," *The Lancet* 383(9911):69-82 (2014); Katsarou et al., "Type 1 Diabetes Mellitus," *Nature Reviews Disease Primers* 3(1):1-17 (2017)). Despite decades of advancement in chemical modifications and dosing strategies, insulin remains an imperfect and painful therapy. Transplantation of donor islets has shown promise in some patients (Desai and Shea, "Advances in Islet Encapsulation Technologies," *Nature Reviews Drug Discovery* 16(5):338-350 (2017); Yu et al., "Glucose-responsive Insulin Patch for the Regulation of Blood Glucose in Mice and Minipigs," *Nature Biomedical Engineering* 1-8 (2020); Facklam et al., "Biomaterials for Personalized Cell Therapy," *Advanced Materials* 1902005 (2019); Weaver et al., "Design of a Vascularized Synthetic Poly (Ethylene Glycol) Macroencapsulation Device for Islet Transplantation," *Biomaterials* 172:54-65 (2018); Mahou et al., "Injectable and Inherently Vascularizing Semi-interpenetrating Polymer Network for Delivering Cells to the Subcutaneous Space," *Biomaterials* 131:27-35 (2017); Orive et al., "Cell Encapsulation: Promise and Progress," *Nature Medicine* 9(1):104-107 (2003): Pedraza et al., "Preventing Hypoxia-induced Cell Death in Beta Cells and Islets Via Hydrolytically Activated, Oxygen-generating Biomaterials," *Proceedings of the National Academy of Sciences* 109(11):4245-4250 (2012); Yang and Cao, "Glucose-responsive Insulin Release: Analysis of Mechanisms, Formulations, and Evaluation Criteria," *Journal of Controlled Release* 263:231-239 (2017)), but broad application for larger T1D population has been hampered because of shortage of donor islets and the need for long-term immunosuppression to prevent immune rejection. Recently, the development of human embryonic stem cell (hESC)-derived islet technique has the potential to provide an unlimited supply of β-cells for transplantation (Pagliuca et al., "Generation of Functional Human Pancreatic β Cells In Vitro," *Cell* 159(2):428-439 (2014); Hogrebe et al., "Targeting the Cytoskeleton to Direct Pancreatic Differentiation of Human Pluripotent Stem Cells," *Nature Biotechnology* 1-11 (2020)). However, teratoma formation is a risk and safety concern in transplantation. Hence, there is an urgent need for an immunoprotective encapsulation device that is both safe, allowing no cell escape/penetration or device breakage, and functional, supporting long-term cell function with low foreign body response and high mass diffusion.

Currently, there are two major types of encapsulation device: microscopic and macroscopic devices (Ernst et al., "Islet Encapsulation," *Journal of Materials Chemistry B* 6(42):6705-6722 (2018)). For microscopic devices, alginate microcapsules likely represent the most studied islet encapsulation platform (Veiseh et al., "Size- and Shape-dependent Foreign Body Immune Response to Materials Implanted in Rodents and Non-human Primates," *Nature Materials* 14(6): 643-651 (2015); Calafiore and Basta, "Clinical Application of Microencapsulated Islets: Actual Prospectives on Progress and Challenges," *Advanced Drug Delivery Reviews* 67:84-92 (2014)). Microencapsulation with a large surface area can provide ample mass transfer to maintain survival and function of sufficient islets. However, microscopic device is limited in the full graft retrieval, posing safety concerns and risks for clinical applications. Macroscopic devices such as long fibers, thin sheets, and diffusion chambers have been developed as alternative strategy for islet transportation (An et al., "Designing a Retrievable and Scalable Cell Encapsulation Device for Potential Treatment of Type 1 Diabetes," *Proceedings of the National Academy of Sciences* 115(2):E263-E272 (2018); Ludwig et al., "Transplantation of Human Islets Without Immunosuppression," *Proceedings of the National Academy of Sciences* 110(47):19054-19058 (2013); Bose et al., "A Retrievable Implant for the Long-term Encapsulation and Survival of Therapeutic Xenogeneic Cells," *Nature Biomedical Engineering* 1-13 (2020)). Although hydrogel-based macroscopic devices such as alginate and polyethylene glycol (PEG) are acknowledged to have biocompatibility and high diffusion rates (Mahou et al., "Injectable and Inherently Vascularizing Semi-interpenetrating Polymer Network for Delivering Cells to the Subcutaneous Space," *Biomaterials* 131:27-35 (2017); An et al., "Designing a Retrievable and Scalable Cell Encapsulation Device for Potential Treatment of Type 1 Diabetes," *Proceedings of the National Academy of Sciences* 115(2):E263-E272 (2018); Zhang et al., "Rapid and Long-Term Glycemic Regulation with a Balanced Charged Immune-Evasive Hydrogel in T1DM Mice," *Advanced Functional Materials* 29(19):1900140 (2019)), they tend to have relatively low mechanical strength. Moreover, this intrinsic softness of hydrogels is prone to cell entrance and escape. Some hydrophobic macroscopic devices made of hydrophobic polytetrafluoroethylene (PTFE) or polycaprolactone (PCL) were mechanically robust and were considered to prevent cell escape to some extent (Neufeld et al., "The Efficacy of an Immunoisolating Membrane System for Islet Xenotransplantation in Minipigs," *PloS one* 8(8) (2013); Ludwig et al., "Favorable Outcome of Experimental Islet Xenotransplantation Without Immunosuppression in a Nonhuman Primate Model of Diabetes," *Proceedings of the National Academy of Sciences* 114(44):11745-11750 (2017); Nyitray et al., "Polycaprolactone Thin-film Micro- and Nanoporous Cell-encapsulation Devices," *ACS Nano* 9(6):5675-5682 (2015)). However, fibrotic growth around devices is a critical issue as they prevent mass delivery across device and makes device retrieval difficult.

Polyurethane (PU), one important kind of biomaterial, has been applied for islet encapsulation previously, but PU has diffusion constraints because of its hydrophobic nature (i.e. glucose and insulin to and from the islets) (Ward et al., "Development of a Hybrid Artificial Pancreas With a Dense Polyurethane Membrane, *ASAIO Journal (American Society for Artificial Internal Organs:* 1992) 39(3):M261-7 (1993); Zondervan et al., "Design of a Polyurethane Membrane for the Encapsulation of Islets of Langerhans," *Biomaterials* 13(3):136-144 (1992)). Zwitterionic polymers have gained increasing attention recently for cell encapsulation owing to their superhydrophilic nature and exceptional biocompatibility (Chien et al., "Direct Cell Encapsulation in Biodegradable and Functionalizable Carboxybetaine Hydrogels," *Biomaterials* 33(23):5706-5712 (2012); Bai et al., "Expansion of Primitive Human Hematopoietic Stem Cells by Culture in a Zwitterionic Hydrogel," *Nature Medicine* 25(10):1566-1575 (2019); Dong et al., "In situ "Clickable" Zwitterionic Starch-based Hydrogel for 3D Cell Encapsulation," *ACS Applied Materials & Interfaces* 8(7):4442-4455 (2016)). It was previously reported that zwitterionically modified alginate and triazole-zwitterionic hydrogels mitigated the fibrotic deposition effectively and were applied for islet encapsulation (Liu et al., "Developing Mechanically Robust, Triazole-zwitterionic Hydrogels to Mitigate Foreign Body Response (FBR) for Islet Encapsulation," *Biomaterials* 230:119640 (2020); Liu et al., "Zwitterionically Modified Alginates Mitigate Cellular Overgrowth for Cell Encapsulation," *Nature Communications* 10(1):1-14 (2019)). Nevertheless, the low mechanical strength of hydrogel materials severely limits their practical uses.

The present application is directed to overcoming these and other deficiencies in the art.

SUMMARY

A first aspect of the present application relates to a fiber having a diameter of 1 nm to 10,000 nm, of one or more biocompatible polymers, where the polymers have a backbone including a positively charged component of a zwitterionic moiety.

A second aspect of the present application relates to an implantable therapeutic delivery system including a housing defining a chamber. The housing is porous and formed from the fibers having a diameter of 1 nm to 10,000 nm, of one or more biocompatible polymers, where the polymers have a backbone including a positively charged component of a zwitterionic moiety.

Another aspect of the present application relates to a method of preparing an implantable therapeutic delivery system. The method includes providing the fiber having a diameter of 1 nm to 10,000 nm, of one or more biocompatible polymers, where the polymers have a backbone including a positively charged component of a zwitterionic moiety. Then the fiber is applied around a form to create an elongate porous tube. The elongate porous tube is then removed from the form to produce an elongate hollow porous tube defining a chamber within it and extending between first and second open ends. This is followed by sealing the first end of the elongate hollow porous tube to close the first end, with the second end being left open. A hydrogel is then inserted into the chamber through the open second end. The hydrogel is then crosslinked to the fibers of the elongate hollow porous tube, and the second end of the elongate hollow porous tube is sealed.

A further aspect of the present application relates to a method of treating diabetes including selecting a subject having diabetes and implanting the implantable therapeutic delivery system of the present application, containing islet cells within the chamber, into the selected subject.

Another aspect of the present application relates to a method of delivering a therapeutic agent to a subject. The method includes implanting the implantable therapeutic delivery system of the present application, containing cells within the chamber, into a subject.

Yet another aspect of the present application relates to a zwitterionic sulfobetaine-based nylon polymer of formula (II)

(II)

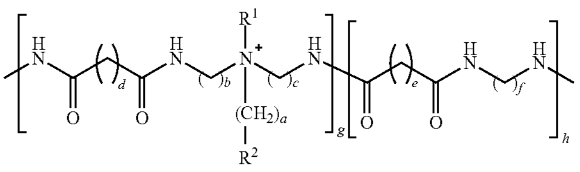

where $R^1$ is a $C_{1-10}$ alkyl;

$R^2$ is $SO_3^-$, $CO_2^-$, phosphate, or

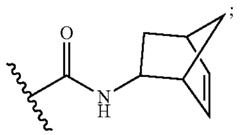 [SMILES: *C(=O)NC1CC2C=CC1C2]

a, b, c, d, e, and f are independently selected integers from 1 to 20;

g and h are integers from 1 to 10,000,000; and

indicates a point of attachment.

A final aspect of the present application relates to a zwitterionic sulfobetaine-based polydimethylsiloxane polymer of formula (III)

(III)

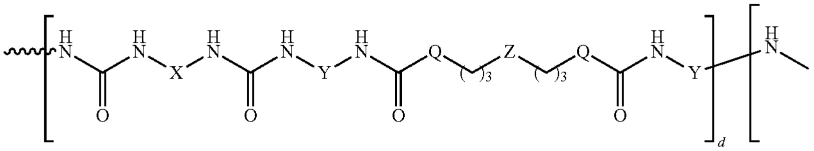

-continued

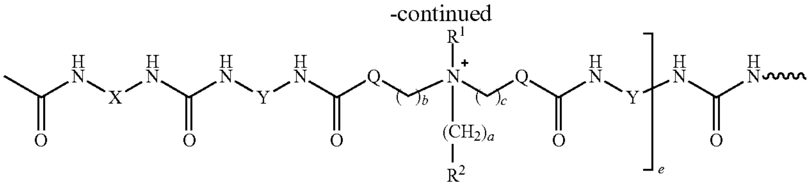

where

X and Y are independently selected from a substituted or unsubstituted $C_{1-20}$ alkylene;

Q is O or NH;

Z is a polydimethylsiloxane;

$R^1$ is H, or $C_{1-10}$ alkyl;

$R^2$ is $SO_3^-$, $CO_2^-$, or phosphate;

a, b, and c are independently selected integers from 1 to 20; and d and e are independently integers from 1 to 10,000,000.

It has been found by applicants that an encapsulation device made of a zwitterionic polyurethane polymer is useful for islet encapsulation in a therapeutic. The zwitterionic part of the polymer contributes to the improvement of hydrophilicity, mass delivery, antifouling property, and biocompatibility of the polyurethane. The polyurethane backbone ensures mechanical robustness. To date, the research on zwitterionic polyurethanes has been very limited and mainly focus on in vitro studies (Wang et al., "Zwitterionic Polyurethanes with Tunable Surface and Bulk Properties," *ACS Applied Materials & Interfaces* 10(43):37609-37617 (2018); Chen et al., "Development of Zwitterionic Polyurethanes With Multi-shape Memory Effects and Self-healing Properties," *Journal of Materials Chemistry A* 3(6):2924-2933 (2015); Hong et al., "Synthesis, Characterization, and Paclitaxel Release From a Biodegradable, Elastomeric, Poly (Ester Urethane) Urea Bearing Phosphorylcholine Groups for Reduced Thrombogenicity," *Biomacromolecules* 13(11): 3686-3694 (2012)).

A family of zwitterionic polyurethane (ZPU) polymers were developed where the mechanical properties, hydrophilicity, antifouling properties, and biocompatibility of the resulting polymer were finely tuned by adjusting the zwitterionic sulfobetaine (SB) content employed in the synthesis. The ZPU polymer was electrospun to fabricate a nanofibrous encapsulation device that integrates various attractive properties for islet transportation. Firstly, the ZPU nanofibrous membrane as a device wall was hydrophilic as opposed to conventional PU devices. Water drop and in vitro glucose-stimulated insulin secretion tests confirmed that this thick and hydrophilic wall allowed adequate mass delivery. Meanwhile, the ZPU membrane could maintain mechanically robust with breaking strain of >1.5 and tensile stress of >10 MPa. Secondly, the ZPU membrane exhibit excellent antifouling performance (i.e. low non-specific protein or cell attachment and macrophage activation). Additionally, ZPU device was capable of preventing cell entrance and escape in which electrospun fiber size was less than 281 nm. More importantly, the ZPU device induced minimal cellular deposition, less than ~10 μm reproducibly, in intraperitoneal space of immunocompetent mice with different implantation time points up to 6 months, while the thickness of cellular deposition on the PU device were 3-fold higher relative to ZPU device. Lastly, it was demonstrated that the ZPU device was safe, biocompatible, and functional long-term, enabling diabetes correction for up to 3 months in chemically induced diabetic C57BL/6 mice using encapsulated rat islets. The ZPU devices of the present application represent a promising candidate for the development of cell encapsulation therapies for T1D.

BRIEF DESCRIPTION OF THE DRAWINGS

FIG. 2A is the chemical structures of an exemplary the ZPU polymer of the present application. FIG. 2B is a schematic illustration of a ZPU device encapsulating islets. FIG. 2C shows the electrospun ZPU devices with various dimensions. FIG. 2D is a scanning electron micrograph of an electrospun ZPU device. FIG. 2E is the XPS spectra of the PU and ZPU-2 devices. FIG. 2F is the N1s XPS spectra of the PU and ZPU-2 devices. FIG. 2G is the FT-IR spectra of the PU and ZPU-2 devices. FIG. 2H is a plot of the tensile test (stress-strain curves) of the various ZPU devices. FIG. 2I are images of the water drop test on the ZPU and PU devices. FIG. 2J shows the H&E staining images of retrieved ZPU-2 and ZPU-3 devices 1 month post intraperitoneal implantation in C57BL/6J mice (n=4).

FIG. 3A depicts fluorescent images showing the adsorption of FITC labeled fibrinogen on the surfaces of the PU and ZPU films quantified by ImageJ, along with a graphical representation. FIG. 3B is the fluorescent microscopic images of NIH/3T3 cells after 3-days of culturing on TCPS, PU, and ZPU films, along with graphical representation. FIG. 3C is a graph showing the quantification of TNF-α secretion from macrophages cultured on different surfaces. Mean±SEM; n=6: *P<0.05. FIG. 3D is a graph of the in vitro GSIS of the encapsulated rat islets in the ZPU device, compared to that of free islets after 1 day culture, mean±SEM (n=4).

FIG. 4A is SEM images of ZPU devices made from different polymer concentrations (from left to right: 10%, 15%, and 20%). FIG. 4B is a plot of the fiber sizes as a function of concentration of ZPU polymer when electrospinning. FIG. 4C shows the H&E staining images of the retrieved ZPU devices (from left to right: 10%, 15%, and 20% ZPU) 1 month post intraperitoneal implantation in C57BL/6J mice (n=3-4). FIG. 4D is a graph of the quantification of cell penetration for the various ZPU devices.

FIG. 5A is representative H&E staining images of blank PU and ZPU devices at different implantation time points. FIG. 5B is a graph showing the analysis of the thickness of cellular overgrowth around the devices measured from H&E staining images, mean±SEM (n=3-4)

FIG. 6A is a plot of the blood glucose concentrations of non-fasting mice (n=17). FIG. 6B is a plot of the intraperitoneal glucose tolerance test (IPGTT) before retrieval on day 60 (n=4 per group). FIG. 6C is a plot of the ex vivo GSIS of the retrieved rat islets from ZPU on day 60, n=3, Mean±SEM, *P<0.05. FIG. 6D is a plot of the IPGTT before retrieval (n=3 per group) on day 90. FIG. 6E is a plot of the ex vivo GSIS of the retrieved rat islets from ZPU on day 90, n=3, Mean±SEM, *P<0.05. FIG. 6F is a plot of the measurement of total insulin content of the pancreas in different groups on day 60. (n=4-5). FIG. 6G is a bright field image of encapsulated rat islets after retrieval on day 60. Scale bar, 500 μm. FIG. 6H is a H&E stained cross-sectional image of retrieved islet-containing ZPU device after peeling off the membrane on day 60. Scale bar, 1000 μm. FIG. 6I is an H&E stained cross-sectional image of retrieved islet-containing ZPU device on day 60. Scale bar, 100 μm. FIG. 6J is an immunohistochemical staining of rat islets in a retrieved ZPU device on day 60 (Scale bar: 50 μm). FIG. 6K is an H&E stained cross-sectional image of retrieved islet-containing ZPU device on day 90. Scale bar, 200 μm. FIG. 6L is an image of immunohistochemical staining of rat islets in a retrieved ZPU device on day 90 (Scale bar: 50 μm).

DETAILED DESCRIPTION

Figure 1A:
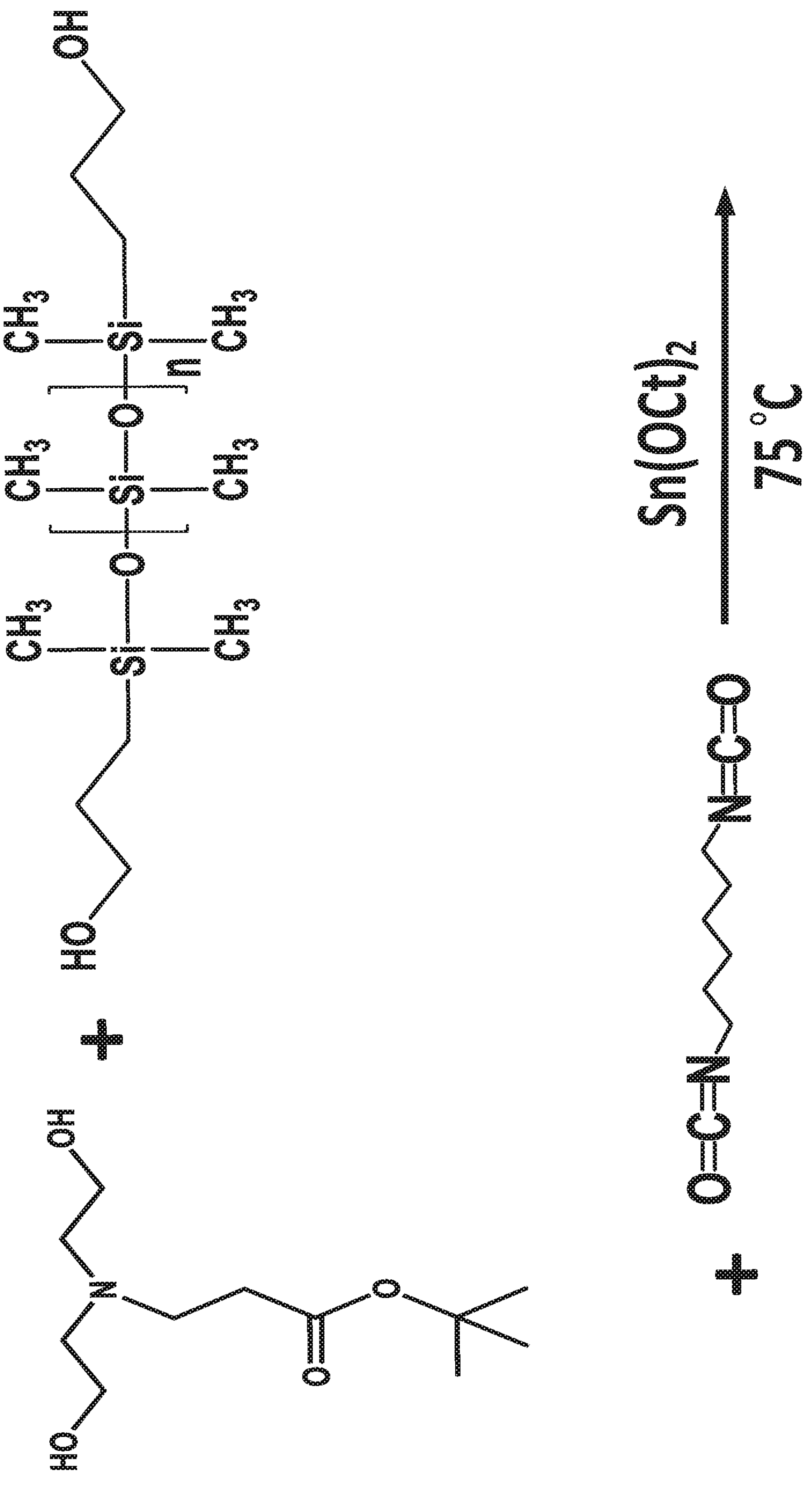
FIGS. 1A-1D are reaction schemes for the formation of the polydimethylsiloxane variants of the polymers of the present application.
Figure 1A:
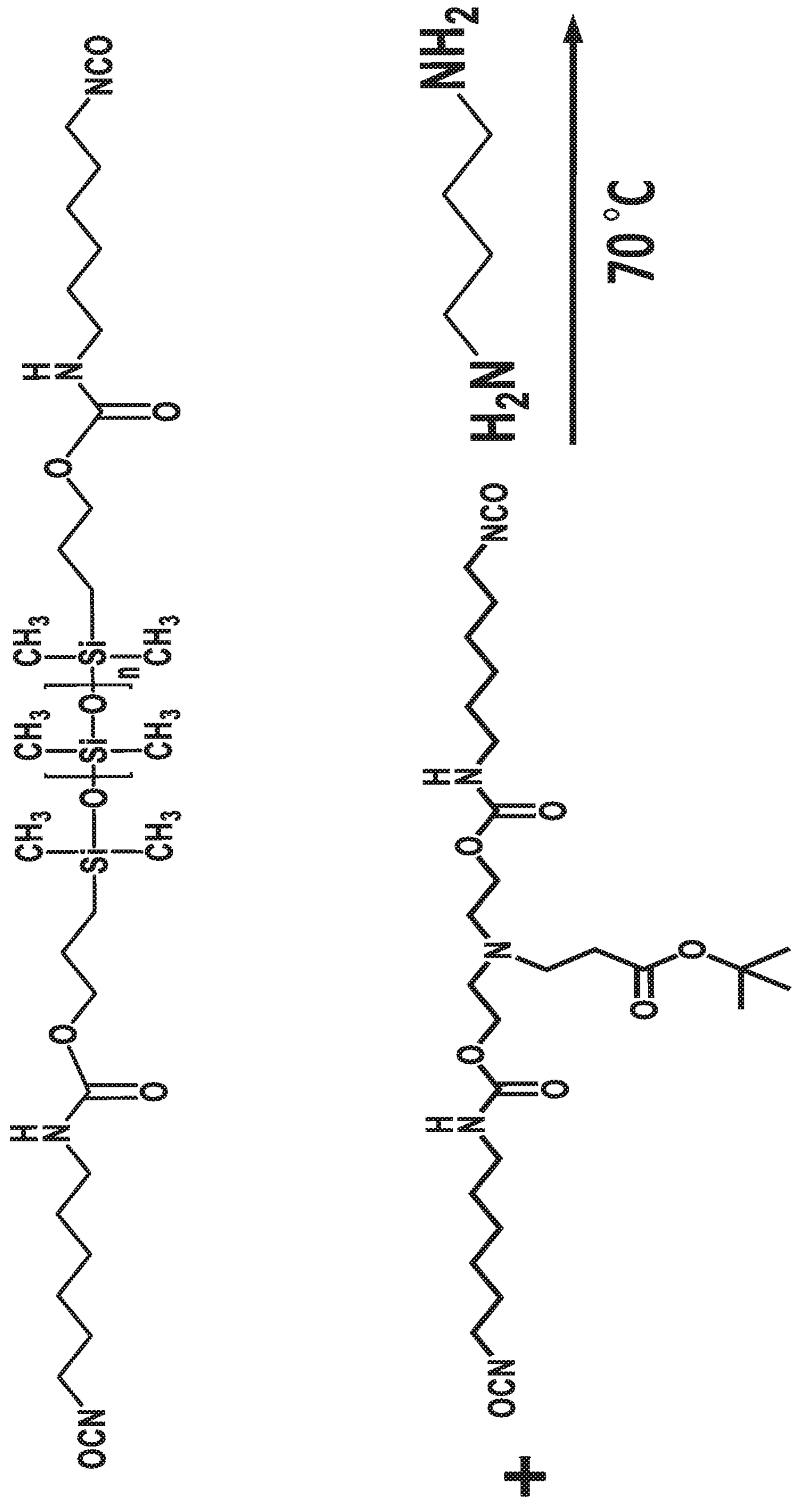
Figure 1A:
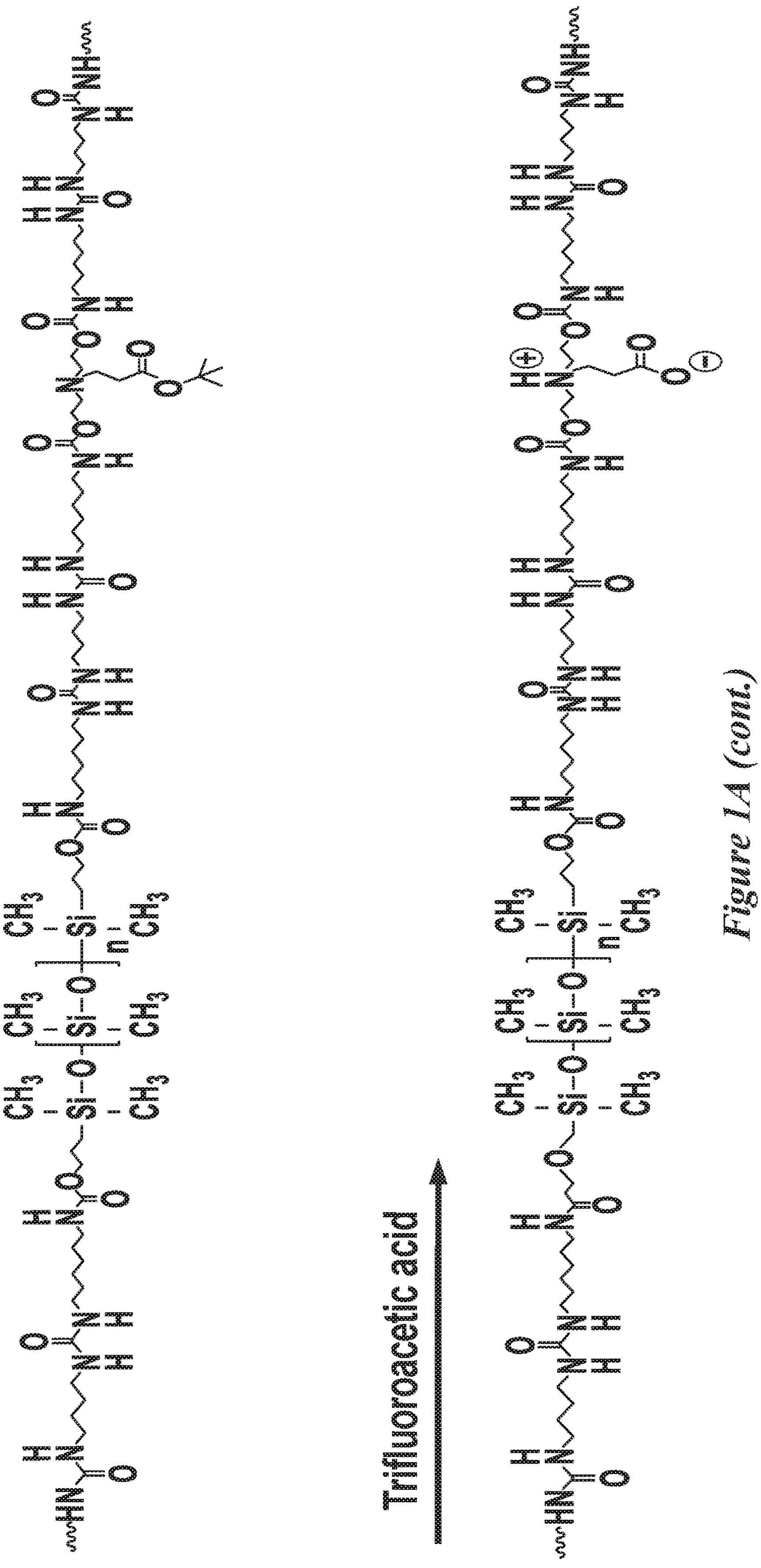
Figure 1B:
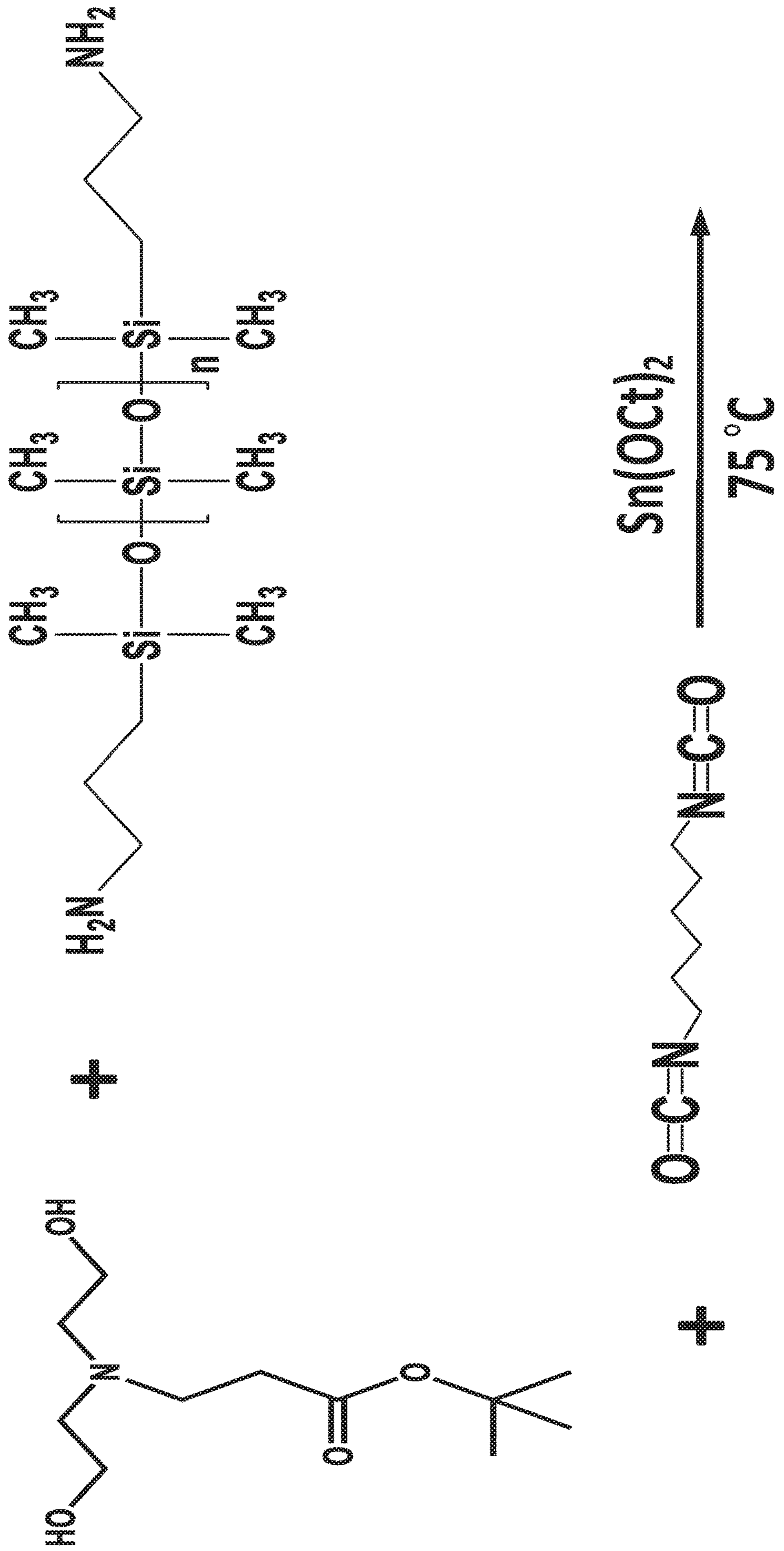
Figure 1B:
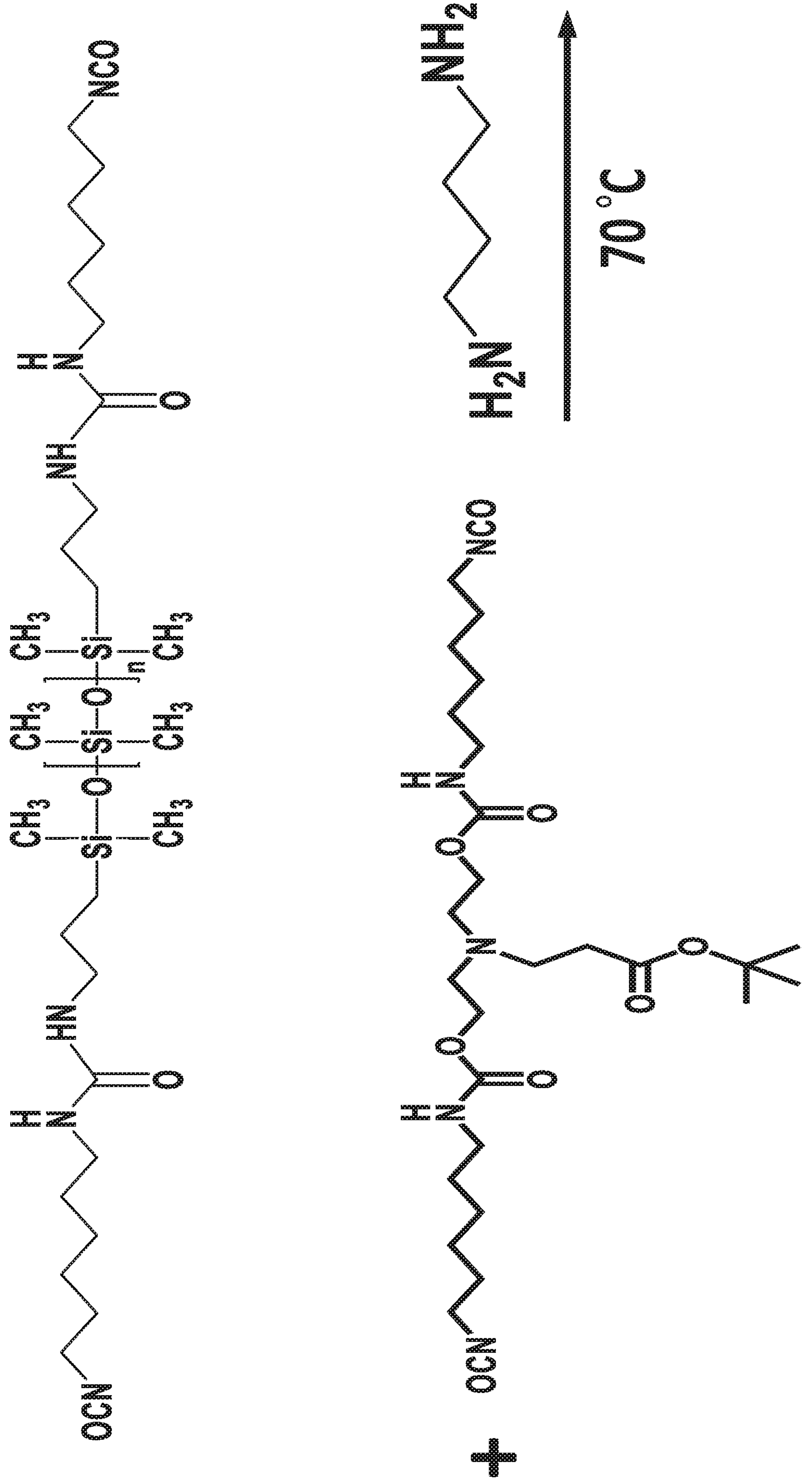
Figure 1B:
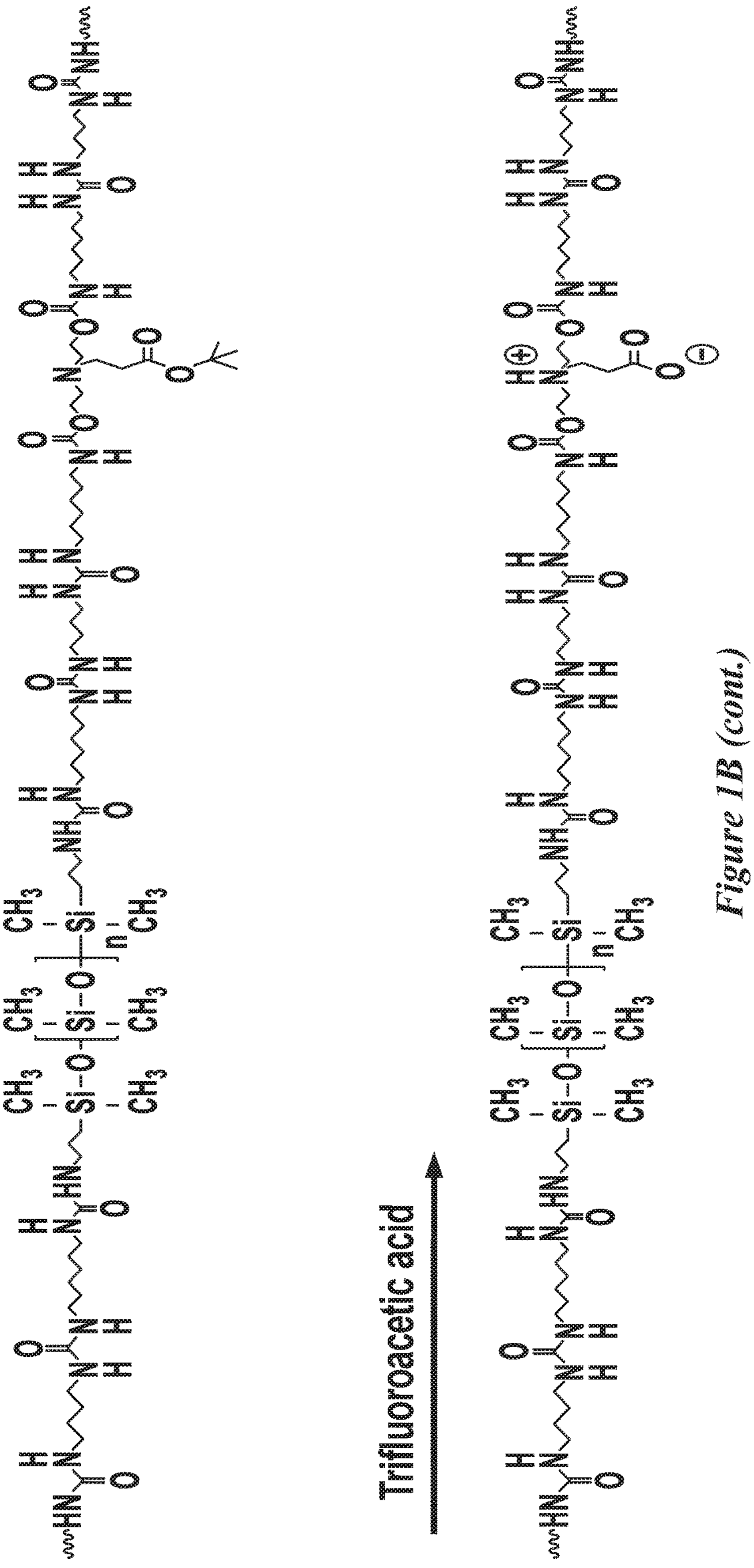
Figure 1C:
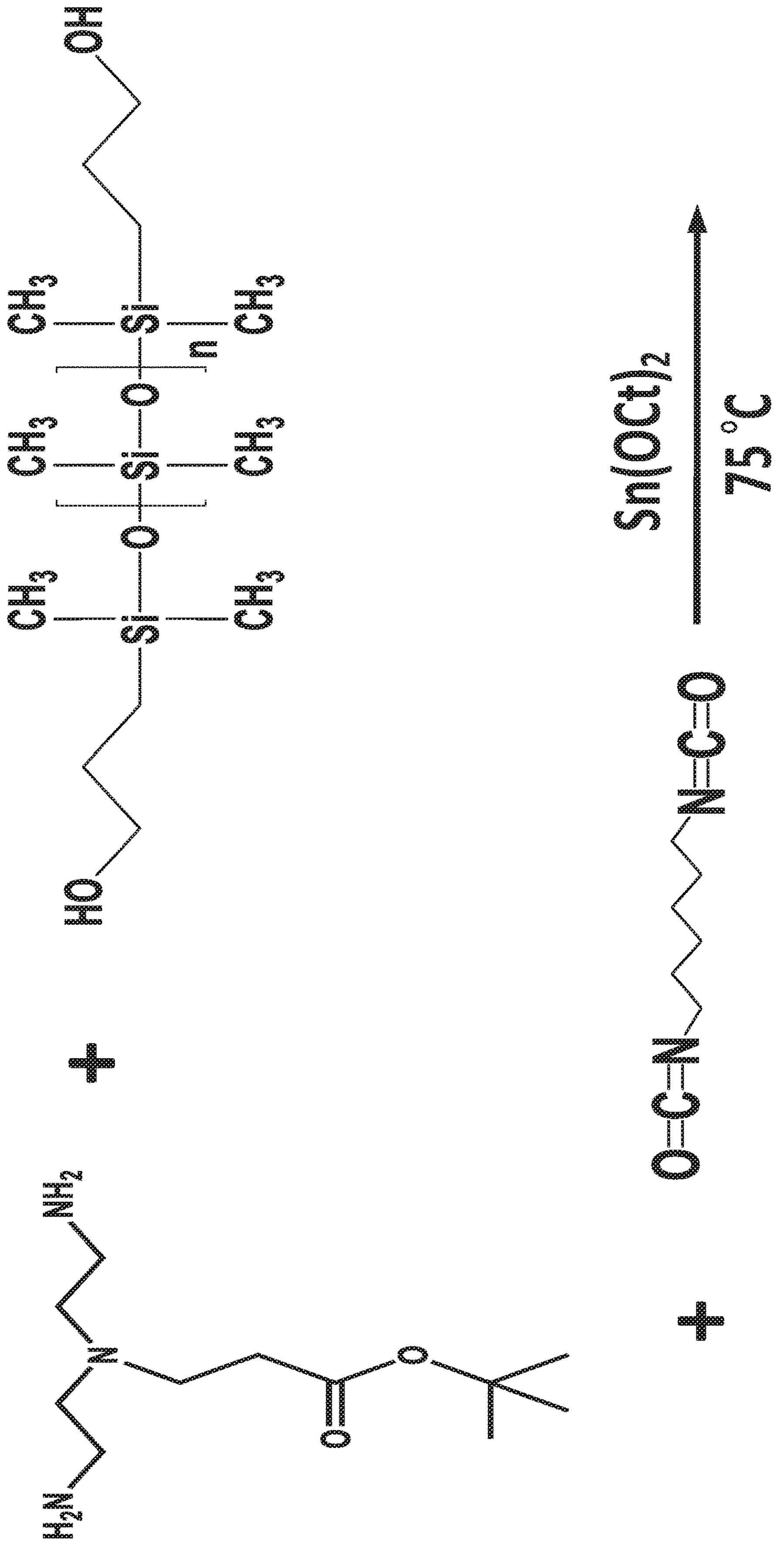
Figure 1C:
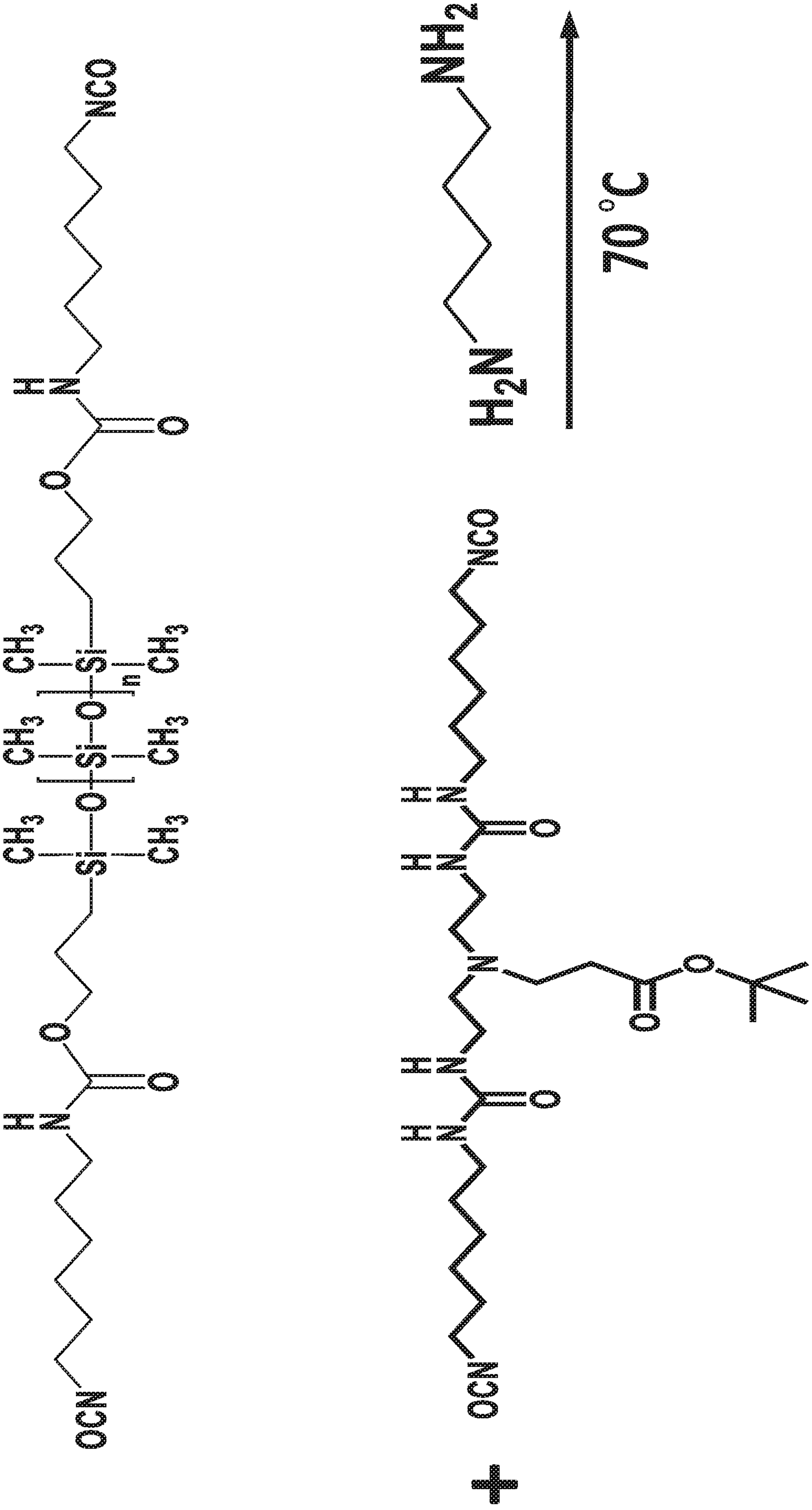
Figure 1C:
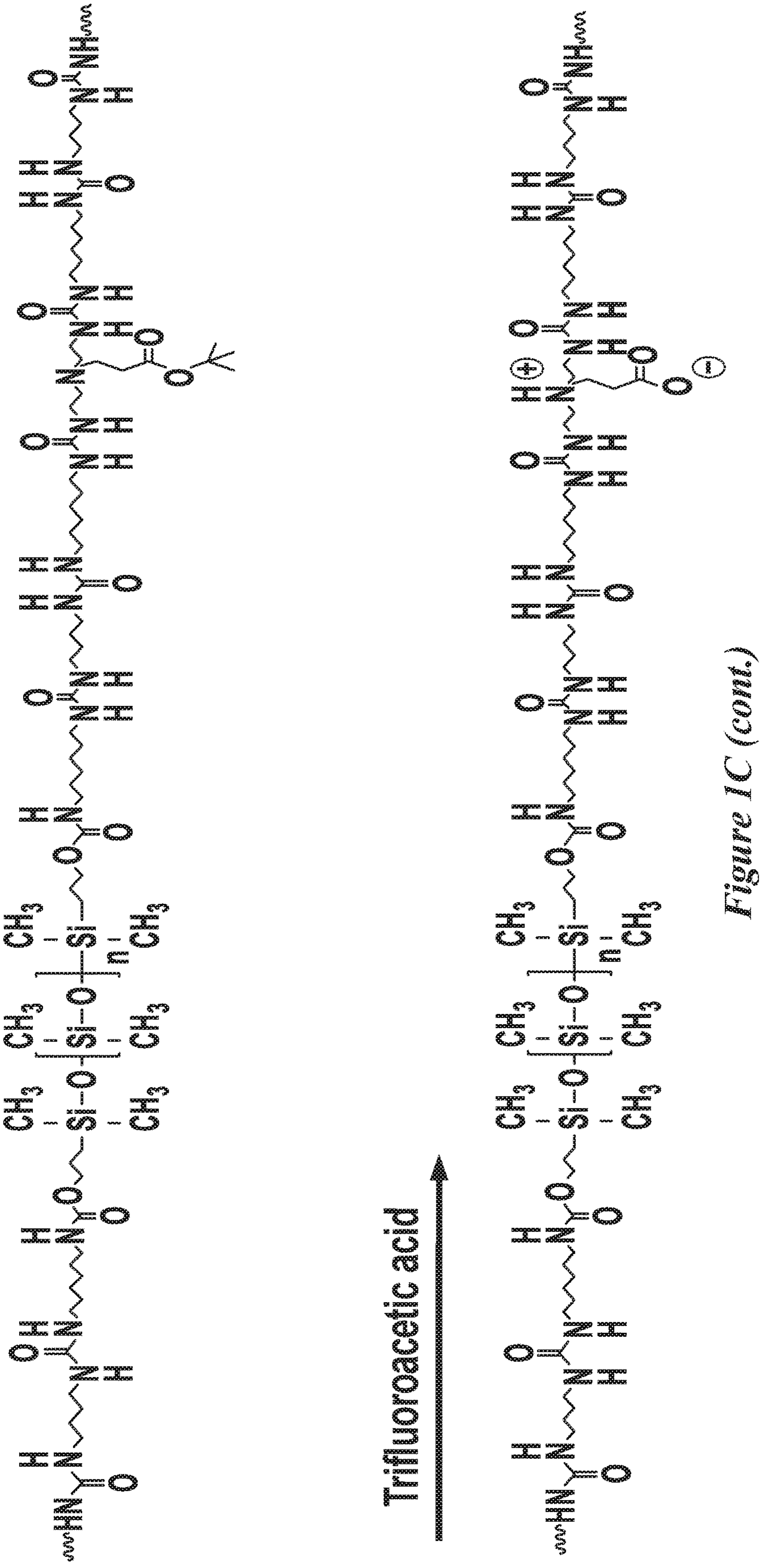
Figure 1D:
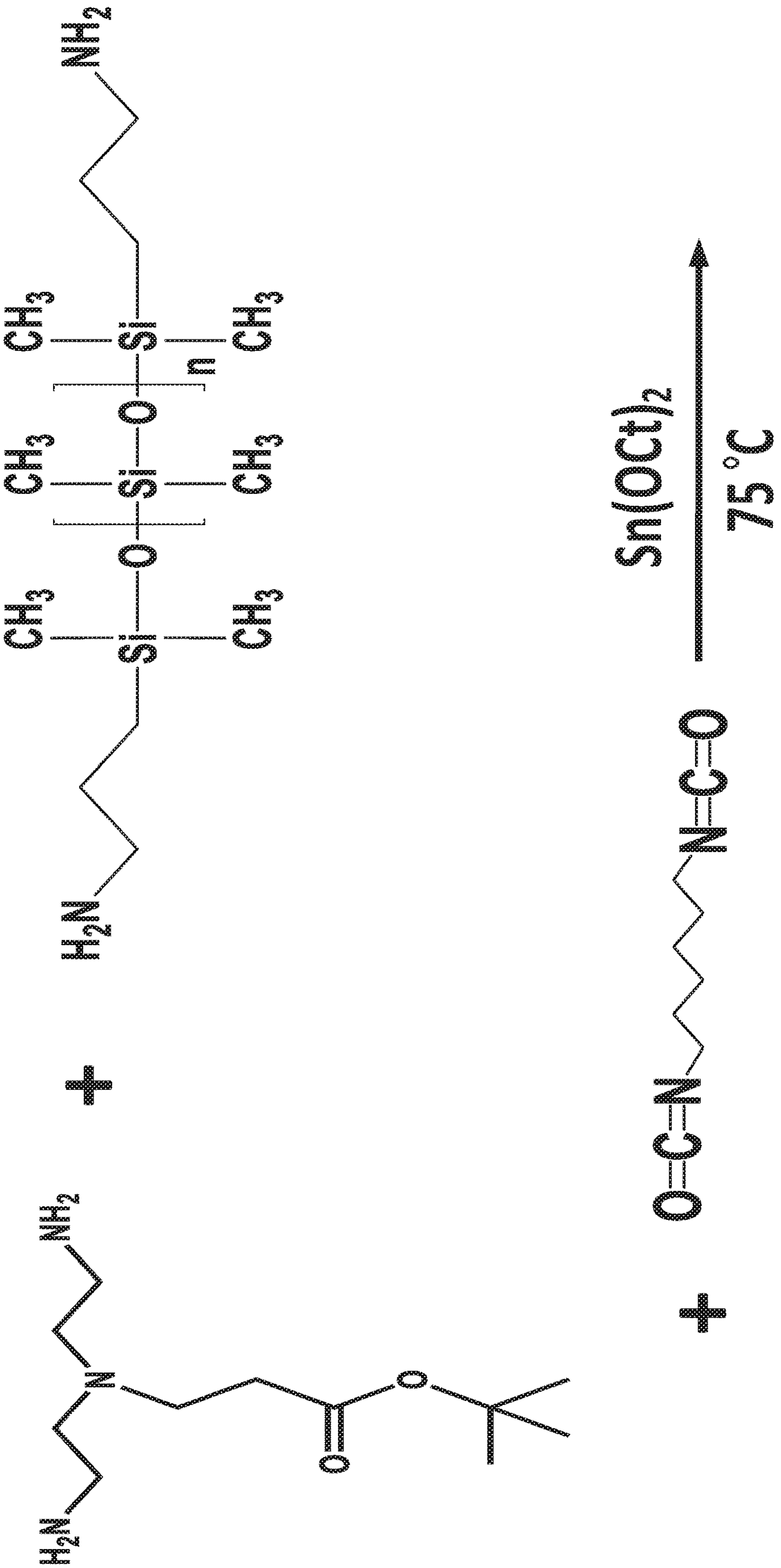
Figure 1D:
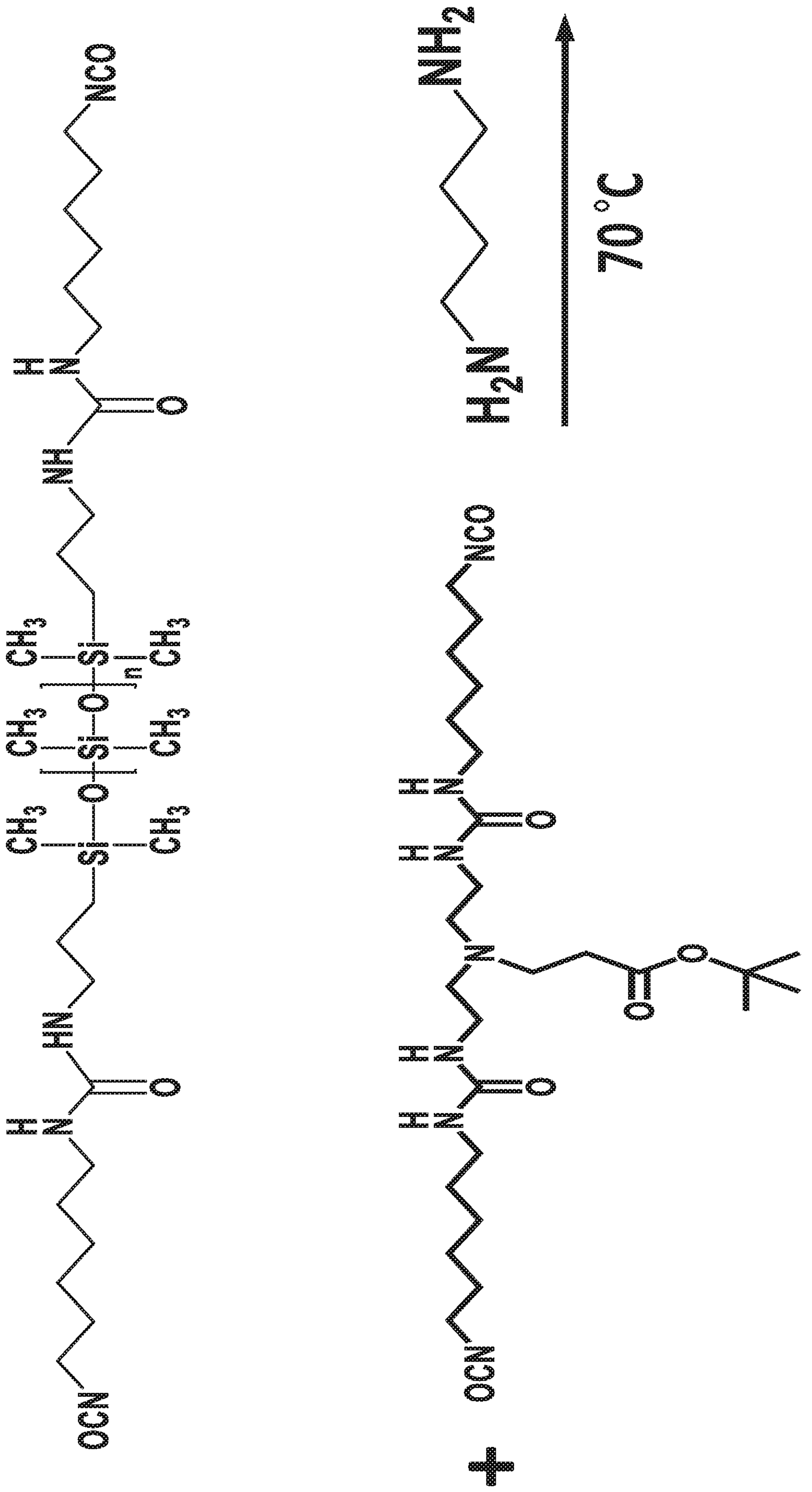
Figure 1D:
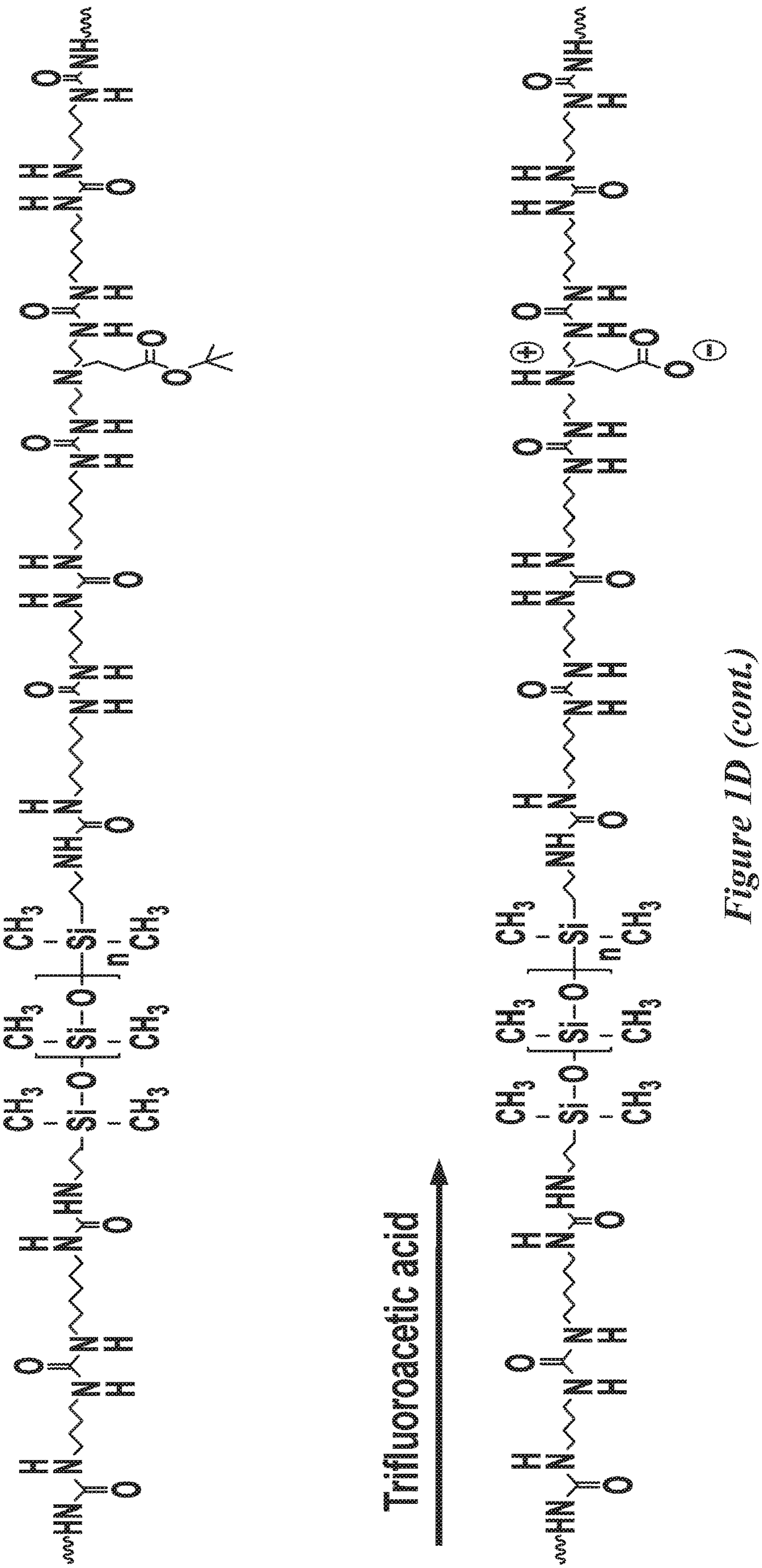

A first aspect of the present application relates to a fiber having a diameter of 1 nm to 10,000 nm, of one or more biocompatible polymers, where the polymers have a backbone including a positively charged component of a zwitterionic moiety.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "zwitterion" as used herein refers to a moiety including both positively and negatively charged groups in the same molecule. Without being bound by any theory, it is believed that the zwitterion functional groups may provide improved hydrophilicity and biocompatibility.

The term "copolymer" refers to a polymer derived from more than one species of monomer.

The term "random copolymer" or "random polymer" refers to a copolymer in which there is no definite order for the sequence of the different building blocks (-M1M2M1M1M2M1M2M2-, wherein M1 and M2 represent different monomers)

The term "block copolymer" or "block polymer" refers to a macromolecule consisting of long sequences of different repeat units. Exemplary block polymers include, but are not limited to AnBm, AnBmAm, AnBmCk, or AnBmCkAn, wherein A, B, and C represent the different monomers, and n, m, and k are the number of monomers present in each block.

The term "alkyl" means an aliphatic hydrocarbon group which may be straight or branched. When not otherwise restricted, the term refers to an alkyl of 20 or fewer carbons. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, 3-pentyl, and the like.

The term "aryl" means an aromatic monocyclic or multicyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

"Unsubstituted" atoms bear all of the hydrogen atoms dictated by their valency.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, lower alkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. When a substituent is keto (i.e., =O), then two hydrogens on the atom are replaced. Combinations of substituents and/or variables are permissible only if such combinations result in stable compounds. A "stable compound" is meant to be a compound that is sufficiently robust to survive isolation to a useful degree of purity from a reaction mixture, and formulation into an efficacious therapeutic agent.

The term "pendant functional group," as used herein refers to a functional group that is a pendant branch from the backbone of a co-polymer. In one embodiment, the pendant functional group provides a location where additional functional groups, can be attached to the backbone of the polymer The term "backbone," "backbone chain" or "main chain," as used herein, refers to the linear chain to which all other chains, long or short or both, may be regarded as being pendant. The backbone chain or main chain of a polymer may be the series of covalently bounded atoms that together create the continuous chain of the molecule.

The term "biocompatible" as used herein, refers to a material that is inert when introduced into a biological system. A biocompatible material will not be broken down (biodegradable) and will not cause a reaction in the biological system in which is it introduced.

The term "a derivative thereof" refers to a salt thereof, an ester thereof, a free acid form thereof, a free base form thereof, a solvate thereof, a deuterated derivative thereof, a hydrate thereof, an N-oxide thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

The fibers of the present application can be used in surgical sutures, and in vascular conduit scaffolds, such as a tubular scaffold for use in vascular regeneration.

In one embodiment of the fiber of the present application, the fiber includes a zwitterionic sulfobetaine-based polyurethane polymer of formula (I):

(I)

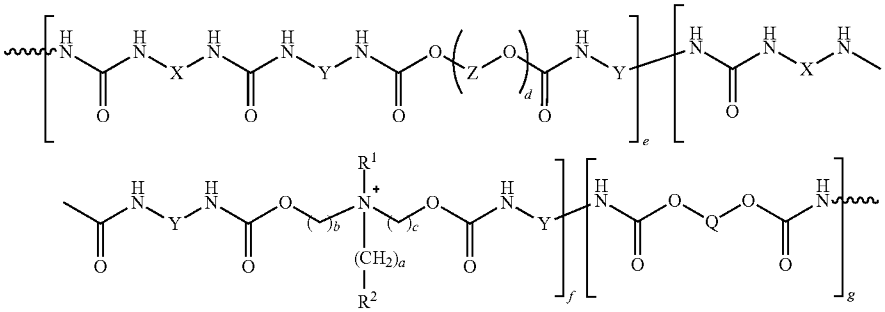

where

X is a substituted or unsubstituted $C_{1-20}$ alkylene, or

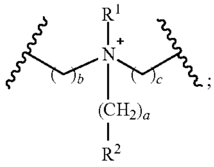

;

Y is a $C_{1-20}$ alkylene,

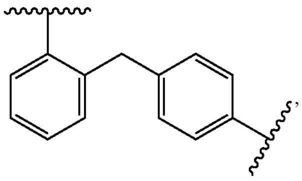

,

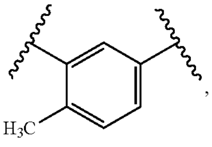

,

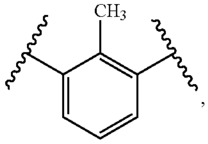

,

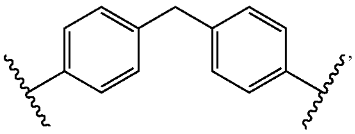

,

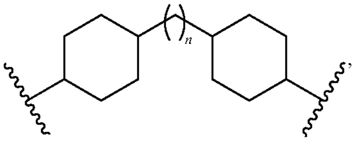

, or

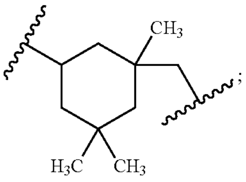

;

Z is independently selected at each occurrence from a $C_{1-6}$ alkylene, and dimethyl silyl;

Q is

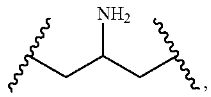

,

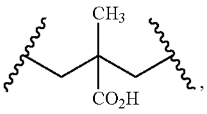

, or

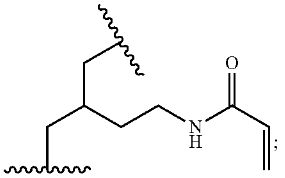

;

$R^1$ is a $C_{1-10}$ alkyl;

$R^2$ is $SO_3^-$, $CO_2^-$, phosphate, or

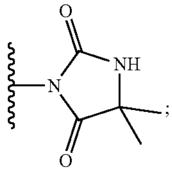 [SMILES: *N1C(=O)NC(C)(C)C1=O]

;

a, b, c, d and n are independently selected integers from 1 to 20;

e and f are independently integers from 1 to 10,000,000;

g is an integer from 0 to 10,000,000; and

indicates a point of attachment.

Polyurethane resins are usually produced by a reaction between a polyisocyanate component and a polyol component, and are widely used in various fields of industry, for example, as elastomers, lenses, synthetic leather, slush powders, elastic molded articles, RIM molded articles, paints, adhesives, sealing materials, or foams. In the present application, isocyanates are reacted with a zwitterionic monomer to produce a polyurethane polymer wherein the zwitterion is incorporated into the backbone of the polymer.

In the preparation of the zwitterionic polyurethane polymer of the present application. polyisocyanates, for example, diisocyanate such as alicyclic diisocyanate, aliphatic diisocyanate, aralkyl diisocyanate, and aromatic diisocyanate may be used, as long as the properties of the polyurethane resin of the present application are not impaired.

Examples of the alicyclic diisocyanate include 1,3-cyclopentane diisocyanate, 1,4-cyclohexane diisocyanate, 1,3-cyclohexane diisocyanate, 3-isocyanatomethyl-3,5,5-trimethyl cyclohexyl isocyanate (also known as isophorone diisocyanate), 4,4'-methylene-bis(cyclohexyl isocyanate), methyl-2,4-cyclohexane diisocyanate, methyl-2,6-cyclohexane diisocyanate, 1,3-bis(isocyanatomethyl)cyclohexane, 1,3-bis(isocyanatoethyl)cyclohexane, 1,4-bis(isocyanatoethyl)cyclohexane, and 2,5- or 2,6-bis(isocyanatomethyl)norbornane (NBDI) and mixtures thereof.

Examples of the aliphatic diisocyanate include trimethylene diisocyanate, tetramethylene diisocyanate, pentamethylene diisocyanate, hexamethylene diisocyanate, 1,2-propylene diisocyanate, 1,2-butylene diisocyanate, 2,3-butylene diisocyanate, 1,3-butylene diisocyanate, 2,4,4- or 2,2,4-trimethyl hexamethylene diisocyanate, and 2,6-diisocyanato methyl caproate.

Examples of the aralkyl diisocyanate include 1,3- or 1,4-xylylene diisocyanate or mixtures thereof, 1,3- or 1,4-tetramethylxylylene diisocyanate or mixtures thereof, and ω,ω'-diisocyanato-1,4-diethylbenzene.

Examples of the aromatic diisocyanate include 2,4-tolylene diisocyanate and 2,6-tolylene diisocyanate, and isomeric mixtures of these tolylene diisocyanates; 4,4'-diphenylmethane diisocyanate, 2,4'-diphenylmethane diisocyanate, and 2,2'-diphenylmethane diisocyanate, and any isomeric mixtures of these diphenylmethane diisocyanates; toluoylene diisocyanate, paraphenylene diisocyanate, and naphthalene diisocyanate.

Derivatives of these diisocyanates may be used in combination. More specifically, a multimer of these diisocyanates (dimers or trimers (e.g., isocyanurate-modified products)) may also be used in combination.

In one embodiment of the zwitterionic polyurethane polymer of the present application, the polyisocyanate is selected from the group including hexamethylene diisocyanate, poly(hexamethylene diisocyanate), dicyclohexylmethane 4,4'-diisocyanate, isophorone diisocyanate, 4,4'-diphenylmethane diisocyanate, toluene diisocyanate, ethylene diisocyanate, and paraphenyl diisocyanate.

In another embodiment of the fiber of the present application, the fiber includes a zwitterionic sulfobetaine-based nylon polymer of formula (II)

(II)

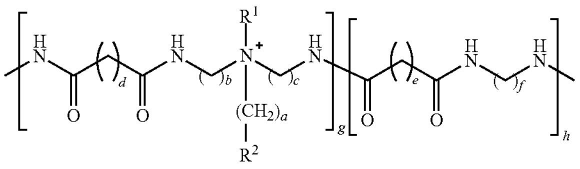

where $R^1$ is a $C_{1-10}$ alkyl;

$R^2$ is $SO_3^-$, $CO_2^-$, phosphate, or

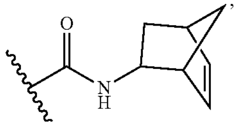

;

a, b, c, d, e, and f are independently selected integers from 1 to 20;

g and h are integers from 1 to 10,000,000; and

indicates a point of attachment.

Nylon is the generic name for a family of polyamide polymers characterized by the presence of the amide group-CONH in the backbone. A polyamide of the present application may comprise the polycondensation polymerization reaction product (or residue) of a zwitterionic diamine component and a dicarboxylic acid (or a diacid chloride) component, and/or by ring opening polymerization of lactams. "Residue," when used in reference to the components of the polyamide of this application, refers to the moiety that is the resulting product of the chemical species in a particular reaction scheme, or subsequent formulation or chemical product, regardless of whether the moiety is actually obtained from the chemical species.

The polyamides are generally prepared by processes which are well known in the art. Examples of methods of polyamide synthesis which may be useful in the present application are disclosed in U.S. Pat. No. 2,130,523 to Carothers; U.S. Pat. No. 6,737,464 to Bagrodia et al.; U.S. Pat. No. 8,057,732 to Bersted et al.; U.S. Pat. No. 6,531,529, to Bersted et al.; 6,359,055, to Delannoy et al.; and 5,665,815 to Vankan et al., all of which are hereby incorporated by reference in their entirety.

In one embodiment of the fiber of the present application, the zwitterionic polymers may include a polydimethylsiloxane group in the backbone of the polymer.

In a further embodiment of the fibers of the present application, the fiber includes a zwitterionic sulfobetaine-based polydimethylsiloxane polymer of formula (III)

(III)

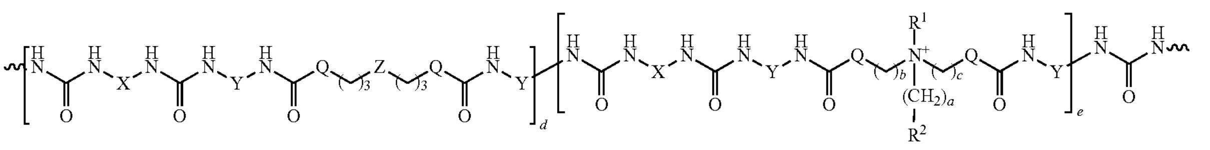

where

X and Y are independently selected from a substituted or unsubstituted $C_{1-20}$ alkylene;

Q is O or NH;

Z is a polydimethylsiloxane;

$R^1$ is H, or $C_{1-10}$ alkyl;

$R^2$ is $SO_3^-$, $CO_2^-$, or phosphate;

a, b, and c are independently selected integers from 1 to 20; and d and e are independently integers from 1 to 10,000,000.

FIGS. 1A-1D shows possible reaction schemes for the formation of exemplary polymers of the present application. These polymers have a polydimethylsiloxane in the backbone and are formed from the reaction of diols and diamines with diisocyanates. The zwitterionic moiety is then formed from the reaction of the polymer with trifluoroacetic acid.

In one embodiment, the biocompatible zwitterionic polymers of the present application can be formed by any one of, but not limited to the following techniques; reversible addition-fragmentation chain transfer (RAFT) polymerization, atom transfer radical polymerization (ATRP), nitroxide mediated polymerization (NMP), cyanoxyl-mediated free radical polymerization, conventional radical polymerization, ring opening polymerization (ROP), emulsion polymerization, suspension polymerization, and the like. All of which methods would be known to one of skill in the art. Nitroxide-mediated radical polymerization refers to a method of radical polymerization that makes use of an alkoxyamine initiator to generate polymers with well controlled stereochemistry and a very low polydispersity index. Ring-opening polymerization, refers to a form of chain-growth polymerization, in which the terminal end of a polymer chain acts as a reactive center where further cyclic monomers can react by opening its ring system and form a longer polymer chain. The propagating center may be radical, anionic or cationic. Anionic ring-opening polymerizations or "AROP", refers to ring-opening polymerizations that involve nucleophilic reagents as initiators. Ring-opening may be triggered by the nucleophilic attack of the initiator to the carbon, forming a new species that will act as a nucleophile. The sequence may repeat until the polymer is formed. A typical example of anionic ROP is that of ε-caprolactone, initiated by an alkoxide functional group.

The zwitterionic polymers of the present application can further include polyols. Suitable polyols for useful in the formation of the zwitterionic polymers of the present application include, but are not limited to, ethylene glycol, propylene glycol, polycaprolactone diol, dipropylene glycol, 1,2,4-butanetriol, 1,7-heptanediol, glycerol, polycaprolactone diol, poly(tetrahydrofuran), isosorbide, polyethylene glycol, butylene glycol, polyethylene oxide, panaxatriol, panaxytriol, talose, balsaminol B, momordol, erythritol, enterodiol, xylitol, miglitol, sorbitol, mannitol, galactitol, isomalt, and maltitol. Suitable polyols can also include saccharides such as aldohexose, aldopentose, aldotetrose, aldotriose, aldose, allose, altrose, arabinose, amylopectin, amylose, dextrose, erythrose, fructose, galactose, glucose, gulose, hexose, idose, ketohexose, ketose, lactose, lyxose, maltose, mannose, pentose, ribose, saccharose, sucrose, talose, tetrose, triose, xylose, as well as their respective stereoisomers. The diols may be polymers of differing molecular weights, or contain a mixture of molecular weights.

In the formation of the zwitterionic polyurethane polymers of the present application, a catalyst selected from the group including dibutyltin dilaurate, triethylamine, triethylenediamine, N-methylmorpholine, tetramethyltin, tetraoctyltin, dimethyldioctyltin, and triethyltin chloride can be used.

Additional methods for the formation of polyurethane polymers that may be suitable for use in the present application are disclosed in U.S. Pat. No. 8,722,752 to Kuwamura et al.; U.S. Pat. No. 4,826,944 to Hoefer et al.; U.S. Pat. No. 4,742,087 to Kluth et al.; U.S. Pat. No. 2,833,730 to Barthel; and U.S. Pat. No. 8,492,433 to Selifonov, all of which are hereby incorporated by reference in their entirety.

Suitable dicarboxylic acids useful for the formation of the zwitterionic nylon polymers of the present application include aliphatic dicarboxylic acid such as oxalic acid, succinic acid, adipic acid or sebasic acid. Other types of dicarboxcylic acids may also be used in the nylons of the present application including alicyclic dicarboxylic acids such as cyclobutanedicarboxylic acid, hexahydroterephthalic acid or hexahydroisophthalic acid; aromatic dicarboxylic acids such as phthalic acid, isophthalic acid, terephthalic acid, methylterephthalic acid, naphthalene-2,6-dicarboxylic acid or naphthalene-2,7-dicarboxylic acid; carboxylic acids such as diphenylether dicarboxylic acid, diphenyl sulfonedicarboxylic acid, diphenoxyethanedicarboxylic acid, or sodium 3.-5-dicarboxybenzenesulfonate, and hydroxycarboxylic acids such as glycolic acid, p-hydroxybenzoic acid or p-B-hydroxyethoxybenzoic acid.

In the formation of the zwitterionic nylon polymers of the present application the use of a catalyst may and or may not be necessary. The use of a catalyst will depend on the monomers chosen. In some embodiment, the zwitterionic nylon polymer may require the use of an acid or base catalyst, selection of such would be apparent to a person of skill in the art.

The polymerization solutions for the formation of the zwitterionic polymers of the present application may also comprise an initiator. Suitable initiators depend greatly on the details of the polymerization, including the types of monomers being used, the type of catalyst system, the solvent system, and the reaction conditions. Initiators generate an active center (e.g., a radical or cation) that can react with the monomers in the reaction mixture thereby starting the polymerization process.

In some embodiments, the initiator may be a photoinitator, a thermal initiator, an ultraviolet initiator, or another type of initiator.

Photoinitiators when irradiated with UV light, produce free radicals which initiate photopolymerization. The initiator may be, for example, 2-hydroxy-4'-(2-hydroxyethoxy)-2-methylpropiophenone, a benzoin ether, a benzil ketal, an a-dialkoxyacetophenone, an α-hydroxyphenone, an α-amino-alkylphenone, an acylphosphine oxide, a benzophenone/amine, a thioxanthone/amine, azobisisobutyronitrile, lithium phenyl-2,4,6-trimethylbenzoylphosphinate, or a combination thereof. Other examples of suitable photo initiators include acetophenone; anisoin; anthraquinone; anthraquinone-2-sulfonic acid, sodium salt monohydrate; tricarbonylchromium; benzil; benzoin, sublimed; benzoin ethyl ether; benzoin isobutyl ether; benzoin methyl ether; benzophenone; benzophenone/1-hydroxycyclohexyl phenylketone, 50/50 blend; 3,3',4,4'-benzophenonetetracarboxylic dianhydride; 4-benzoylbiphenyl; 2-benzyl-2-(dimethylamino)-4'-morpholinobutyrophenone; 4,4'-bis(diethylamino)benzophenone; 4,4'-bis(dimethylamino)benzophenone; camphorquinone; 2-chlorothioxanthen-9-one; (cumene)cyclopentadienyliron(II) hexafluorophosphate; dibenzosuberenone; 2,2-diethoxyacetophenone; 4,4'-dihydroxybenzophenone; 2,2-dimethoxy-2-phenylacetophenone; 4-(dimethylamino)benzophenone; 4,4'-dimethylbenzil; 2,5-dimethylbenzophenone; 3,4-dimethylbenzophenone; diphenyl(2,4,6-trimethylbenzoyl)phosphine oxide/2-hydroxy-2-methylpropiophenone, 50/50 blend; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methybenzoylformate; 2-methyl-4'-(methylthio)-2-morpholinopropiophenone; phenanthrenequinone; 4'-phenoxyacetophenone; thioxanthen-9-one; triarylsulfonium hexafluoroantimonate salts, mixed, 50% in propylene carbonate; triarylsulfonium hexafluorophosphate salts, mixed, 50% in propylene carbonate, or a combination thereof.

Thermal radical initiators decompose upon heating into radical fragments which initiate polymerization. Exemplary thermal radical initiators include ammonium persulfate; sodium metabisulfite; benzoyl peroxide; di-t-amyl peroxide; t-butyl peroxy benzoate; di-cumyl peroxide; azobisisobutyronitrile (AIBN); 1,1' azobis(cyclohexanecarbonitrile) (ABCN); 4,4'-Azobis(4-cyanovaleric acid) (ACVA); 2,2'-azobis(2,4-dimethylpentanenitrile); and 2,2'-azobis(cyclohexanecarbonitdle).

The initiator in the polymerization solution can range from about 0.01 wt % to 10 wt %.

Additionally, the polymerization solution may further comprise a cross-linking agent. The crosslinking agents interact with the reactive groups on the zwitterionic polymers, whether part of the backbone or a pendent group. The crosslinking agents chemically bond together two polymer chains in the reaction mixture, thereby exponentially increasing the molecular weight of the polymer.

Suitable classes of cross-linkers are selected from the group consisting of isocyanates, anhydrides, multiply (meth) acrylated cross linkers, polyacids, and acid halides. The cross-linking agent may be, for example, poly(ethylene glycol)dimethacrylate, tetramethylethylenediamine, carboxybetaine diacrylamide cross-linker, carboxybetaine diacrylate, other bifunctional and multi-functional monomers and macromers, or a combination thereof.

The crosslinking agents may be diisocyanates. Exemplary diisocyanates suitable for the present application are disclosed supra. Other crosslinking agents that could interact with the residual reactive groups on the zwitterionic polymers of the present application include multiply (meth) acylated cross-linkers such as diethyleneglycol dimethacrylate (DEGDMA), diethylene glycol diacrylate, triethylene glycol dimethacrylate (TEGDMA), ethyleneglycol dimethacrylate (EGDMA), hexane-1,6-diol diacrylate (HDDA), ethylene glycol diacrylate, ethylene glycol dimethacrylate, poly(ethylene glycol) diacrylate, poly(ethylene glycol) dimethacrylate, tetra(ethylene glycol) diacrylate, or triethylene glycol dimethacrylate.

Furthermore, crosslinking agents such as poly acids, anhydrides, and acid halides may also be used. Exemplary cross linkers of these types include maleic acid, 2-methylmaleic acid, itaconic acid, 2-methylitaconic acid, α,β-methyleneglutaric acid, maleic anhydride, itaconic anhydride, acrylic anhydride, methacrylic anhydride, 1, 4-phenylenediacryloyl chloride, etc.

The concentration of the zwitterionic monomers (zwitterionic diols and zwitterionic diamines) and the isocyanates and/or dicarboxylic acids used in any of the herein described polymerization reactions depends partially on the solubility of the monomer and the polymer products as well as the evaporation temperature of the solvent. Solvent concentration can also affect the gelation of the polymer. Insufficient solvent can cause the polymer to crosslink in a shorter time period without reaching high enough conversions. The concentration of the monomer dissolved in the solvent in reactions may range from 1% to 100% weight percentage monomer. Typically, a monomer concentration of less than 90 wt % is suitable to ensure the solubility of the resulting polymers and additionally to prevent premature cross-linking and gelation. In some examples of the formation of the polymers of the present application, the mono Suitable solvents for use in the process of preparing the zwitterionic polymers of the present application are selected based the requirements of the zwitterionic diol and or diamine monomers, isocyanate, and dicarboxylic acid solubility, as well as boiling point compatible with the type of polymerization being used, and the polymerization temperature. Exemplary solvents useful for the formation of the zwitterionic polymers described herein include, but are not limited to water, methanol, ethanol, methylene chloride, toluene, dioxane, THF, chloroform, cyclohexane, dimethyl sulfoxide, dimethyl formamide, acetone, acetonitrile, n-butanol, n-pentanol, chlorobenzene, diethylether, tert butanol, 1,2,-dichloroethylene, diisopropylether, ethanol, ethylacetate, ethylmethylketone, heptane, hexane, isopropylalcohol, isoamylalcohol, methanol, pentane, n-propylalcohol, pentachloroethane, 1,1,2,2,-tetrachloroethane, 1,1,1,-trichloroethane, tetrachloroethylene, tetrachloromethane, trichloroethylene, water, xylene, benzene, nitromethane, glycerol, and mixtures thereof.

The solvent used in the polymerization reactions of the present application can further include stabilizers, surfactants, or dispersants. Suitable surfactants include ionic and nonionic surfactants such as alkyl polyglycol ethers such as ethoxylation products of lauryl, oleyl, and stearyl alcohols; alkyl phenol polyglycol ethers such as ethoxylation products of octyl- or nonylphenol, diisopropyl phenol, triisopropyl phenol; alkali metal ammonium salts of alkyl, aryl or alkylaryl sulfonates, sulfates, phosphates, and the like, including sodium lauryl sulfate, sodium octylphenol glycolether sulfate, sodium dodecylbenzene sulfonate, sodium lauryldiglycol sulfate, and ammonium tritertiarybutyl phenol and penta- and octa-glycol sulfonates, sulfosuccinate salts such as disodium ethoxylated nonylphenol half ester of sulfosuccinic acid, disodium n-octyldecyl sulfosuccinate, sodium dioctyl sulfosuccinate, and the like.

The zwitterionic polymers of the present application can be copolymers, including a random or statistical copolymers, or block copolymers. Furthermore, the zwitterionic polymers of the present application can be mixed together, and or formed from the copolymerization of different monomers or polymer blocks.

Inhibitors can be used to prevent excessive polymerization or crosslinking of the zwitterionic polymers of the present application. Exemplary inhibitors include, but are not limited to, phenothiazine, hydroquinone, or antioxidant inhibitors such as the ETHANOX™ family (SI Group, Schenectady, NY) (e.g., ETHANOX 330™), IRGANOX (BASF, Florham Park, New Jersey) and STABOXOL (Rhein Chemie, Mannheim, Germany).

In a further embodiment of the fibers of the present application, the fibers have a diameter of 1 nm to 10,000 nm. The fibers can be nanofibers with a diameter ranging from 1 nm to 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, or 400 nm. In another embodiment, the fibers have a diameter from 1 nm to 1000 nm; 1 nm to 10,000 nm; 1 nm to 100,000 nm; or 1 nm to 1,000,000 nm. The fibers may be prepared by extruding a polymer solution through a narrow orifice and the extruded filament can then be collected on a rotating spindle as a fiber either by wet, dry, electro, or a melt spinning process. The diameter of the fiber can be controlled based on the concentration of the polymer in solution and the size of the orifice used.

The production of fine fibers from polymeric solution through electrostatic spinning (a.k.a. "electro-spinning") via an electric field created by a voltage differential between a collecting electrode and a spinning electrode is known. For example, as shown in U.S. Pat. No. 6,743,273, polymeric solution is pumped to a spinning electrode in the form of a rotating emitter in which the pump solution is pumped from a reservoir and forced through holes in the emitter. Upon exiting, the electrostatic potential between a grid and the emitter imparts a charge which causes the liquid to be "spun" as thin fine fibers where they are collected on a substrate as an efficiency layer. During this process, the solvent is evaporated off the fine fibers which draws down the fiber diameter during their flight. Additional electrospinning techniques that may be used in the formation of the fibers of the present application are disclosed in U.S. Pat. No. 4,044,404 to Martin et al.; U.S. Pat. No. 7,086,846 to Kleinmeyer et al.; and U.S. Patent Application Publication No. US2006/0290031 to Jirsak et al., all of which are hereby incorporated by reference in their entirety The formation of fibers through melt spinning is well known in the art, and is disclosed in U.S. Pat. Nos. 5,149,517 and 5,156,831 to Fain et al.; U.S. Pat. No. 4,606,872 to Watanabe; U.S. Pat. No. 5,213,677 to Yamamoto et al.; U.S. Pat. No. 4,005,183 to Singer; U.S. Pat. No. 5,037,589 to Iwashita et al.; U.S. Pat. No. 4,628,001 to Sasaki et al.; and U.S. Pat. No. 4,606,808 to Yamada et al., all of which are hereby incorporated by reference in their entirety. In general, melt spinning entails melting the polymer of interest with heating in a spinning cylinder having a spinneret. The molten polymer is extruded out of the spinneret by pressurizing with a gas or by pressing with a piston into a filament which is wound up on a drum rotating at a constant velocity to give a continuous length polymer filament.

A second aspect of the present application relates to an implantable therapeutic delivery system including a housing defining a chamber. The housing is porous and formed from the fibers having a diameter of 1 nm to 10,000 nm, of one or more biocompatible polymers, where the polymers have a backbone including a positively charged component of a zwitterionic moiety.

In one embodiment of the implantable therapeutic delivery system of the present application, the biocompatible polymer includes a zwitterionic sulfobetaine-based polyurethane polymer of formula (I):

(I)

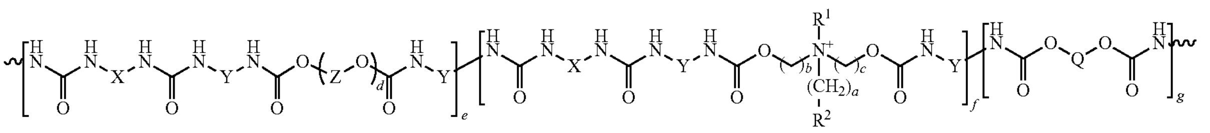

where

X is a substituted or unsubstituted $C_{1-20}$ alkylene, or

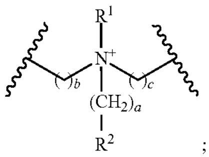

;

Y is a $C_{1-20}$ alkylene,

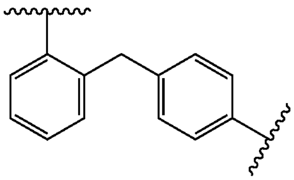

,

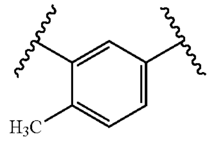

,

-continued

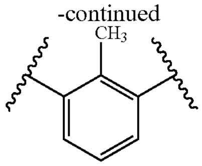

,

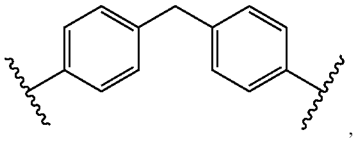

,

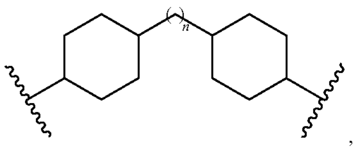

,

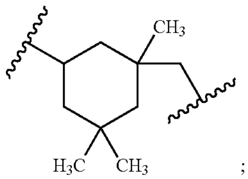

;

Z is independently selected at each occurrence from a $C_{1-6}$ alkylene, and dimethyl silyl;

Q is

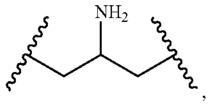

,

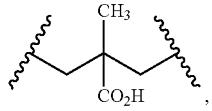

, or

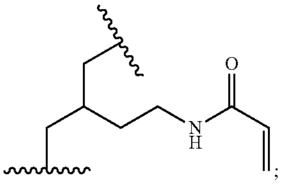

;

$R^1$ is a $C_{1-10}$ alkyl;

$R^2$ is $SO_3^-$, $CO_2^-$, phosphate, or

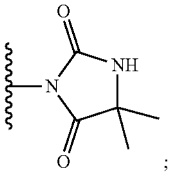 [SMILES: *N1C(=O)NC(C)(C)C1=O ; ";"]

;

a, b, c, d and n are independently selected integers from 1 to 20;

e and f are independently integers from 1 to 10,000,000;

g is an integer from 0 to 10,000,000; and

indicates a point of attachment.

In another embodiment of the implantable therapeutic delivery system of the present application, the biocompatible polymer includes a zwitterionic sulfobetaine-based nylon polymer of formula (II)

(II)

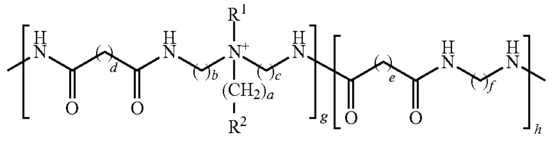

where $R^1$ is a $C_{1-10}$ alkyl;

$R^2$ is $SO_3^-$, $CO_2^-$, phosphate, or

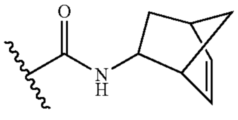

;

a, b, c, d, e, and f are independently selected integers from 1 to 20;

g and h are integers from 1 to 10,000,000; and

indicates a point of attachment.

In a further embodiment of the implantable therapeutic delivery system of the present application, the biocompatible polymer includes a zwitterionic sulfobetaine-based polydimethylsiloxane polymer of formula (III)

(III)

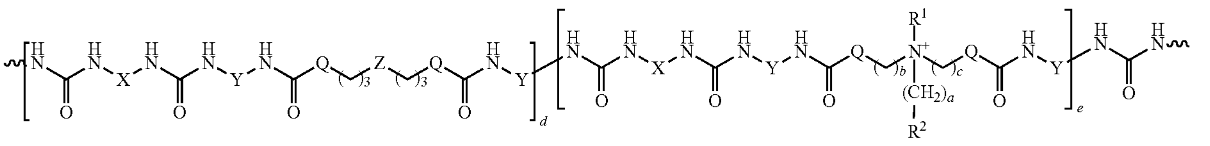

where

X and Y are independently selected from a substituted or unsubstituted $C_{1-20}$ alkylene;

Q is O or NH;

Z is a polydimethylsiloxane;

$R^1$ is H, or $C_{1-10}$ alkyl;

$R^2$ is $SO_3^-$, $CO_2^-$, or phosphate;

a, b, and c are independently selected integers from 1 to 20; and d and e are independently integers from 1 to 10,000,000.

In another embodiment of the implantable therapeutic delivery system, the housing is an elongate hollow porous tube extending between first and second ends with the fibers being wound around the chamber. In a further embodiment of the implantable therapeutic delivery system, the porous tube has a sealed first end. Furthermore, the chamber of hollow porous tube can contain a hydrogel.

Figure 2A:
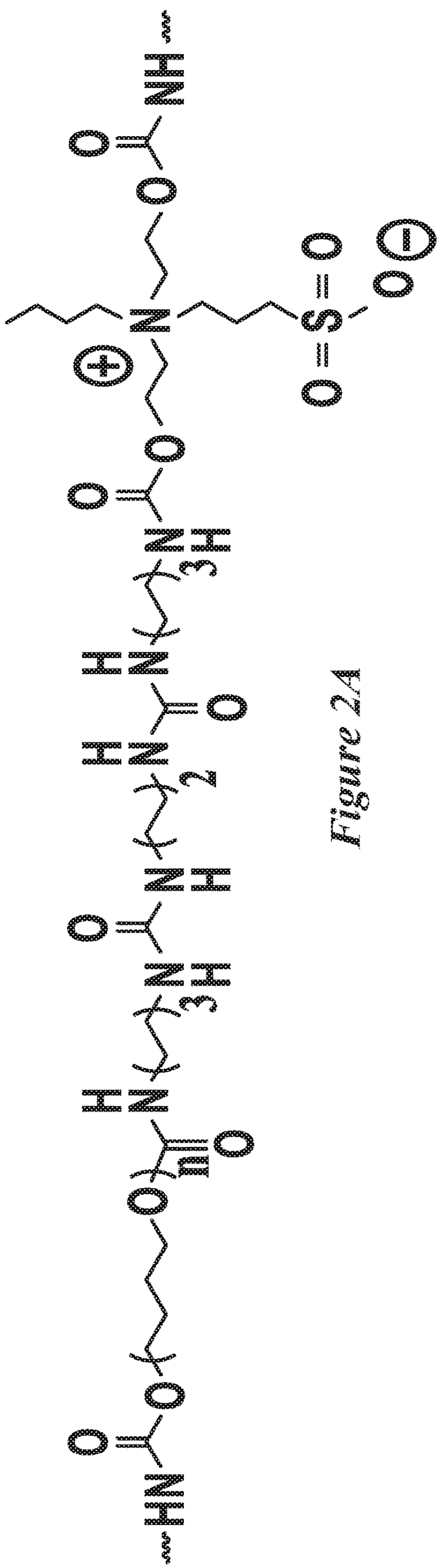
FIGS. 2A-2J show the design and fabrication of the zwitterionical polyurethane (ZPU) device and its material characterizations.
Figure 2C:
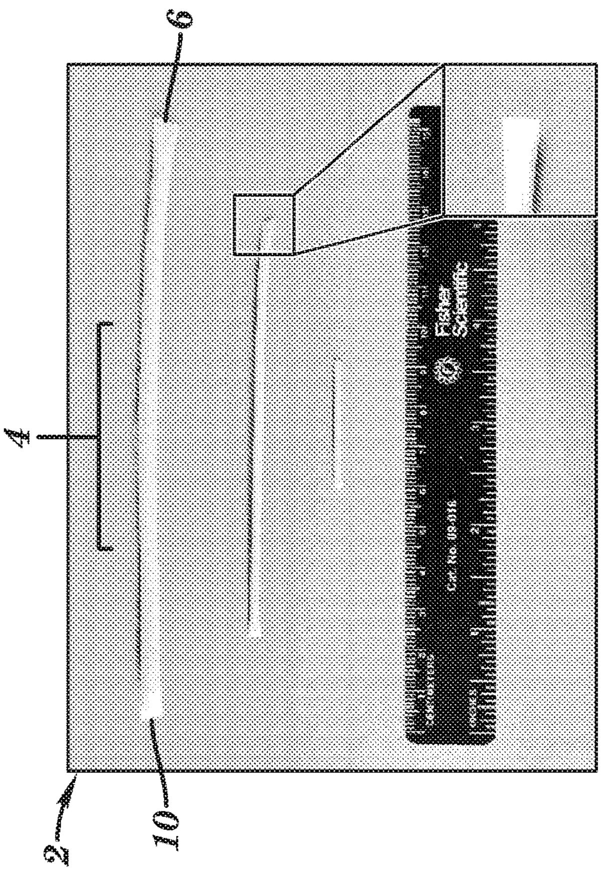
Figure 2B:
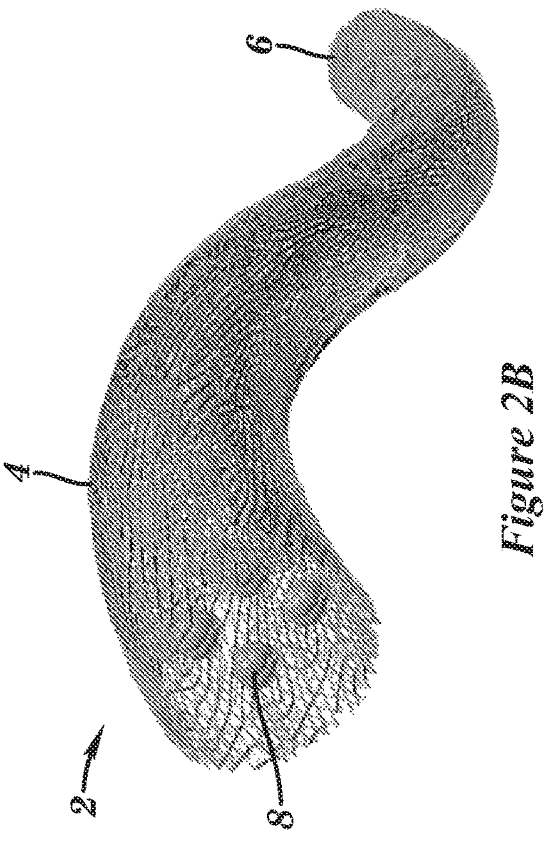

As shown in FIG. 2B, implantable therapeutic delivery system 2 includes fibers forming elongate hollow porous tube 4. Sealed first end 6 holds the hydrogel in elongate hollow porous tube 4. The hydrogel can include cells 8. In FIG. 2C, implantable therapeutic delivery system 2, has sealed first end 6 and sealed second end 10. Sealed first end 6, and sealed second end 10 contain the hydrogel with cells 8 (not visible in FIG. 2C) in implantable therapeutic delivery system 2.

The hydrogel is comprised of a material that can form cross-links with the polymeric fibers of the housing. Suitable hydrogel materials include natural and synthetic polymeric materials. The hydrogel can be homopolymeric, copolymeric, or multipolymeric in composition. Suitable hydrogel materials include, without limitation, those derived from collagen, hyaluronate, fibrin, alginate, agarose, chitosan, bacterial cellulose, elastin, keratin, MATRIGEL™ (Tewksbury MA., Corning Life Sciences), DNA (as a true polymer), and combinations thereof. In other embodiments, suitable hydrogels are synthetic polymers including those derived from polyethylene glycol (PEG), poly(acrylic acid) and derivatives thereof, poly(ethylene oxide) and copolymers thereof, poly(vinyl alcohol), polyphosphazene, and combinations thereof.

In a further embodiment of the implantable therapeutic delivery system, the hydrogel includes alginate. In another embodiment, the hydrogel and porous fiber tube are cross-linked.

Exemplary cationic cross-linking agents suitable for crosslinking the porous fiber tube to the hydrogel of the implantable therapeutic delivery system include divalent cations such as $Ba^{2+}$, $Ca^{2+}$, $Cd^{2+}$, $Cu^{2+}$, $Fe^{2+}$, $Mg^{2+}$, $Mn^{2+}$, $Ni^{2+}$, $Pb^{2+}$, $Sn^{2+}$, $Sr^{2+}$, and $Zn^{2+}$. In one embodiment, the divalent cross-linking agent is calcium chloride. Other suitable cationic cross-linking agents include, without limitation, $Al^{3+}$ and $Fe^{3+}$. The cross-linking agent can be present in the hydrogel, the porous fiber tube, or applied as a solution after addition of the hydrogel to the porous fiber tube. The concentration of the cross-linking agents needs to be sufficient to cross-link and adhere the hydrogel to the porous fiber tube. Accordingly, in some embodiments, the cross-linking agent is present in an excess concentration. Exemplary crosslinking solutions include aqueous solutions of $CaCl_2$, $BaCl_2$.

In a further embodiment of the implantable therapeutic delivery system, the elongate hollow porous tube is sealed at the first and second ends so that the chamber is closed.

The implantable therapeutic delivery system can include a preparation of cells within the closed chamber which release a therapeutic agent from the chamber through the elongate hollow porous tube.

In one embodiment, the therapeutic agent is a biological agent produced and/or secreted or released from tissue and/or a preparation of cells encapsulated within or residing within the hydrogel of the implantable therapeutic delivery system. The cells may comprise naturally occurring or genetically engineered cells which may be in the form of single cells and/or cell clusters. In one embodiment, the cells within the hydrogel of the implantable therapeutic delivery system secrete one or more biological factors that are useful in the treatment of a disease or condition. These factors are secreted from the cells, released from the hydrogel, and are delivered to or diffuse to surrounding target cells, tissue, or organ in need thereof. Suitable cells include, without limitation, one or more cell types selected from the group consisting of smooth muscle cells, cardiac myocytes, platelets, epithelial cells, endothelial cells, urothelial cells, fibroblasts, embryonic fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, embryonic stem cells, mesenchymal stem cells, neural cells, endothelial progenitor cells, hematopoietic cells, and precursor cells.

In one embodiment, the cells are insulin secreting cells, such as pancreatic islet cells.

As noted above, suitable cells include progenitor and/or stem cells. Suitable stem cells may be pluripotent, multipotent, oligopotent, or unipotent cells or cell populations, and include embryonic stem cells, epiblast cells, primitive ectoderm cells, and primordial germ cells. In another embodiment, suitable stem cells also include induced pluripotent stem (iPS) cells, which are pluripotent stem cells derived from a non-pluripotent cell. See Zhou et al., *Cell Stem Cell* 4:381-384 (2009); Yu et al., *Science* 324(5928):797-801 (2009); Yu et al., *Science* 318(5858):1917-20 (2007); Takahashi et al., *Cell* 131:861-72 (2007); and Takahashi and Yamanaka, *Cell* 126:663-76 (2006), which are hereby incorporated by reference in their entirety. In accordance with this embodiment, the hydrogel may further comprise the growth and differentiation factors suitable for promoting stem cell differentiation into a desired population of cells capable of producing and releasing the therapeutic agent of interest.

Suitable cells for use in the implantable therapeutic delivery system described herein can be derived from any animal capable of generating the desired cells. The animals from which the cells are harvested may be vertebrate or invertebrate, mammalian or non-mammalian, human or non-human. Examples of animal sources include, but are not limited to, primate, rodent, canine, feline, equine, bovine, or porcine. The cells may be obtained from or comprise a primary cell preparation or immortalized cells preparations. The cells may be isolated from the same species as the implant recipient or from a different species than the implant recipient.

The islet cells are clusters of cells that produce hormones. Islet equivalent (IEQ) is often applied to describe the density of islet cells. Islet cell aggregates (or whole islets) can contain about 1500-2000 cells for each aggregate of 150 μm diameter, which is defined as one islet equivalent. In some embodiments, the system described herein comprises an islet cell density between approximately $1\times10^3$ IEQ islet cells/ml to about $1\times10^6$ IEQ islet cells/mL or more. In one embodiment, the cell holding capacity of the system is based, at least in part, on the length of the system. The cells are capable of surviving in vivo in the implantable system for at least a month, two months, three months, four months, five months, six months, seven months, eight months, nine months, ten months, eleven months, twelve months or a year or more with a functionality that represents at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more of the function expressed at the time the cells are/were introduced into the system or at the time the cells fully develop and/or mature in the system, e.g., implantation of progenitor cells which need to further develop or mature to functional cells in vivo. In some embodiments, the cells or cell preparation in the system expand within the system to increase cell density and/or cell function upon implantation of the system in vivo.

When the hydrogel of the implantable therapeutic delivery system contains cells or a cell preparation, additional cell specific growth and/or differentiation factors may be added to the hydrogel solution to enhance cell growth, differentiation, and survival. These factors include supplements (e.g., glutamine, non-essential amino acids), growth factors (e.g., epidermal growth factors, fibroblast growth factors, transforming growth factor/bone morphogenetic proteins, platelet derived growth factors, insulin growth factors, cytokines), extracellular matrix proteins (e.g., fibronectin, laminin, heparin, collagen, glycosaminoglycan, proteoglycan, elastin, chitin derivatives, fibrin, and fibrinogen), angiogenic factors (e.g., FGF, bFGF, acid FGF (aFGF), FGF-2, FGF-4, EGF, PDGF, TGF-beta, angiopoietin-1, angiopoietin-2, placental growth factor (PIGF), VEGF, and PMA (phorbol 12-myristate 13-acetate)), and signaling factors and/or transcription factors.

In a further embodiment of the implantable therapeutic delivery system of the present application, the elongate hollow porous tube has pores of a diameter of 10 nm to 1 mm. Ideally, the pores of the system are large enough to allow the flow of the therapeutic agent out of the system into the subject, but not so large as to allow migration of the cells out of the implantable therapeutic delivery system.

The tensile strength of the elongate hollow porous tube of the implantable therapeutic delivery system can range from 0.01 Mpa to 100 Mpa.

The diameter of the implantable system is generally in the range of microns to centimeters. In one embodiment, the diameter of the chamber of the elongate hollow porous tube is from 0.1 mm to 10 cm. For example, the diameter of the implantable system can be 0.1 mm, 0.5 mm, 1 mm, 5 mm, 10 mm, 20 mm, 30 mm, 40 mm, 50 mm, 60 mm, 70 mm, 80 mm, 90 mm, or 100 mm.

The elongate hollow porous tube can have a wall thickness of 10 μm to 1 cm. Additionally, the elongate hollow porous tube can have a length of 1 cm to 10 m.

Another aspect of the present application relates to a method of preparing an implantable therapeutic delivery system. The method includes providing the fiber having a diameter of 1 nm to 10,000 nm, of one or more biocompatible polymers, where the polymers have a backbone including a positively charged component of a zwitterionic moiety. Then the fiber is applied around a form to create an elongate porous tube. The elongate porous tube is then removed from the form to produce an elongate hollow porous tube defining a chamber within it and extending between first and second open ends. This is followed by sealing the first end of the elongate hollow porous tube to close the first end, with the second end being left open. A hydrogel is then inserted into the chamber through the open second end. The hydrogel is then crosslinked to the fibers of the elongate hollow porous tube, and the second end of the elongate hollow porous tube is sealed.

In another embodiment of the method of preparing an implantable therapeutic delivery system, the applying of the fibers around a form to create an elongate porous tube is accomplished via electrospinning. The electrospun polymeric fiber can be directly wound around a cylindrical form during the electrospinning process.

In a further embodiment of the method of forming the implantable therapeutic delivery system of the present application, the crosslinking entails exposing the implantable therapeutic delivery system to a crosslinking agent. Suitable crosslinking agents are discussed supra. Additionally, as discussed supra, the hydrogel can include a preparation of cells, and these cells can be islet cells.

In another embodiment of the method of preparing the implantable therapeutic delivery system of the present application, the polymers of the fibers include a zwitterionic sulfobetaine-based polyurethane polymer of formula (I):

(I)

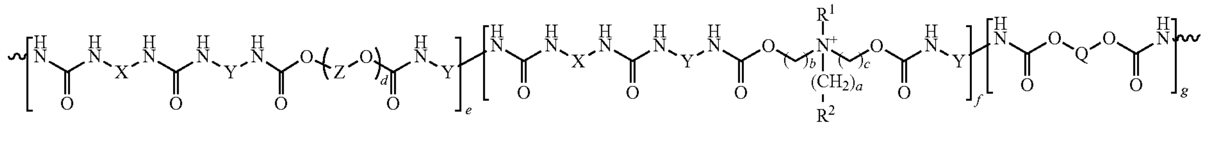

where

X is a substituted or unsubstituted $C_{1-20}$ alkylene, or

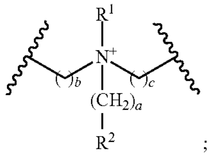

;

Y is a $C_{1-20}$ alkylene,

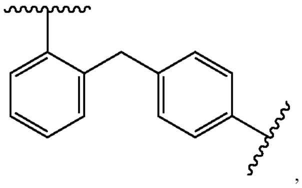

,

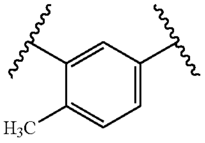

,

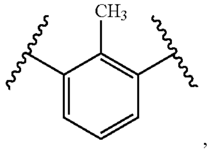

,

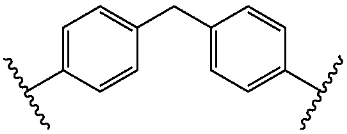

,

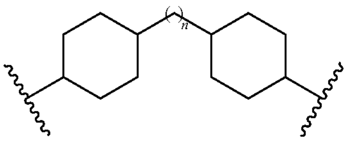

,

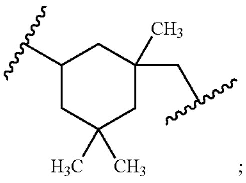

;

Z is independently selected at each occurrence from a $C_{1-6}$ alkylene, and dimethyl silyl;

Q is

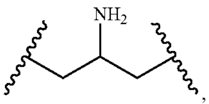

,

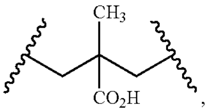

, or

-continued

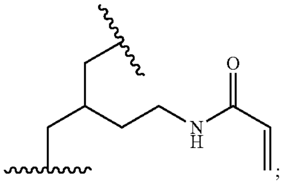

;

$R^1$ is a $C_{1-10}$ alkyl;

$R^2$ is $SO_3^-$, $CO_2^-$, phosphate, or

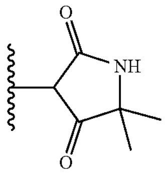

;

a, b, c, d and n are independently selected integers from 1 to 20;

e and f are independently integers from 1 to 10,000,000;

g is an integer from 0 to 10,000,000; and

indicates a point of attachment.

In another embodiment of the method of preparing the implantable therapeutic delivery system of the present application, the polymers of the fibers include a zwitterionic sulfobetaine-based nylon polymer of formula (II)

(II)

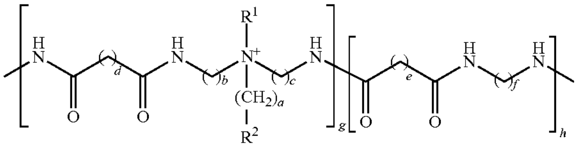

where $R^1$ is a $C_{1-10}$ alkyl;

$R^2$ is $SO_3^-$, $CO_2^-$, phosphate, or

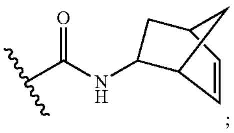 [SMILES: *C(=O)NC1CC2C=CC1C2 ; ";"]

;

a, b, c, d, e, and f are independently selected integers from 1 to 20;

g and h are integers from 1 to 10,000,000; and

indicates a point of attachment.

In a further embodiment of the method of preparing the implantable therapeutic delivery system of the present application, the polymers of the fibers include a zwitterionic sulfobetaine-based polydimethylsiloxane polymer of formula (III)

(III)

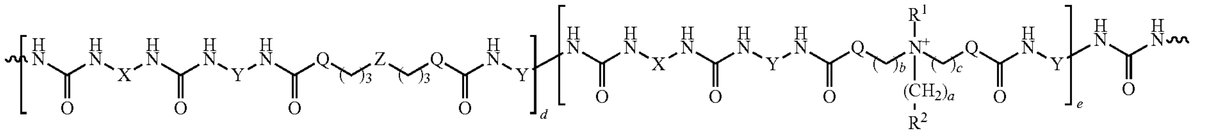

where

X and Y are independently selected from a substituted or unsubstituted $C_{1-20}$ alkylene;

Q is O or NH;

Z is a polydimethylsiloxane;

$R^1$ is H, or $C_{1-10}$ alkyl;

$R^2$ is $SO_3^-$, $CO_2^-$, or phosphate;

a, b, and c are independently selected integers from 1 to 20; and d and e are independently integers from 1 to 10,000,000.

A further aspect of the present application relates to a method of treating diabetes including selecting a subject having diabetes, and implanting the implantable therapeutic delivery system of the present application into the selected subject.

Diabetes can be divided into two broad types of diseases: type I (T1D) and type II (T2D). The term "diabetes" also refers herein to a group of metabolic diseases in which patients have high blood glucose levels, including type I diabetes (T1D), type II diabetes (T2D), gestational diabetes, congenital diabetes, maturity onset diabetes (MODY), cystic fibrosis-related diabetes, hemochromatosis-related diabetes, drug-induced diabetes (e.g., steroid diabetes), and several forms of monogenic diabetes.

Thus, in one embodiment, the subject has been diagnosed as having one or more of type I diabetes (T1D), type II diabetes (T2D), gestational diabetes, congenital diabetes, maturity onset diabetes (MODY), cystic fibrosis-related diabetes, hemochromatosis-related diabetes, drug-induced diabetes, or monogenic diabetes.

Another aspect of the present application relates to a method of delivering a therapeutic agent to a subject. The method includes implanting the implantable therapeutic delivery system of the present application into a subject.

Suitable conditions or diseases for treatment using the implantable therapeutic delivery system include, inter alia, chronic conditions or disease states requiring long term repeated administration of a therapeutic agent. In one embodiment, the condition is diabetes which requires ongoing insulin therapy.

The implantable therapeutic delivery system described herein can be employed for treating a variety of diseases and conditions requiring a continuous supply of biologically active substances to the organism. The system may contain homogenous or heterogenous mixtures of biologically active agents and/or cells, or cells producing one or more biologically active substances of interest. The biologically active agents and/or cells are wholly encapsulated within the elongate porous tube. Such a semi-permeable outer layer allows the encapsulated biologically active substance of interest (e.g., insulin, glucagon, pancreatic polypeptide, and the like in the case of treating diabetes) to pass out of the system, making the active substance available to target cells outside the system and in the recipient subject's body. In one embodiment, the semi-permeable elongate porous tube allows nutrients naturally present in the subject to pass through the membrane to provide essential nutrients to cells present in the hydrogel. At the same time, such a semi-permeable membrane prevents the recipient subject's cells, more particularly, their immune system cells, from passing through and into the implantable system to harm the cells in the system. For example, in the case of diabetes, this approach can allow glucose and oxygen (e.g., contained within the body) to stimulate insulin-producing cells of the implant system to release insulin as required by the body in real time while preventing host immune system cells from recognizing and destroying the implanted cells.

The implantable therapeutic delivery system can be surgically implanted into subjects. In one embodiment, the system is implanted using minimally invasive surgical techniques such as laparoscopy. The system can be implanted percutaneously, subcutaneously, intraperitoneally, intrathoracically, intramuscularly, intraarticularly, intraocularly, or intracerebrally depending on the therapeutic agent being delivered, condition to be treated, and tissue or organ targeted for delivery.

In one embodiment, the implantable therapeutic delivery system is anchored or immobilized (e.g., by suture) at the implantation site to maintain the system and/or the released therapeutic agent at or near the implantation site. In one embodiment, the anchor site is at or close in proximity to, a tissue or organ which is the focus of the treatment. In other embodiments where delivery of the therapeutic agent from the system is not location dependent and biodistribution of the agent is dependent on the subject's vasculature or body fluids, the system can be implanted and anchored in a remote location. In one embodiment, the implantable delivery system is implanted percutaneously or subcutaneously under the skin on the abdomen, forearm, flank, back, buttocks, leg, and the like, where it substantially remains until such time as it is required to be removed.

In another embodiment, the implantable therapeutic delivery system is retrievable after implantation. Anchoring or immobilizing the system as described supra prevents the system from migrating, moving, or traversing inside the patient and facilitates easy retrieval. In accordance with this embodiment, the system may further comprise a tether that aids in retrieval. Retrieval is desirable when the cells cease to release adequate amounts of therapeutic agent. Following retrieval, the retrieved system can be replaced by another system to maintain therapeutic agent delivery in the subject. A second or subsequently implanted system can be implanted in the same or a different location.

The implantable therapeutic delivery system delivery system described herein provides several advantages over other cell encapsulation techniques developed for the delivery of insulin secreting cells for the treatment of diabetes. The primary advantage is that cell dispersion in the hydrogel of the implantable system creates a short diffusion distance which affords fast glucose responsiveness. The short diffusion distance also enhances nutrient and oxygen delivery to the islet cells within the system thereby greatly improving long term islet cell survival and functionality.

The implantable therapeutic delivery system containing insulin producing and secreting cells (e.g., islet cells) is suitable for treating a subject having Type I (juvenile diabetes) or Type II diabetes. Suitable subjects include children, adults, and elderly subjects having an insulin deficiency.

In accordance with one embodiment, the implantable therapeutic delivery system containing insulin producing cells is implanted laparoscopically into the abdominal cavity or thoracic cavity. Utilization of the implantable system by a diabetic patient can substantially decrease the need to monitor blood sugar levels and may eliminate the need for insulin injections altogether. The implanted system may be monitored regularly (e.g., monthly or bi-monthly) to ensure the cells of the implant are functioning adequately.

In accordance with the aspect of the application directed to treatment of diabetes, the implantable therapeutic delivery system comprises insulin producing cells. Suitable insulin secreting cells include islet cells. Since the cells within the implantable system described herein are protected from the host immune system, the islet cells can be derived from any suitable source, i.e., human or non-human. Examples of suitable animal sources include, without limitation, primates, pigs, bovids, equids, felids, canids, and rodents. In one embodiment, the islet cells are stem or progenitor cells, including induced pluripotent stem cells that differentiate into insulin producing islet cells. Suitable insulin secreting cell populations and methods for producing such populations are known in the art, see, e.g., and without limitation, U.S. Pat. No. 8,425,928 to Martinson et al.; U.S. Pat. Nos. 5,773,255 and 5,712,159 to Fiore; U.S. Pat. No. 6,642,003 to Perfetti et al.; Rezania et al., "Reversal of Diabetes with Insulin-Producing Cells Derived In vitro from Human Pluripotent Stem Cells," *Nat. Biotech.* 32:1121-1133 (2014); Kuo et al., "Stem Cell Therapy: Differentiation Potential of Insulin Producing Cells from Human Adipose Derived Stem Cells and Umbilical Cord MSCs," *Int'l. J. Clin. Med.* 1(1):21-25 (2014); Thakkar et al., "Insulin-secreting Adipose-derived Mesenchymal Stromal Cells with Bone Marrow-derived Hematopoietic Stem Cells from Autologous and Allogenic Sources for Type I Diabetes Mellitus," *Cytotherapy* doi.org/10.1016/j.jcyt.2015.03.608 (pub. Online April 2015), which are hereby incorporated by reference in their entirety.

Further the implantable therapeutic delivery system can be used to treat condition associated with an insufficient level of insulin secretion. These are conditions where a subject produces a lower plasma level of insulin than is required to maintain normal glucose levels in the blood such that the subject with the condition associated with insufficient insulin secretion becomes hyperglycemic. In such a condition, the pancreatic beta cells of the afflicted subject secrete an insufficient level of insulin to maintain the presence of a normal concentration of glucose in the blood (i.e., normoglycemica).

One of the conditions associated with an insufficient level of insulin secretion is insulin resistance. Insulin resistance is a condition in which a subject's cells become less sensitive to the glucose-lowering effects of insulin. Insulin resistance in muscle and fat cells reduces glucose uptake (and, therefore, local storage of glucose as glycogen and triglycerides), whereas insulin resistance in liver cells results in reduced glycogen synthesis and storage and a failure to suppress glucose production and release into the blood. Insulin resistance normally refers to reduced glucose-lowering effects of insulin. However, other functions of insulin can also be affected. For example, insulin resistance in fat cells reduces the normal effects of insulin on lipids and results in reduced uptake of circulating lipids and increased hydrolysis of stored triglycerides. Increased mobilization of stored lipids in these cells elevates free fatty acids in the blood plasma. Elevated blood fatty-acid concentrations, reduced muscle glucose uptake, and increased liver glucose production all contribute to elevated blood glucose levels. If insulin resistance exists, more insulin needs to be secreted by the pancreas. If this compensatory increase does not occur, blood glucose concentrations increase and type II diabetes occurs.

A further condition associated with an insufficient level of insulin secretion is metabolic syndrome. Metabolic syndrome is generally used to define a constellation of abnormalities that is associated with increased risk for the development of type II diabetes and atherosclerotic vascular disease. Related conditions and symptoms include, but are not limited to, fasting hyperglycemia (diabetes mellitus type II or impaired fasting glucose, impaired glucose tolerance, or insulin resistance), high blood pressure; central obesity (also known as visceral, male-pattern or apple-shaped adiposity), meaning overweight with fat deposits mainly around the waist; decreased HDL cholesterol; and elevated triglycerides.

Other conditions that may be associated with an insufficient level of insulin secretion include, without limitation, hyperuricemia, fatty liver (especially in concurrent obesity) progressing to non-alcoholic fatty liver disease, polycystic ovarian syndrome (in women), and acanthosis nigricans.

Yet another aspect of the present application relates to a zwitterionic sulfobetaine-based nylon polymer of formula (II)

(II)

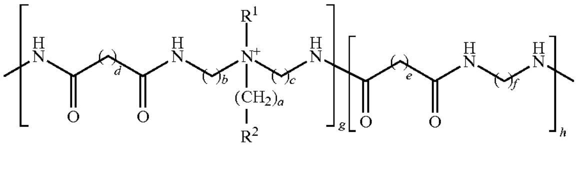

where $R^1$ is a $C_{1-10}$ alkyl;

$R^2$ is $SO_3^-$, $CO_2^-$, phosphate, or

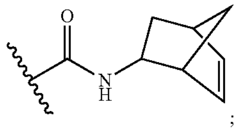 [SMILES: *C(=O)NC1CC2C=CC1C2 ; ";"]

;

a, b, c, d, e, and f are independently selected integers from 1 to 20;

g and h are integers from 1 to 10,000,000; and

indicates a point of attachment.

In one embodiment of the zwitterionic sulfobetaine-based nylon polymer, the nylon polymer has g to h in a molar ratio ranging from 0.01:0.99 to 0.99:0.01. The nylon polymer can have a number average molecular weight of 1000 to 1000000 grams per mole of polymer, and a glass transition point of −60° C. to 300° C.

A final aspect of the present application relates to a zwitterionic sulfobetaine-based polydimethylsiloxane polymer of formula (III)

(III)

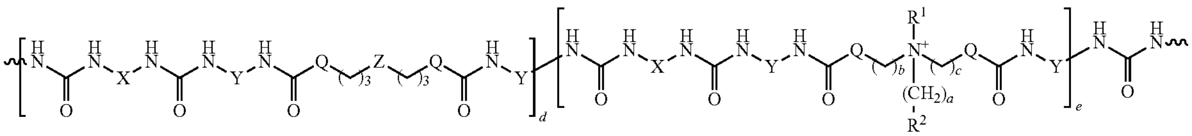

where

X and Y are independently selected from a substituted or unsubstituted $C_{1-20}$ alkylene;

Q is O or NH;

Z is a polydimethylsiloxane;

$R^1$ is H, or $C_{1-10}$ alkyl;

$R^2$ is $SO_3^-$, $CO_2^-$, or phosphate;

a, b, and c are independently selected integers from 1 to 20; and d and e are independently integers from 1 to 10,000,000.

In one embodiment of the zwitterionic sulfobetaine-based polydimethylsiloxane polymer, the polymer has d to e in a molar ratio ranging from 0.01:0.99 to 0.99:0.01. The polydimethylsiloxane based polymer can have a number average molecular weight of 1000 to 1000000 grams per mole of polymer, and a glass transition point of −60° C. to 300° C.

Preferences and options for a given aspect, feature, embodiment, or parameter of the technology described herein should, unless the context indicates otherwise, be regarded as having been disclosed in combination with any and all preferences and options for all other aspects, features, embodiments, and parameters of the technology.

The following Examples are presented to illustrate various aspects of the present application, but are not intended to limit the scope of the claimed application.

EXAMPLES

The examples below are intended to exemplify the practice of embodiments of the disclosure but are by no means intended to limit the scope thereof.

Materials and Methods

Materials/Reagents

Poly(tetramethylene ether)glycol (number-average molecular weight 2000, PTMG, Sigma-Aldrich) was dried in vacuum oven prior to synthesis. 1,4-Diaminobutane, stannous octoate ($Sn(Oct)_2$), anhydrous dimethyl sulfoxide (DMSO), dichloromethane, diethyl ether, and 1,1,1,3,3,3-Hexafluoro-2-propanol (HFIP) were obtained from Sigma-Aldrich. 1,6-Diisocyanatohexane (HDI), 1, 3-propanesultone and N-Butyldiethanolamine were purchased from the Alfa Aesar. Calcium chloride ($CaCl_2$) and barium chloride ($BaCl_2$) were purchased from EMD Millipore. Sterile sodium alginate (SLG100, 200-300 kDa MW) was purchased from FMC BioPolymer Co. (Philadelphia, PA). Rabbit anti-insulin antibodies (Cat. #ab63820) was purchased from Abcam, and anti-glucagon antibody (Cat. #SAB4200685) produced in mouse was purchased from Sigma-Aldrich. Alexa Fluor™ 594 donkey anti-rabbit antibody (Cat. #A-21207) and Alexa Fluor™ 488 goat anti-mouse antibody (Cat. #A-11001) were purchased from Invitrogen.

Animals 8 weeks-old immune-competent male C57BL/6 were purchased from The Jackson Laboratory and Sprague-Dawley rats were purchased from Charles River Laboratories (Wilmington, MA). All animal procedures were approved by the Cornell Institutional Animal Care and Use Committee Statistical Analysis Data are expressed as Mean±SEM in these experiments. Paired Student's t-test was used to compare two sets of quantitative data from macrophage activation studies, studies of FBR to various PU devices, and ex vivo GSIS experiments, with $P<0.05$ being considered as statistically significant.

Example 1—Synthesis of 3-(butylbis(2-hydroxyethyl)ammonio)propane-1-sulfonate (SB-Diol); 4-(bis(2-aminoethyl)(methyl)ammonio)butanoate (SB-Diamine); 3-((bis(2-hydroxyethyl)amino) methyl)-5,5-dimethylimidazolidine-2,4-dione (Halamine-diol); and tert-butyl 3-(bis(2-hydroxyethyl) amino)propanoate (THAP) Monomers SB-Diol Monomer N-Butyldiethanolamine (16.1 g, 0.1 mol), 1,3-propanesultone (13.4 g, 0.11 mmol) and dichloromethane (300 mL) were added into a 500 mL round-bottom flask. The mixture was stirred under nitrogen atmosphere for 24 h at 40° C. After reaction, the solvent was removed using a rotary evaporator. The product was precipitated by diethyl ether and then washed with diethyl ether three times to get white powder. The chemical structure of the product (SB-Diol) was confirmed by proton nuclear magnetic resonance. $^1H$ NMR ($D_2O$, 400 MHz, ppm): δ 3.97 (t, 4H), 3.54 (m, 6H), 3.4 (t, 2H), 2.91 (t, 2H), 2.15 (m, 2H), 1.68 (m, 2H), 1.34 (m, 2H), 0.90 (t, 3H).

SB-Diamine Monomer

Di-tert-butyl dicarbonate (50 g, 229 mmol) and triethylamine (38.3 mL, 275 mmol) were added dropwise over 0.5 h to a solution of N, N-Dimethylethylenediamine (6.71 g, 57.25 mmol) in anhydrous ethyl alcohol (150 mL) at 0° C. The mixture was stirred for 1 h at 0° C. and then for 18 h at 50° C. The solvent was removed using a rotary evaporator. The residue was dissolved in dichloromethane (150 mL), and the solution was washed successively with water. The organic layer was dried over anhydrous sodium sulfate and evaporated to get the product of N,N'-((methylazanediyl)bis(ethane-2,1-diyl))bis(2,2-dimethylpropanamide). $H^1$ NMR ($CDCl_3$, 400 MHz): δ 4.92 (s, 2H), 3.19 (t, 4H), 2.45 (t, 4H), 2.22 (s, 3H), 1.42 (s, 18H).

N,N'-((methylazanediyl)bis(ethane-2,1-diyl))bis(2,2-dimethylpropanamide (2.85 g, 10.0 mmol), 1,3-Propanesultone (2.45 g, 20.0 mmol) and anhydrous dichloromethane (30 mL) were added into a 150 mL round-bottom flask. The mixture was stirred under a nitrogen atmosphere for 48 h at 40° C. After the reaction, the solvent was removed using a rotary evaporator. The product was precipitated with anhydrous diethyl ether and washed with anhydrous diethyl ether to obtain a white powder. $H^1$ NMR ($D_2O$, 400 MHz): δ 3.39-3.65 (m, 10H), 3.15 (s, 3H), 2.94 (t, 2H), 2.21 (m, 2H), 1.40 (s, 18H)

Finally, 3.0 g of the obtained product was treated with a mixture of 12 mL trifluoroacetic acid (TFA) and 12 mL dichloromethane overnight at room temperature, concentrated with rotary evaporator, and precipitated in anhydrous diethyl ether to obtain a white powder (sulfobetaine-diamine monomer). $H^1$ NMR ($D_2O$, 400 MHz): δ 3.81 (m, 4H), 3.67 (m, 2H), 3.57 (m, 4H), 3.30 (s, 3H), 3.00 (t, 2H), 2.26 (s, 2H)

Halamine-Diol Monomer 5,5-dimethylhydantoin (13.21 g, 100 mmol), diethanolamine (10.6 g, 100 mmol), 8.1 g (100 mmol) of a 37% formaldehyde solution, and 100 mL methanol were added into a 250 mL round-bottom flask. The mixture was stirred for 4 h at room temperature. The solvent was removed from the reaction mixture using a rotary evaporator. The viscous residue produced was then dissolved in ethyl acetate, and anhydrous sodium sulfate was added for further drying purposes. After the removal of the sodium sulfate, the resulting solution was stored in the freezer. After 12 h, the white solid product, which precipitated from the ethyl acetate solution, was obtained after filtration using cold solution. The structure of the halamine-diol monomer was confirmed by $H^1$ NMR (DMSO-$d_6$, 400 MHz). The peaks were: δ 8.27 (s, 1H), 4.37 (t, 2H), 4.30 (s, 2H), 3.42 (m, 4H), 2.64 (t, 2H), 1.28 (s, 6H).

THAP Monomer

THAP was synthesized using a Michael-type reaction. Diethanolamine (10.5 g, 0.1 mol) was added into tert-butyl acrylate (12.8 g, 0.1 mol), and the reaction solution was stirred under a nitrogen atmosphere overnight at 35° C. and kept away from the light during the reaction. The resulting solution was removed thereby removing any unreacted material using a rotary evaporator, and then the product was purified by flash chromatography using dichloromethane and methanol (4:1) to yield THAP as a colorless oil with an 87% yield. $H^1$ NMR (400 MHz, $CDCl_3$, ppm): 3.55 (t, 4H), 3.17 (s, 2H), 2.75 (t, 2H), 2.58 (m, 4H), 2.35 (t, 2H), 1.40 (s, 9H)

Example 2—Synthesis of Zwitterionic Polyurethanes (ZPU) and Zwitterionic Nylons (ZN)

Scheme 1. Reaction route of Zwitterionic Polyurethanes

Zwitterionic Polyurethanes

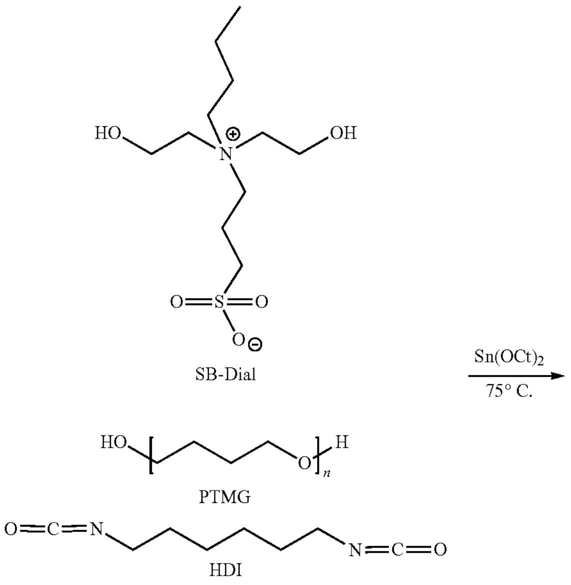

SB-Dial

PTMG

HDI

-continued

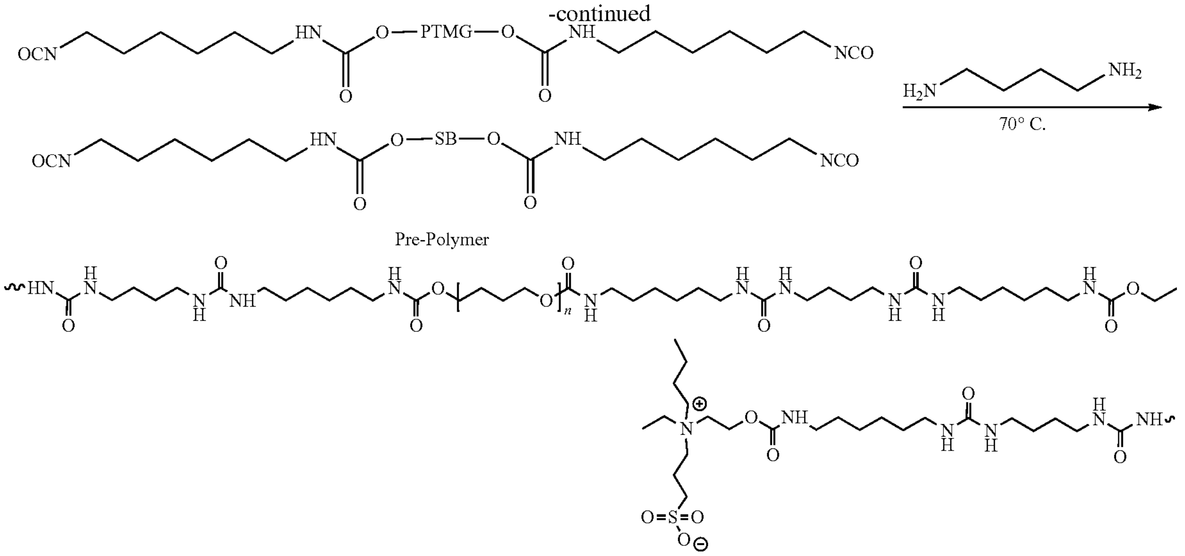

The synthetic route of ZPU is shown in Scheme 1. In this study, SB-Diol/PTMG were blended at various molar ratios, 0:1, 1:1, 2:1, and 3:1 (forming PU, ZPU-1, ZPU-2, ZPU-3, respectively), and were dissolved in DMSO solvent at 80° C. under nitrogen atmosphere. HDI was then added into the flask dropwise, following two droplets of $Sn(Oct)_2$ catalyst. The mixture was stirred vigorously at 80° C. for 1 hour. DMSO was added if the viscosity of reaction solution increased significantly. 1,4-Diaminobutane, which acts as a chain extender, was added into the solution dropwise and stirred for overnight at 80° C. under nitrogen protection. The molar ratio of (SB-Diol+PTMG):HDI:1,4-Diaminobutane was set as 1:2:1. After the reaction, the polymer solution was precipitated in diethyl ether, and then washed with diethyl ether three times. The resulting white powder was then washed with DI water three times and placed in vacuum oven at 70° C. for 24 h to remove the residual solvent. To prepare ZPU polymer films, the ZPU powders were each dissolved in HFIP at 50° C., followed by casting into poly(tetrafluoroethylene) dishes and putting into a vacuum oven at 60° C. for 1 day.

Scheme 2. Reaction route of carboxybetaine-based nylon

Zwitterionic Nylons

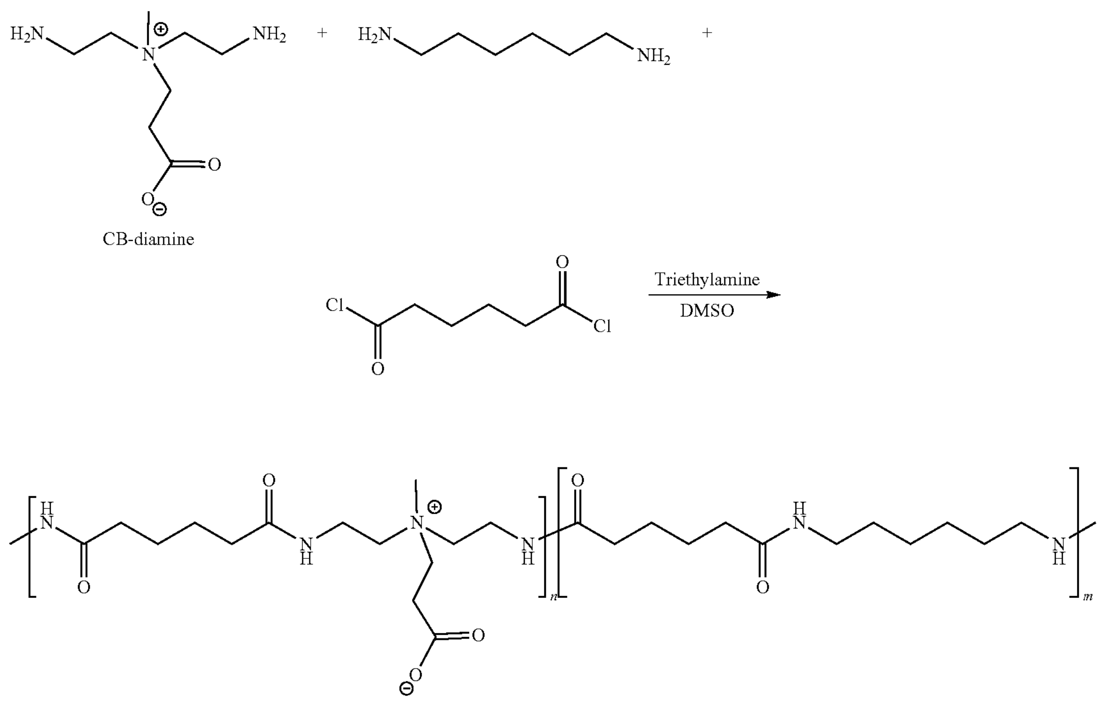

An exemplary synthetic route for the formation of the ZNs is shown in Scheme 2. SB-diamine and Hexamethylenediamine were blended at various molar ratios and then were dissolved in anhydrous DMSO at 0° C. in a 500 mL three-neck flask with nitrogen filled. Anhydrous triethylamine was then added into the solution. Adipoyl chloride was added dropwise into the mixture over 30 min. The mixture was stirred for 1 h at 0° C. and then for 18 h at 50° C. The polymer was then precipitated in diethyl ether and wash with diethyl ether several times. The resulting polymer was washed with water several times and dried in a vacuum oven. The (SB-diamine+Hexamethylenediamine):trimethylamine:adipoyl chloride molar ratio was set at 1:2:1.

Exemplary synthetic schemes of the polydimethylsiloxane based zwitterionic polymers can be seen in FIGS. 1A-1D. These polymers have polydimethylsiloxane in the backbone and are formed from the reaction of diols and diamines with diisocyanates. Diisocyanates are reacted with diamines and diol with tin catalysts to form precursor monomers. The monomers are then reacted together with a diamine to form the polymers, which are then treated with acid to form the zwitterionic moiety.

Example 3—Fabrication of ZPU Device by Electrospinning

The ZPU polymers were first dissolved in HFIP solvent with sufficient stirring at room temperature. The polymer solution was loaded in a 10-mL plastic syringe (BD Biosciences) and was fed at 1.2 mL/h by a syringe pump (Harvard Apparatus, U.S.). The nanofibers were spun at 15 kV with a 22 G blunt needle as the spinneret. The distance between the needle tip and the collector was set to 12 cm. The rotating aluminum rods (McMaster-Carr) with different dimensions were placed in the path of the polymer solution jet and were used to collect the electrospun fibers. The rod was rotated at a speed of 400-450 rpm. After 40 min of electrospinning, the nanofibrous tubes with rods were soaked in a DI water bath overnight. The tubes were then removed from the rods carefully, and were dried in vacuum oven at 40° C. for 1 day. The ends of the tubes were thermally sealed using a hand impulse sealer (Impulse Sealer Supply, CA). The tubes were finally placed into 70% ethanol solution and sterilized using UV light for future use.

Example 4—ZPU Device Characterizations

A scanning electron microscope (SEM) (LEO 1550 FESEM) was used to observe the morphology of ZPU nanofibrous tubes. ImageJ software was used to analyze and quantify the fiber diameter. Tensile tests of ZPU nanofibrous tubes were performed on a TA instruments DMA Q800 Dynamic Mechanical Thermal Analysis (DMTA). All the samples were mounted between the holders at a distance of ~2 cm. The samples were stretched until failure at a rate of 5 mm/min. To verify the polymer chemical structure, ZPU nanofibrous tubes were analyzed by FT-IR (Fourier-transform infrared spectroscopy, Bruker Vertex V80V vacuum FT-IR system). The wavenumber ranges from 400 to 4000 $cm^{-1}$ with 64 scans. The XPS analysis was made on a Scienta Omicron ESCA-2SR with operating pressure ca. $1\times10^{-9}$ mBar. A hemispherical analyzer determined electron kinetic energy, using a pass energy of 200 eV for wide/survey scans and 50 eV for high resolution scans. The binding energy (BE) scale was corrected using $C_{1s}$ as a reference at BE of 284.6 eV. The elemental compositions were determined based on peak areas from the $C_{1s}$, $N_{1s}$, $O_{1s}$ and $S_{2p}$ peaks by CasaXPS software. The water absorption of the ZPU nanofibrous tubes was tested using a gravimetric method. The ZPU nanofibrous tubes were dried and weighed to obtain the dry weight ($m_{dry}$). The tubes were immersed into a 0.9% saline solution and weighed to obtain the wet weight ($m_{wet}$). The water adsorption was calculated as $(m_{wet}-m_{dry})/m_{dry}\times100\%$.

Example 5—Protein Adsorption Assay

The protein adsorption on ZPU film was evaluated using a fluorescence method. Briefly, ZPU films were cut into small disks (6 mm in diameter and 1 mm thick) with a biopsy punch. The above disks were placed into FITC-labeled fibrinogen solution (0.1 mg/mL in PBS) at room temperature for 1 hour. After this period, the films were gently washed three times with PBS buffer to remove loosely adsorbed proteins. Fluorescence images of ZPU film surfaces were taken using a fluorescence microscope with 10× lens at a fixed exposure time. ImageJ software was used to analyze and quantify the fluorescence intensity of each sample.

Example 6—Cell Adhesion Assay

NIH/3T3 cells were kept in a humidified incubator with 5% $CO_2$ at 37° C. prior to use. The cell culture medium consisted of Dulbecco's modified Eagle medium (DMEM), 10% fetal bovine serum (FBS), and 2% penicillin streptomycin. The nanofibrous ZPU membranes (6 mm×6 mm) were washed with sterile PBS three times and placed into individual wells of a 12-well plate. 2 ml of cell suspensions at $10^5$ cells/mi were added to each well and incubated with the samples for 3 days. After incubation, the membranes were washed by PBS gently and transferred to a new 12-well plate. The LIVE/DEAD assay kit was added into each well and incubated for 30 min. The fluorescent images were finally acquired using an EVOS AMF4300 imaging system.

Example 7—Cytokine Secretion

Murine Bone Marrow Derived Macrophages (BMDM) used for the assay of cytokine secretion were harvested from the femurs or tibia of 6-8 week-old C57BL/6J mice (Jackson Laboratories). Cells were treated with ACK lysis buffer (Invitrogen), centrifuged, and resuspended in culture media consisting of Dulbecco's modified Eagle medium (DMEM), 10% FBS, 1% Penstrep, and 15% macrophage colony stimulating factor (MCSF) for macrophage differentiation. After culture for one week, BMDM were dissociated using a cell scraper, and seeded on the tissue culture plates at a density of 10' cells/well in culture media. The cells were allowed to attach for 6 hours at which point the media was changed and IFNy (20 ng/mL)/LPS (25 ng/mL) was added along with the samples. The samples were incubated for 12 h and the supernatants were collected and analyzed for TNF-α secretion by enzyme-linked immunosorbent assay (ELISA) following the manufacturer's instructions (Thermofisher).

Example 8—Rat Islets Isolation and Purification

Male Sprague-Dawley rats from Charles River Laboratories were used as pancreatic islet donors. Briefly, rat bile duct was cannulated, and the pancreas was distended by an injection of cold 0.15% Liberase (Research Grade, Roche) in RPMI 1640 media solution. The pancreas was digested in a 37° C. water bath for 30 min. Islets were purified using a discontinuous Histopaque 1077 (Sigma) gradient density and collected from interphase. These islets were further purified by a series of six gravity sedimentations. Finally, purified islets were handpicked under the microscope and washed with a sterile saline solution. The islets were then cultured overnight in RPMI 1640 media with 10% heat-inactivated fetal bovine serum (HIFBS) and 1% penicillin/streptomycin for further use.

Example 9—Islet Encapsulation

Prior to islet encapsulation, sterile ZPU tubes (diameter: 1.0 mm; length: 2.5 cm) were prepared. One end of the device was thermally sealed by hand impulse sealer (Impulse Sealer Supply, CA). The cultured islets were centrifuged at 562 RCF for 1 min and washed with 0.9% saline solution. After washing, about 250 IEQ islets were resuspended in a 2% SLG100 alginate solution. The alginate solution containing islets was loaded into the device and placed into a crosslinking buffer containing 100 mM $CaCl_2$ and 5 mM $BaCl_2$ for 10 min. After crosslinking, the device with encapsulated islets were washed 5 times with 0.9% saline solution to remove residual crosslinking buffer. The other end of the device was thermally sealed prior to implantation.

Example 10—Transplantation and Retrieval of Device

Immune-competent male C57BL/6 mice were used for implantation. Diabetic mice were created by injecting a streptozotocin (130 mg/kg body weight) solution (13 mg/mL in 5 mM sodium citrate buffer solution) interperitoneally. The mice whose non-fasted blood glucose levels were above 300 mg/dL with two consecutive measurements were considered diabetic. The mice were anesthetized using 3% isoflurane in oxygen and maintained at the same rate throughout the procedure. After abdomen fur shaving and disinfection, a 1 mm incision was made along the midline of the abdomen and the peritoneal lining was exposed using blunt dissection. The peritoneal wall was then grasped with forceps, and a 1-mm incision was made using a scalpel. Two devices with 500-600 IEQ islets in total were implanted into the peritoneal cavity through the incision. The incision was closed by surgical suture. The same procedure was followed for empty device implantation.

The engrafted mice were kept alive after the devices were retrieved for a predetermined time. The BG level was monitored after retrieval in order to further confirm the function of implanted devices. The retrieved device was fixed in 10% neutrally buffered formalin for staining if there are no other characterizations such as ex vivo GSIS assay or imaging.

Example 11—Blood Glucose Monitoring

A small droplet of blood was collected using a lancet from tail vein and glucose concentration was measured with a commercial glucometer (Contour Next EZ Blood Glucose Meter). Mice with non-fasting BG levels below 200 mg/dL were considered normoglycemic.

Example 12—Intraperitoneal Glucose Tolerance Test (IPGTT) Assay

An IPGTT assay was conducted 2 or 3 months after transplantation. Mice with ZPU devices were fasted for approximately 16 h before an intraperitoneal injection of glucose solution (2 g/kg weight). BG levels were measured at the desired time points.

Example 13—In Vitro and Ex Vivo Glucose Stimulated Insulin Secretion

Krebs Ringer Bicarbonate (KRB) buffer (98.5 mM NaCl, 4.9 mM KCl, 2.6 mM $CaCl_2$), 1.2 mM $MgSO_4.7H_2O$, 1.2 mM $KH_2PO_4$ and 25.9 mM $NaHCO_3$ supplemented with 20 mM HEPES and 0.1% BSA (Serological)) was prepared first. For the in vitro glucose stimulated insulin secretion (GSIS) study, islet-containing ZPU devices and the same number of naked islets were cultured for 1 h in KRB buffer at 37° C., 5% $CO_2$, and then incubated for 1 h with 2.8 mM or 16.7 mM D-glucose under the same condition. The supernatants were collected and stored for future analysis. For ex vivo GSIS study, retrieved islet-containing ZPU devices were placed into KRB buffer supplemented with 2.8 mM D-glucose for 30 min and incubated in KRB buffer solution supplemented with 2.8 mM or 16.7 mM D-glucose for 1 h. The supernatants were collected and stored for future analysis. Insulin content was quantified using mouse/rat insulin ELISA kit (ALPCO) following the manufacturer's instructions. Absorbance of reaction solution at 450 nm was measured in the Synergy plate reader (Biotek). The stimulation index (SI) was obtained as the ratio of the insulin content after high glucose (16.7 mM) stimulation divided by insulin content after low glucose (2.8 mM) solution.

Example 14—Insulin Content in the Pancreas

To measure the total insulin content in the pancreas of the diabetic mice, healthy mice, and engrafted mice, homogenized pancrease tissue was placed into acid-ethanol (1.5% HCl in 70% ethanol), cut into small pieces using scissors, digested overnight at −20° C., centrifuged and neutralized with pH 7.5 Tris buffer. The supernatants were collected and stored at −80° C. for insulin content determination as described above.

Example 15—Histological Analysis and Immunostaining

The retrieved devices were fixed in 4% paraformaldehyde, embedded in paraffin and then sectioned by Cornell Histology Core Facility. The samples were sliced on a microtome at a thickness of 5 μm. Paraffin sections were then stained with hematoxylin/eosin. To conduct immunofluorescence staining, the histological slides were deparaffinized followed by sequential washing in xylene, ethanol and water. These slides were then boiled in EDTA solution for antigen exposure. Non-specific binding was blocked with 10% goat serum for 45 min at room temperature. These slides were decanted and incubated with primary rabbit anti-insulin antibodies (1:200) and primary mouse anti-glucagon antibodies (1:200) overnight at 4° C. The sections were washed and incubated with the FITC-conjugated secondary antibodies, Alexa Fluor 594 donkey anti-rabbit antibody (1:400 dilution) and Alexa Fluor 488 goat anti-mouse antibody (1:400 dilution), for 30 min at room temperature. Nuclei were labeled with DAPI, and fluorescence images were captured using an EVOS AMF4300 imaging system.

Results

Synthesis, Fabrication, and Characterization of Nanofibrous ZPU Devices

ZPU polymers (exemplary structure showing in FIG. 2A) were synthesized from sulfobetaine-diol (SB-Diol), poly (tetramethylene ether) glycol (PTMG), hexamethylene diisocyanate (HDI), and 1,4-Diaminobutane. SB-Diol acts as a hard segment, and was synthesized and introduced to improve the hydrophilicity, antifouling properties, and biocompatibility of the ZPU polymers. Non-biodegradable PTMG with a molecular weight of 2 KDa acts as a soft segment, and was selected since the long soft segment can improve the mechanical strength of ZPU. HDI as a chemical building block was used to synthesize the ZPU polymers. 1,4-Diaminobutane as a chain extender was used to adjust the molecular weight of the ZPU polymers. A family of ZPU polymers with various SB contents as a part of polymer backbone were synthesized via a facile two-step polymerization as illustrated in Scheme 1. The synthesized zwitterionic polyurethanes were termed as $ZPU_x$, where x represents the molar ratios of SB-Diol:PTMG. The synthesized polyurethane without SB content as control was denoted as PU.

Figure 2D:
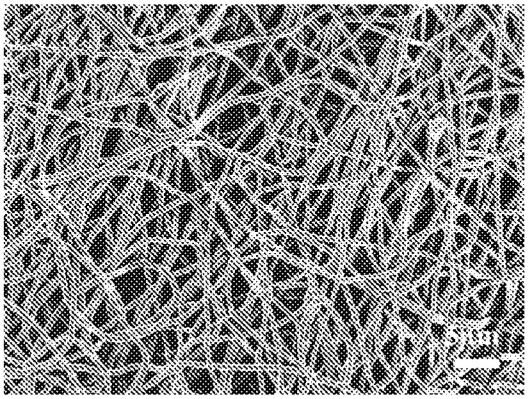

To fabricate the ZPU device, ZPU polymers were electrospun onto the rotating aluminum rods to obtain the nanofibrous tubular conduit. The size of the nanofiber could be finely tuned by adjusting the concentration of ZPU polymer, while the wall thickness of nanofibrous tube could be controlled by the deposition time. ZPU devices with different dimensions (Inner diameter: 1~5 mm; wall thickness: 100~200 μm) were fabricated and shown in the FIGS. 2B and 2C. The end of the ZPU device can be simply sealed by a thermal sealer. SEM image shows that the electrospun ZPU membrane possessed a nanoporous structure with randomly oriented nonwoven fibers (FIG. 2D), with an average diameter of ~280 nm.

Figure 2E:
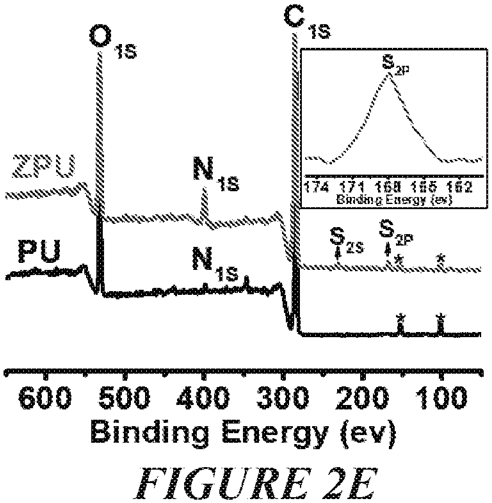
Figure 2F:
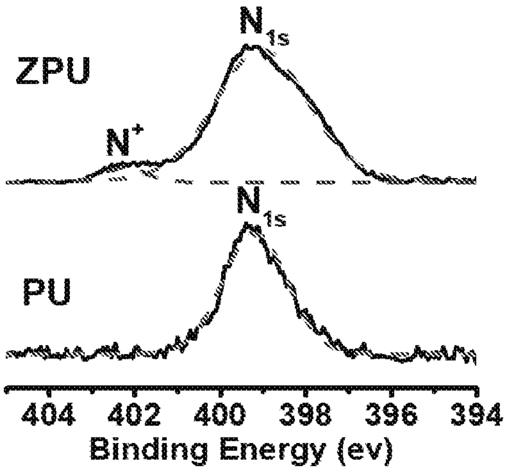
Figure 2G:
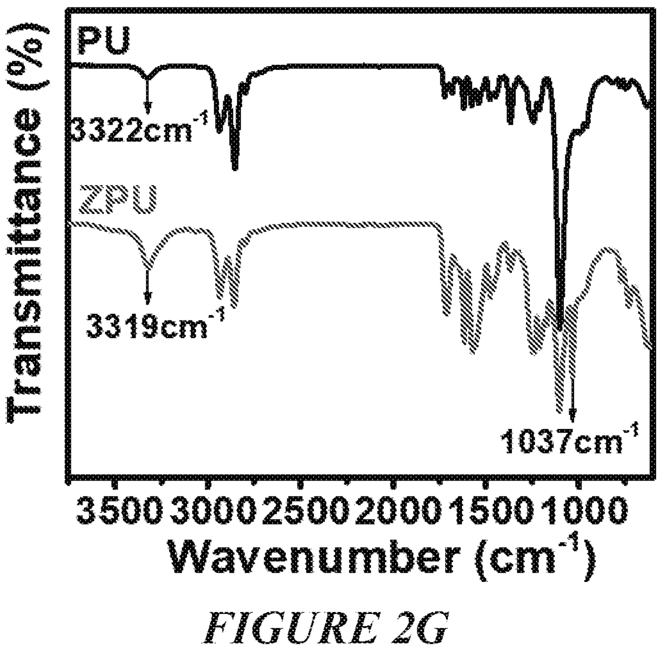
Figure 2H:
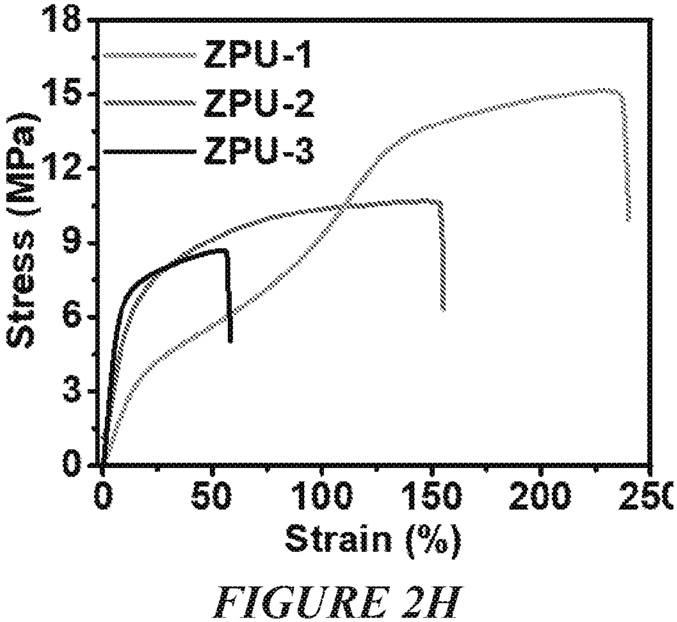

To evaluate the bulk properties of the ZPU devices, XPS analysis was used to determine the elemental compositions and SB moiety. Two peaks centered at 230 eV (binding energy, $S_{2S}$) and 168 eV (binding energy, $S_{2p}$) were detected in ZPU-2 but not in PU, which is indicative of the sulfur atom from the SB group (FIG. 2E). Furthermore, the PU and ZPU-2 polymers are clearly distinguished based on their $N_{1S}$ spectrum (FIG. 2F). The $Na_{1s}$ spectrum for the ZPU-2 consists of two peaks, 402 eV from sulfobetaine's quaternary amine and 399 eV from urethane nitrogen, while only one peak (399 eV) was detected for PU. This finding confirmed that zwitterionic polyurethane containing SB groups was successfully synthesized. FT-IR results (FIG. 2G) showed that the peak appearing at 1037 $cm^{-1}$ for ZPU-2 was attributed to the presence of $SO_3^-$. This signature peak is another convincing evidence of existence of SB group. The mechanical properties of ZPU device were investigated through tensile test. It was found that tensile strength and break strain of ZPU (FIG. 2H) decreased with increasing SB content. ZPU-1 device with low SB content was elastic while ZPU-3 device with high SB content became brittle. The ZPU-2 device with a medium SB content was shown to be mechanically robust with a breaking strain of >1.5 and tensile stress of >10 MPa.

Figure 2I:
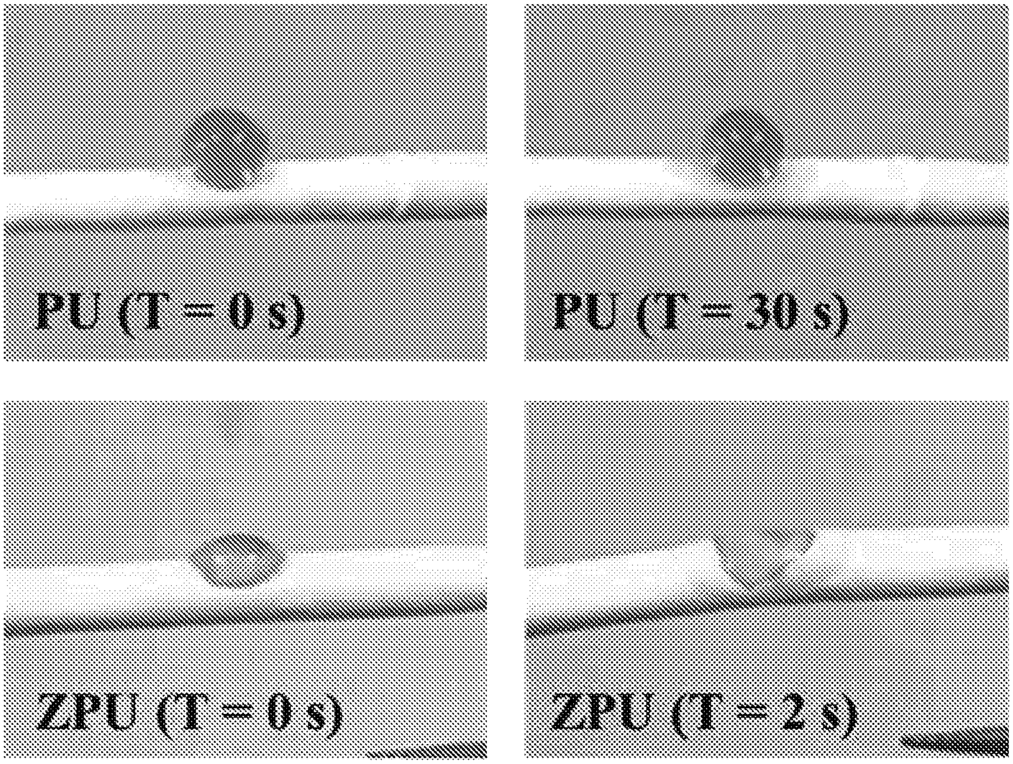

Current encapsulation devices made of PTFE, PCL, and PU are hydrophobic. These devices tend to have a negative impact on mass transfer and induce severe biofouling and FBR. Surface modifications may be applied to enhance the surface wettability and biocompatibility, but limitations remain. For example, the modifications only occurs in a small depth away from the surface, and the induced properties post modification can degrade over time (Liu et al., "Ultralow Fouling Polyacrylamide on Gold Surfaces Via Surface-initiated Atom Transfer Radical Polymerization," *Biomacromolecules* 13(4):1086-1092 (2012), which is hereby incorporated by reference in its entirety). Herein, the hydrophilicity of the ZPU devices were regulated by tuning the SB content. A water drop test was used to evaluate the mass transfer of devices. The surface of PU device that did not contain any SB group was shown to be hydrophobic. The whole water droplet retained on the nanoporous surface after 30 seconds even with capillarity-driven wicking phenomenon (FIG. 2I). In comparison, water droplets immediately wetted the ZPU-2 surface and was adsorbed by the device. The result indicated that ZPU device had superior mass delivery relative to PU device.

Figure 2J:
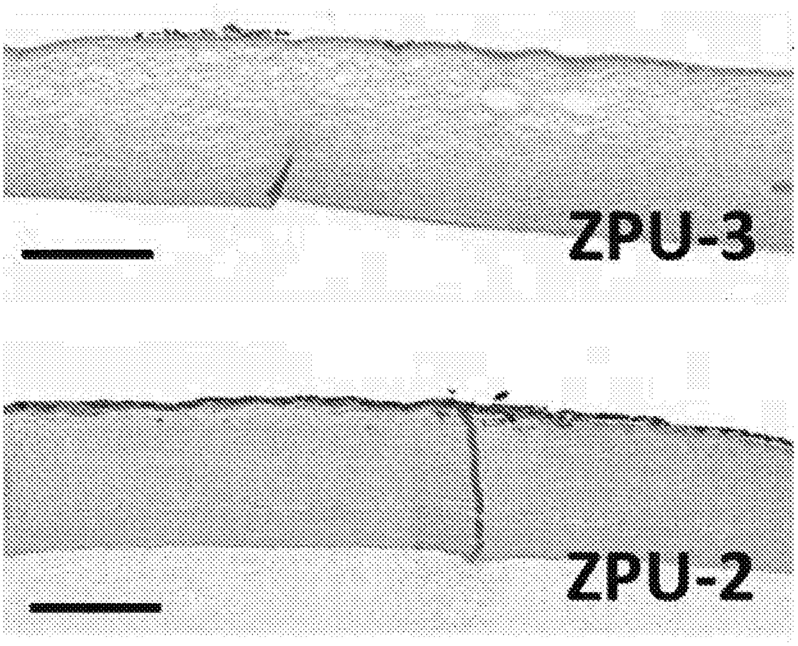

To apply ZPU nanoporous membranes as a cell encapsulation device, the membranes need to be stable (i.e., remain integral) in the aqueous environment. Histological studies (FIG. 2J) revealed that the nanofibers of ZPU-3 device became fluffy while ZPU-2 device could remain integral, 1 month post intraperitoneal implantation in C57BL/6J mice. The fiber interaction for ZPU-3 polymer may be significantly attenuated especially in the aqueous environment if the SB content is too high. A delicate balance was struck between stability and hydrophilicity. Taken together, ZPU-2 device, due to its balanced hydrophilicity, mechanical robustness, and stability under in vivo conditions, was selected as a cell encapsulation device.

In Vitro Characterization of ZPU Devices

Figure 3A:
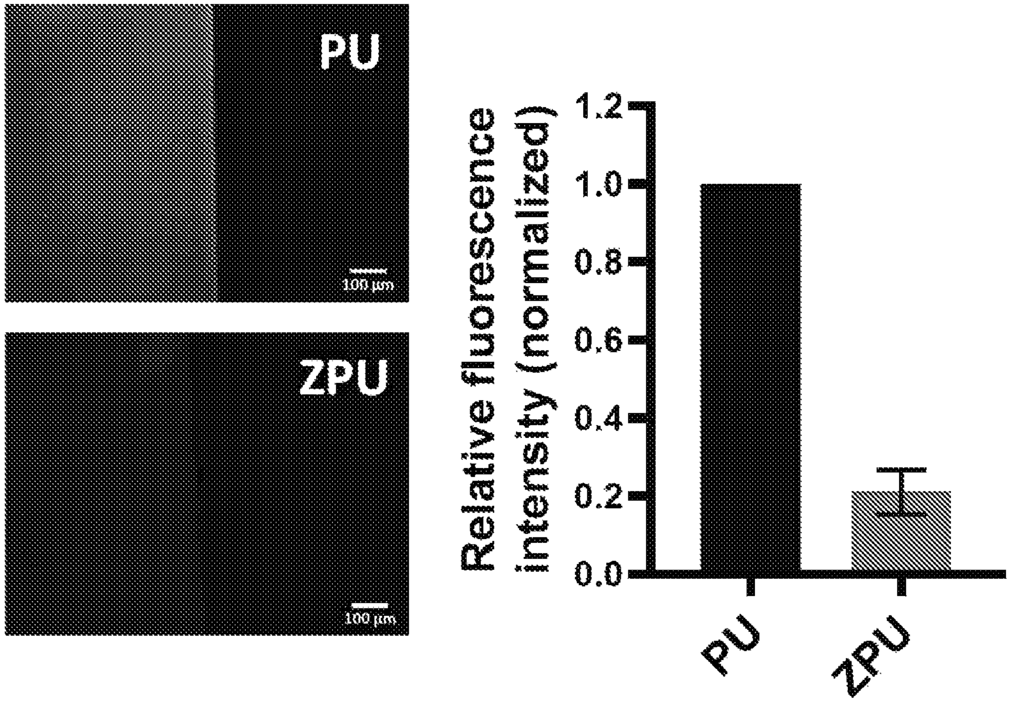
FIGS. 3A-3D show the in vitro characterizations of the ZPU device.
Figure 3B:
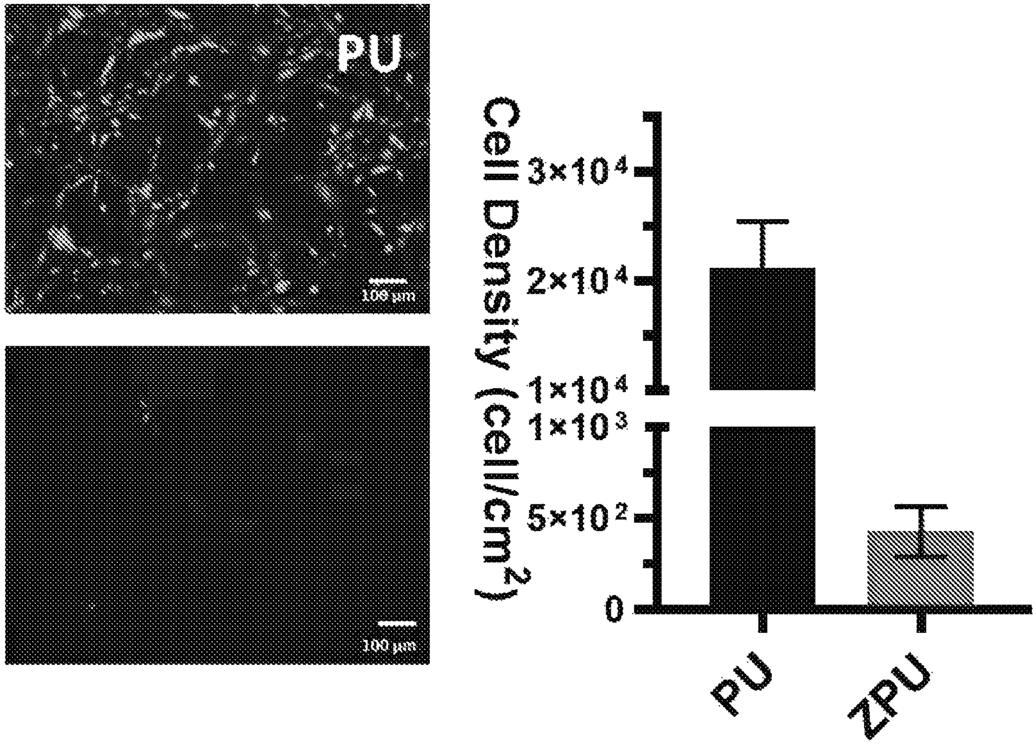

Protein adsorption on the surface of medical device is considered the initial and critical step in the foreign body response. Fibrinogen (Fg) was used as the model protein to assess the antifouling performance of the ZPU device, with the PU device as a control. Fg is a coagulation protein involved in platelet aggregation and blot clot formation (Jansen et al., "Zwitterionic PEG-PC Hydrogels Modulate the Foreign Body Response in a Modulus-dependent Manner," *Biomacromolecules* 19(7):2880-2888 (2018), which is hereby incorporated by reference in its entirety). Relative to the PU device, the amount of Fg adsorptions on ZPU device is 21.1% (FIG. 3A). Clearly, the ZPU surface was highly resistant to non-specific protein adsorption. Next, the cell attachment on the ZPU device in vitro was investigated. After incubation at 37° C. for 3 days, NIH/3T3 cells quickly attached, proliferated, and formed a confluent layer on the control PU device surfaces while there were only scattered cells observed on the ZPU devices (FIG. 3B). The cell densities on PU and ZPU surfaces were $2.1\times10^4$ cells/$mm^2$ and $4.3\times10^2$ cells/$cm^2$, respectively. These results indicate that ZPU device could reduce cell adhesion.

Figure 3C:
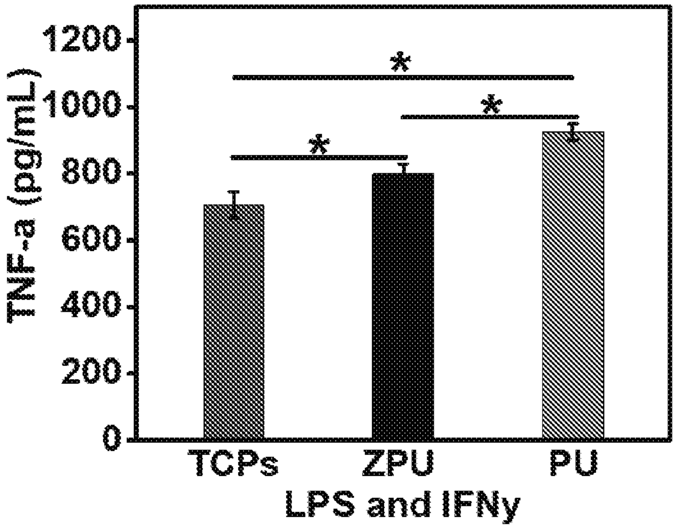

Macrophage activation on the ZPU device was studied by seeding murine bone marrow derived macrophages (BMDM) and examining the release of tumor necrosis factor-α (TNF-α) associated with pro-inflammatory macrophages (An et al., "Developing Robust, Hydrogel-based, Nanofiber-enabled Encapsulation Devices (NEEDs) for Cell Therapies," *Biomaterials* 37:40-48 (2015), which is hereby incorporated by reference in its entirety). The BMDMs cultured on the ZPU device secreted lower levels of TNF-α when compared to those cultured on the PU device (FIG. 3C). This study demonstrated that incorporating a zwitterionic moiety (SB) into polyurethane can attenuate the inflammatory activation of macrophages in vitro.

Figure 3D:
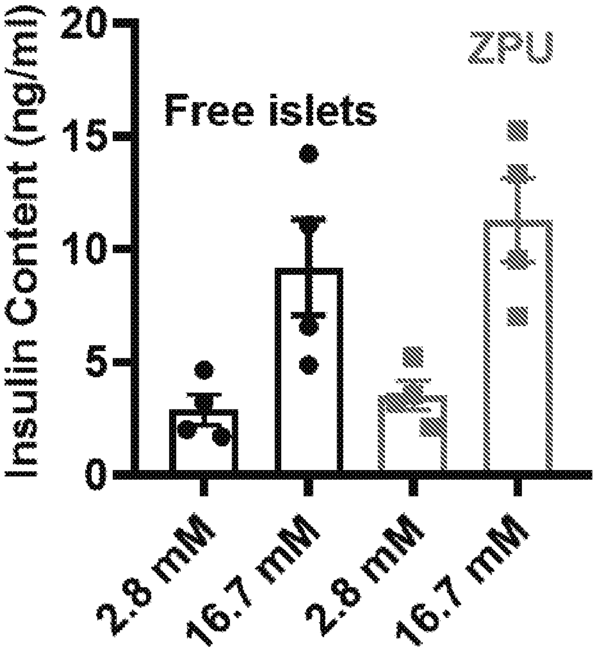

To study mass transfer of ZPU device, a static glucose stimulated insulin secretion (GSIS) experiment was conducted. FIG. 3D showed that the ZPU devices were responsive to glucose change and secreted insulin. Furthermore, the stimulation index (a ratio of the insulin value following high glucose stimulation divided by insulin value following low glucose stimulation) of islets encapsulated into the ZPU device (3.21±0.38) was not statistically different from that of free islets (3.17±0.25). Although the ZPU membrane was relatively thick (about 200 μm), the mass diffusion was not compromised. This is in good agreement with the previous hydrophilic test. The result further confirmed that the hydrophilic ZPU device can provide superior mass transfer.

Evaluation of ZPU Device Safety

Figure 4A:
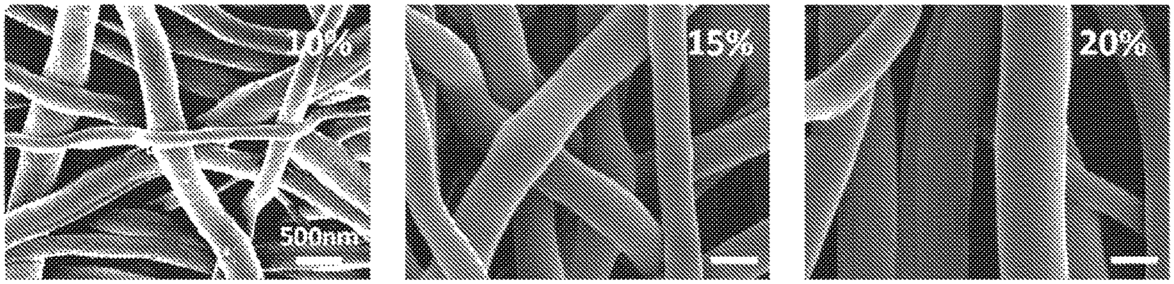
FIGS. 4A-4D show the evaluation of cell penetration for ZPU devices.

The safety of an encapsulation device is of paramount importance for clinical applications especially when human embryonic stem cell (hESC)-derived insulin-producing cells are used. The device needs to create a durable physical barrier to exclude immune cells and mediators that are harmful to encapsulated cells and also to prevent the encapsulated cells from escaping the device. Therefore, an encapsulation device that could prevent cell penetration and escape will be critical for long-term application in clinical settings. The fiber size which is correlated with pore size, was finely tuned to prevent cell penetration or escape. As shown in FIG. 4A, the dimension of ZPU fiber was readily tuned by the concentration of polymer solution. The size of ZPU fiber was increased with increasing polymer concentration.

Figure 4B:
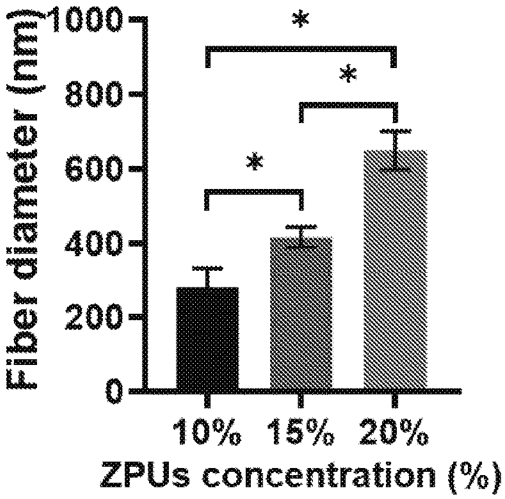
Figure 4C:
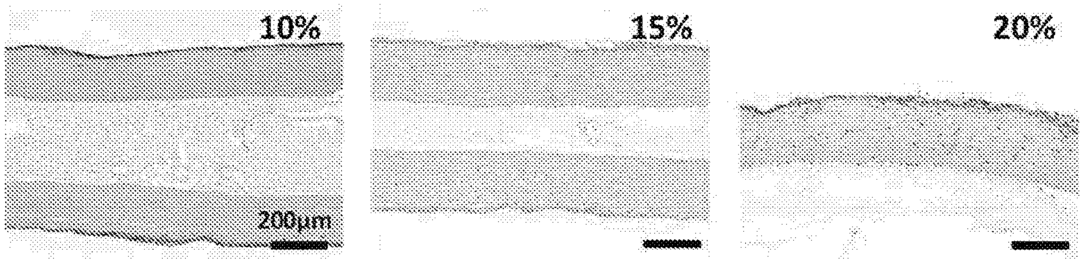
Figure 4D:
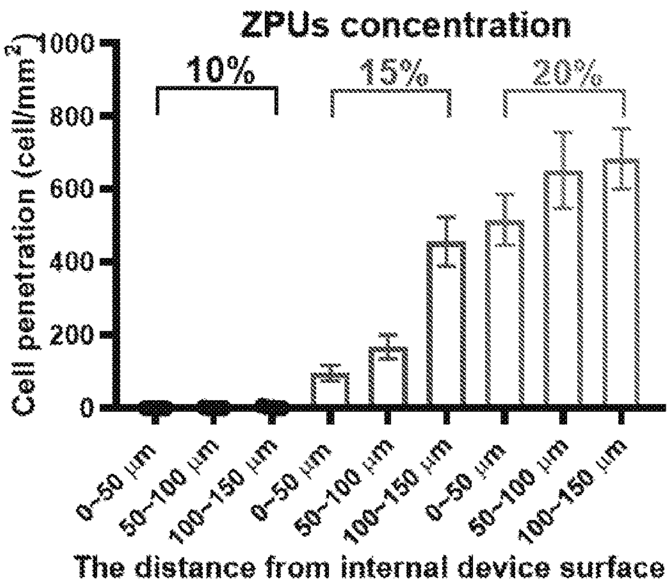

To validate whether ZPU device can provide a physical immune protection barrier, three kinds of ZPU devices with different fiber size (FIG. 4A) was implanted into the intraperitoneal space of C57BL/6J mice for 1 month. The ZPU device with an average fiber diameter of 280 nm completely excluded cell penetration (FIGS. 4B and 4C). Nearly all the cells were blocked by outermost layer. For the other two devices with an average fiber diameter of 417 and 649 nm, respectively, a different number of cells (FIG. 4D) penetrated into the device and some even migrated into the interior for the device with largest fiber size. The above result indicates that ZPU device could be engineered to prevent cell entrance and escape.

In Vivo Biocompatibility of ZPU Devices

Figure 5A:
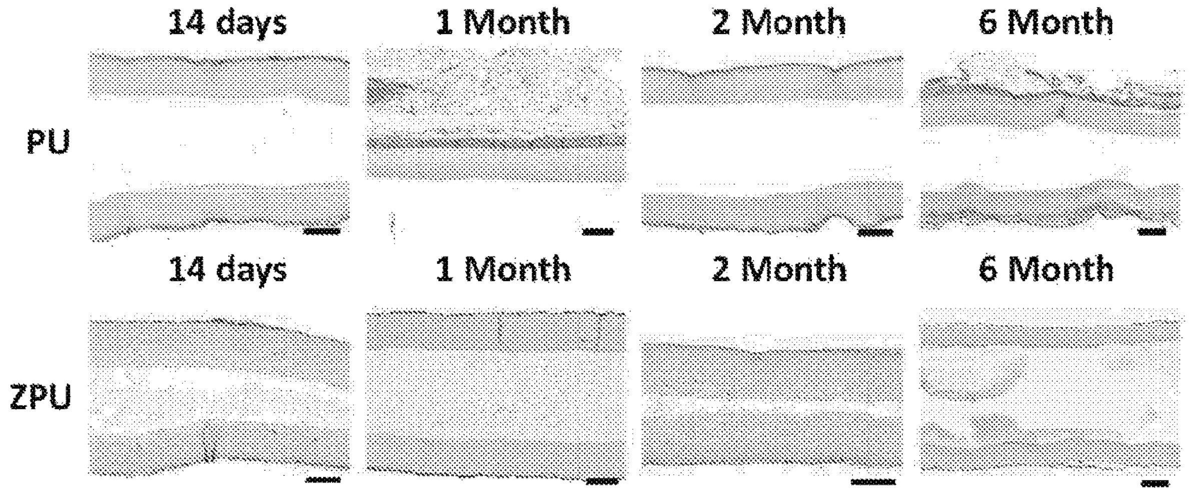
FIGS. 5A-B show that the ZPU devices mitigate cellular overgrowth in mice.
Figure 5B:
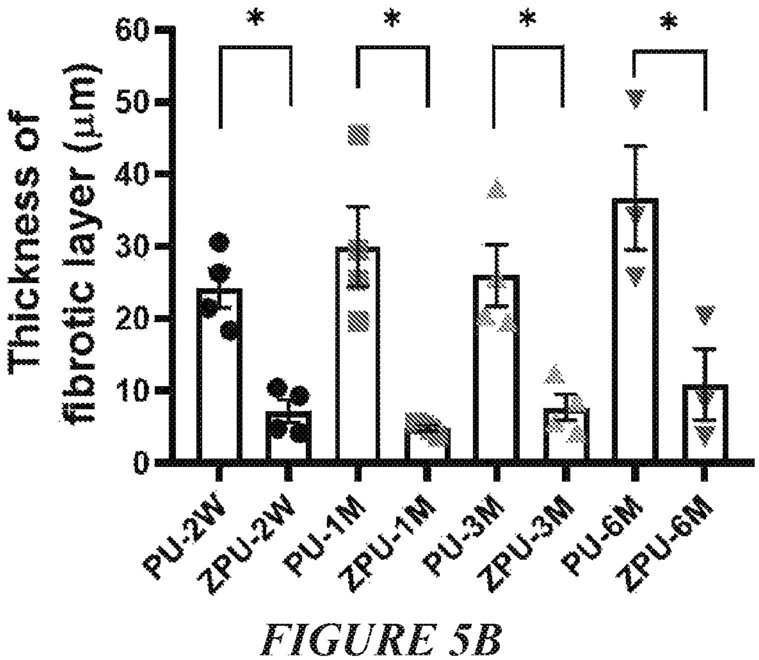

The performance of implanted devices is often impeded by the foreign-body response (FBR). Therefore, there is a critical need for development of a novel medical device with low FBR. Immunocompetent C57BL6J mice were chosen because this strain was shown to elicit a strong FBR against foreign implants (Veiseh et al., "Size- and Shape-dependent Foreign Body Immune Response to Materials Implanted in Rodents and Non-human Primates," *Nature Materials* 14(6): 643-651 (2015), which is hereby incorporated by reference in its entirety). The FBR to the blank ZPU devices was evaluated at selected time points post implantation (2 weeks, 1 month, 3 months, and 6 months). The PU device was chosen as a positive control for comparison. At 14 days, it was observed that the ZPU device had a very thin cellular overgrowth around them (7.2±1.6 μm), while the PU device induced a much thicker cellular overgrowth (24.2±2.7 μm) (FIG. 5A). The result suggests that the ZPU devices with SB moiety could mitigate the cellular growth effectively. Thick cellular overgrowth around device is generally thought to have a negative impact on mass transfer. Encouraged by the short-term results, longer term studies were further conducted (i.e. 1, 3, and 6 months). Similar and consistent results were obtained: the cellular overgrowth on ZPU device was significantly thinner as compared to the case of PU control (FIG. 5A). The thickness of cellular overgrowth on ZPU device at 1, 3, and 6 months was 4.9±0.4, 7.7±1.8, and 9.8±4.0 μm, respectively, which are about 28.9, 16.3, 29.6, and 26.7% of that deposited on the PU surface (FIG. 5B), respectively. These quantifications suggest that ZPU device substantially reduced cellular overgrowth in the intraperitoneal space of C57BL/6J mice in both short (14 d) and long terms (180 d). Furthermore, all the ZPU devices (n=15) implanted were easily retrieved without tissue adhesion, while 4 of 15 PU devices had tissue adhesion, making the retrieval difficult.

Diabetes Correction in Mice

Figure 6A:
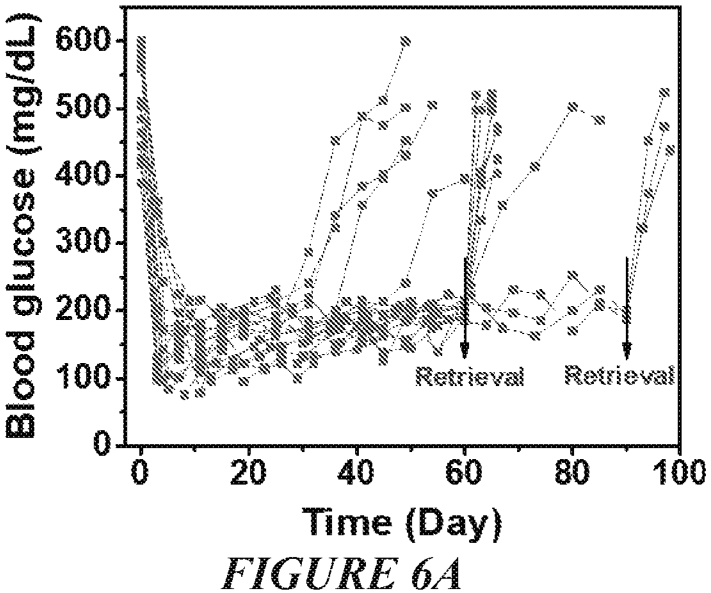
FIGS. 6A-6L show the therapeutic potential of the ZPU device using rat islets.
Figure 6B:
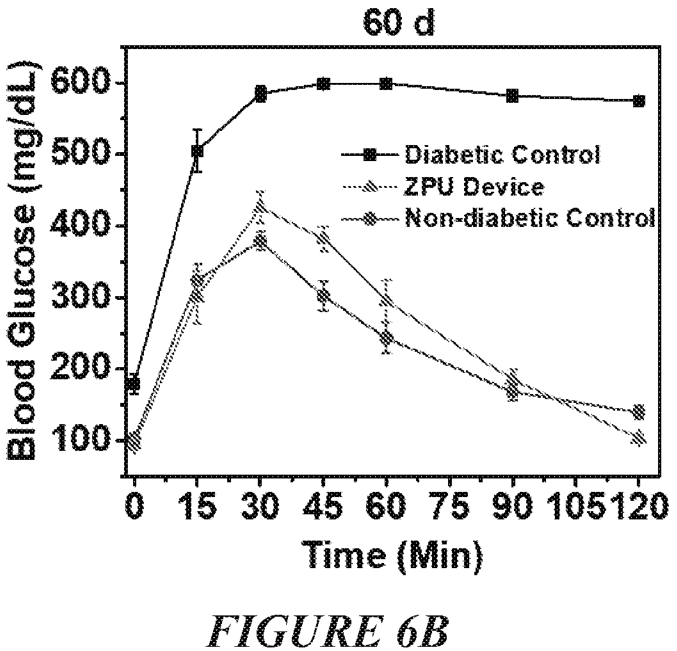
Figure 6C:
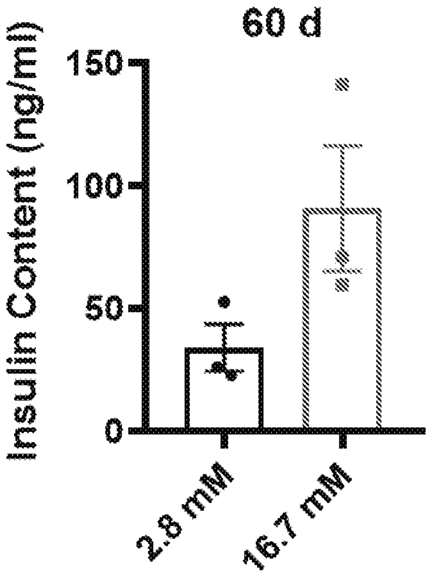
Figure 6D:
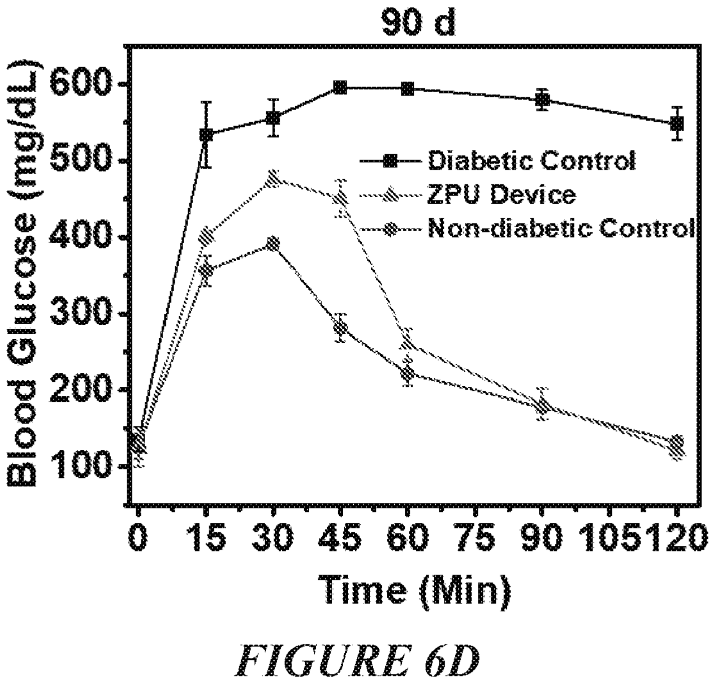
Figure 6E:
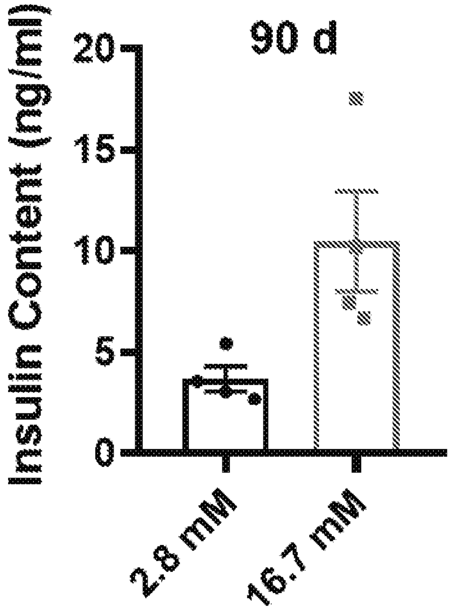

After confirming the mechanical, mass transfer and antifouling properties as well as safety and biocompatibility of the ZPU device, its therapeutic potential as a cell encapsulation platform for treatment of T1D was explored. Rat islets were firstly mixed into alginate solution. The islet-loaded alginate solution was then injected into the device and then crosslinked using a mixture of calcium and barium ions. After sealing the open end, ZPU devices encapsulating rat islets (500-600 islet equivalents per mouse) were transplanted into the peritoneal cavity of streptozotocin (STZ)-induced diabetic C57BL/6J mice and evaluated for their ability to restore normoglycemia. FIG. 6A showed the blood glucose concentrations (BG) over time post-transplantation. The BG levels of all engrafted mice dropped to normal glycemic range (BG<200 mg/dL) within one week after transplantation. 8 out of 13 mice remained normoglycemic for 2 months until the devices were retrieved. The BG level of the cured mice went up after retrieval, confirming the device function. Furthermore, the devices were readily retrieved and there was no tissue adhesion. An intraperitoneal glucose tolerance test (IPGTT) (FIG. 6B) was performed 2 months after transplantation. The engrafted mice gradually achieved normoglycemia within 90 min, further confirming the function of transplanted islets. However, the BG of the diabetic mice failed to drop to a normal range even after 120 min. A glucose-stimulated insulin secretion (GSIS) test of the retrieved ZPU devices (FIG. 6C) suggested that the islets were responsive to glucose change and secreted insulin, further evidence for normal islet function. In another set of 3-months transplantation experiments, 3 out of 4 mice were cured until retrieval. IPGTT and GSIS (FIGS. 6D and 6E) assays were conducted again to verify the viability and normal function of transplanted islets. Pancreatic insulin content of the engrafted, diabetic, and healthy mice was also measured. The content of pancreatic insulin for the engrafted and diabetic mice is only 1% of that of healthy mice. This result indicated that the ZPU device containing islets delivered the vast majority of insulin to control the blood glucose levels.

Figure 6F:
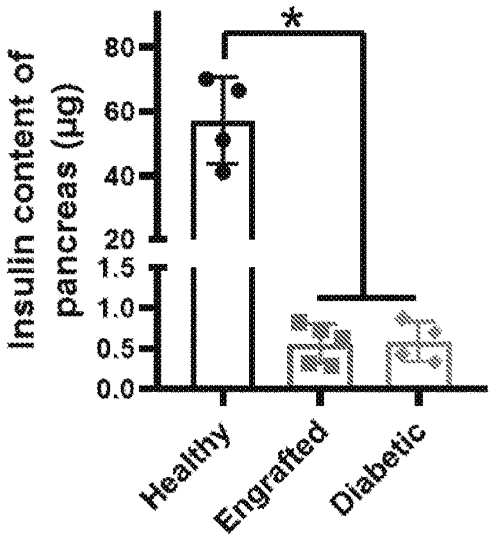
Figure 6G:
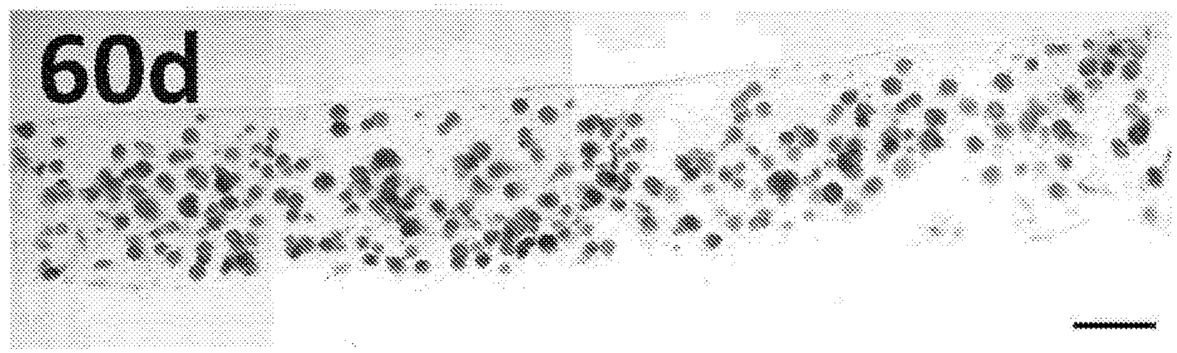
Figure 6H:
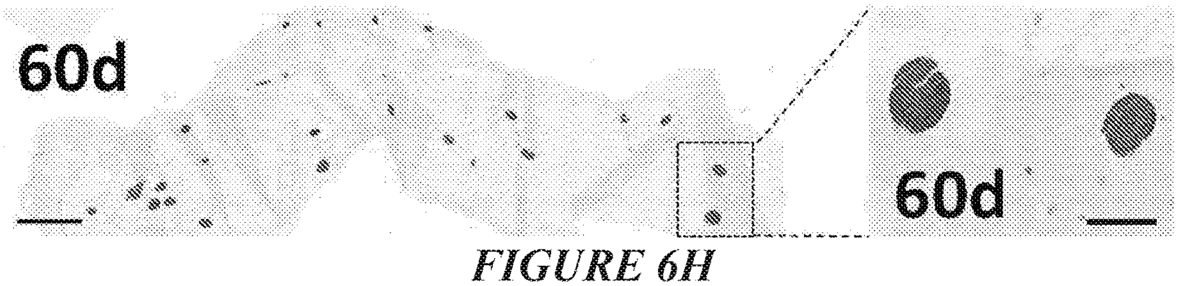
Figure 6I:
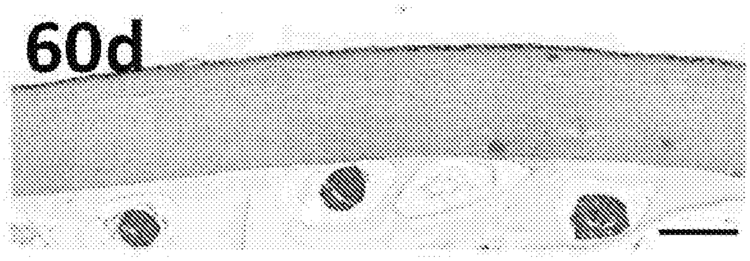
Figure 6J:
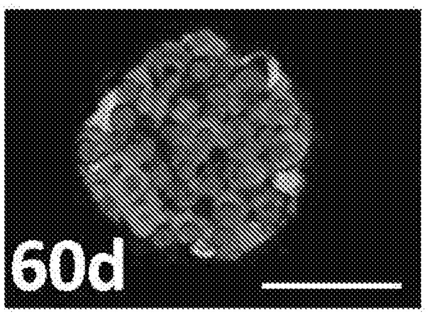
Figure 6K:
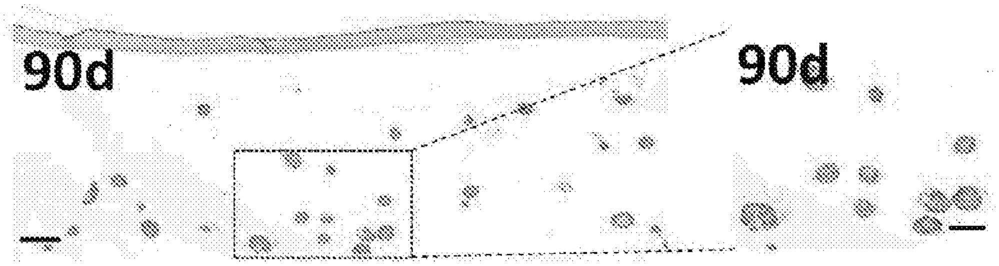
Figure 6L:
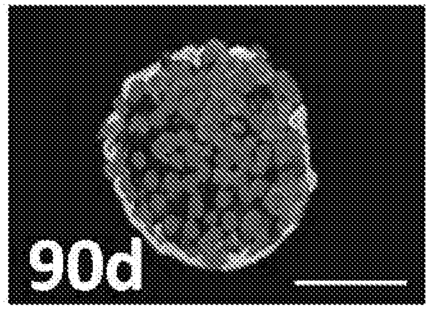

Post-retrieval characterizations also showed that there were numerous healthy rat islets in islet-loaded alginate hydrogel after the nanofibrous membrane of retrieved device was peeled off carefully (FIG. 6F). Many retrieved islets exhibited morphology as healthy as intact islets before transplantation, as shown by the H&E staining of cross-sections (FIG. 6G). Although FBR was slightly elevated by encapsulated cells or xenogeneic donor tissue, the histological analysis (FIG. 6H) confirmed that there was thin cellular deposition as low as ~8.9±1.3 μm around ZPU devices. The viability and normal function of transplanted islets were further verified by positive insulin staining (FIG. 6I). Furthermore, the devices were easily retrieved and there was no tissue adhesion. Lastly, there was no cell entrance and escape from the device as verified by histological analysis (FIG. 6J). For the 3-month transplantation experiment, histological analysis and positive insulin staining (FIGS. 6K and 6L) confirmed the long-term function of the device. Some mice with early failure of correcting hyperglycemia might be attributed to unintentional variables such as the disintegration of cell-loaded alginate, device defects and islet number or intrinsic biological variations. Taken together, the data described above provide a proof of concept for the use of ZPU device for T1D treatment

DISCUSSION

Although cell encapsulation represents one of the promising approaches for T1D treatment, clinical use remains challenging, partially because of the lack of an appropriate device that meets several requirements simultaneously for islet encapsulation. For example, hydrogel-based devices tend to have poor mechanical properties. Some porous membranes such as PTFE or polyurethane easily induced severe FBR and had mass diffusion constraints. The zwitterionic polyurethane polymers with adjustable hydrophilicity were synthesized and ZPU-2 was identified as a polymer with desired characteristics. A nanofibrous encapsulation device made of the ZPU-2 polymer was designed and fabricated. This is the first time to apply zwitterionic polyurethane as a cell encapsulation device. The optimized ZPU device possessed hydrophilicity in combination with mechanical robustness. Additionally, the ZPU device exhibited superior mass transfer as evidenced in rapid absorption of water droplets and in vitro GSIS tests. The mechanical robustness and superior mass transfer property of the ZPU device meet two criteria for islet encapsulation.

Moreover, it is desirable for medical devices to have antifouling properties in the context of complex biological media (e.g., body fluid, blood, and cell lysate). A serious problem especial for nanoporous device is the fouling by attached proteins and cells, which can result in pore block and negative impact on mass transfer. The nanofibrous ZPU device was shown to be highly resistant to protein adsorption and cell attachment. An appropriate encapsulate device is required to not only address immune rejection but also long-term safety especially when human embryonic stem cell (hESC)-derived cells are used. The ZPU device with proper nanofiber size (<281 nm) was mechanically durable and completely excluded cell penetration into device while allowing sufficient mass transfer necessary for transplanted cells. In the meantime, all the encapsulated cells were contained by the device and could not escape from it. The safety of ZPU device is another important advantage for islet encapsulation.

Another key criterion of encapsulation device was the ability to mitigate the fibrotic response. The biocompatibility of current devices is still unsatisfactory for islet encapsulation. Hydrogel coating was commonly used to improve the biocompatibility of medical devices. However, the hydrogel coating was prone to swelling and even fracturing under in vivo conditions, impairing the device function (An et al., "Developing Robust, Hydrogel-based, Nanofiber-enabled Encapsulation Devices (NEEDs) for Cell Therapies," *Biomaterials* 37:40-48 (2015), which is hereby incorporated by reference in its entirety). It was surprisingly found that the ZPU device without any hydrogel coating could mitigate the cellular overgrowth, to as low as 10 μm for up to 6 months while conventional PU device induced much thicker cellular overgrowth. The data, consistent with previous work (Liu et al., "Zwitterionically Modified Alginates Mitigate Cellular Overgrowth for Cell Encapsulation," *Nature Communications* 10(1):1-14 (2019), which is hereby incorporated by reference in its entirety), supported that zwitterionic groups due to their strong hydration, play an important role in material biocompatibility. This zwitterionic modification that mitigates cellular deposition can be applied to completely different materials. The excellent biocompatibility and ease of fabrication made the ZPU device desirable for islet encapsulation. To demonstrate the potential application of this ZPU device, rat islets were encapsulated to restore euglycemia up to ~3 months in diabetic mice.

Encapsulation and transplantation of insulin-producing cells represents a promising therapy for Type 1 diabetes (T1D). However, an encapsulation device that is both safe (i.e. no cell escape/penetration and no breakage) and functional (i.e. low foreign body response and high mass diffusion) remains a challenge. To address this challenge, a family of zwitterionic polyurethanes (ZPU) with sulfobetaine (SB) in the PU backbone were synthesized and used to fabricate encapsulation devices with tunable nanoporous structures via electrospinning. Compared to the conventional polyurethane (PU), the ZPU device exhibited similarly robust mechanical properties, but was much more hydrophilic and fouling-resistant and induced lower foreign body response (FBR) or cellular overgrowth upon intraperitoneal implantation in C57BL/6 mice for up to 6 months. A ZPU device with nanofiber size ~280 nm prevented cell penetration and enabled diabetes correction in mice for up to ~3 months. The ZPU device with its low FBR zwitterionic chemistry and highly porous but durable nanofibrous structure provide a promising candidate for developing a safe and functional cell encapsulation device for type 1 diabetes and other diseases.

A family of non-biodegradable and mechanically robust zwitterionic polyurethane with various SB contents as part of the PU backbone were designed and synthesized. The ZPU polymer was processed by electrospinning to obtain a nanofibrous device for islet encapsulation. Its hydrophilicity, mechanical robustness, superior mass transfer as well as excellent antifouling properties were demonstrated. The fiber size of ZPU device could be readily tuned to prevent cell entrance and escape. More importantly, ZPU device was shown to mitigate cellular overgrowth effectively upon implantation compared to the conventional PU device. The use of ZPU device for cell encapsulation in T1D treatment has been demonstrated. The ZPU device may contribute to a cell replacement therapy for T1D and other hormone deficient diseases.

Although preferred embodiments have been depicted and described in detail herein, it will be apparent to those skilled in the relevant art that various modifications, additions, substitutions, and the like can be made without departing from the spirit of the present application and these are therefore considered to be within the scope of the present application as defined in the claims which follow.

What is claimed is:

1. A fiber having a diameter of 1 nm to 10,000 nm, of one or more biocompatible polymers, wherein the one or more biocompatible polymers comprise a polymer of the formula

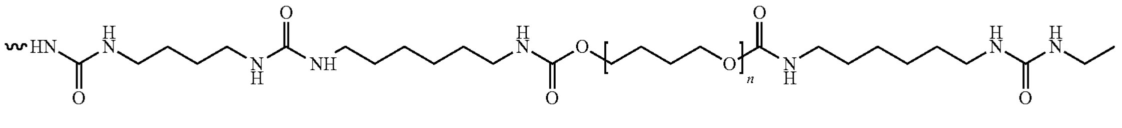

-continued

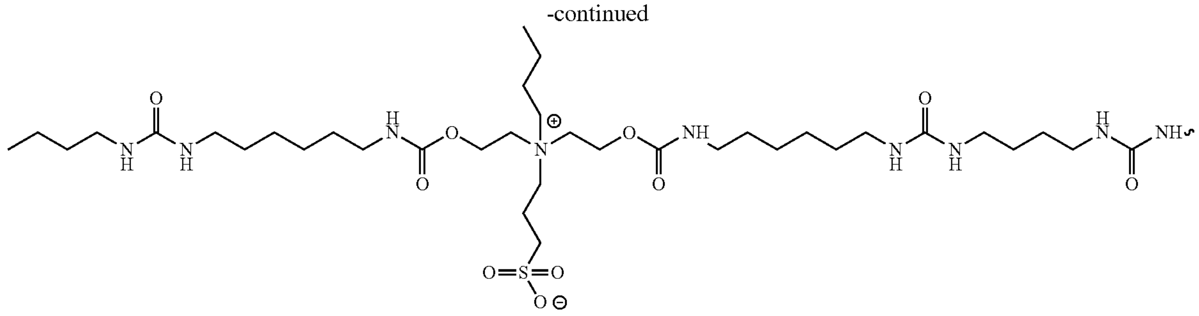

wherein n is an independently selected integer from 1 to 20.

2. An implantable therapeutic delivery system comprising:

a housing defining a chamber, wherein said housing is porous and formed from fibers of one or more biocompatible polymers, said fibers having a diameter of 1 nm to 10,000 nm, and the one or more biocompatible polymers comprising a polymer of the formula

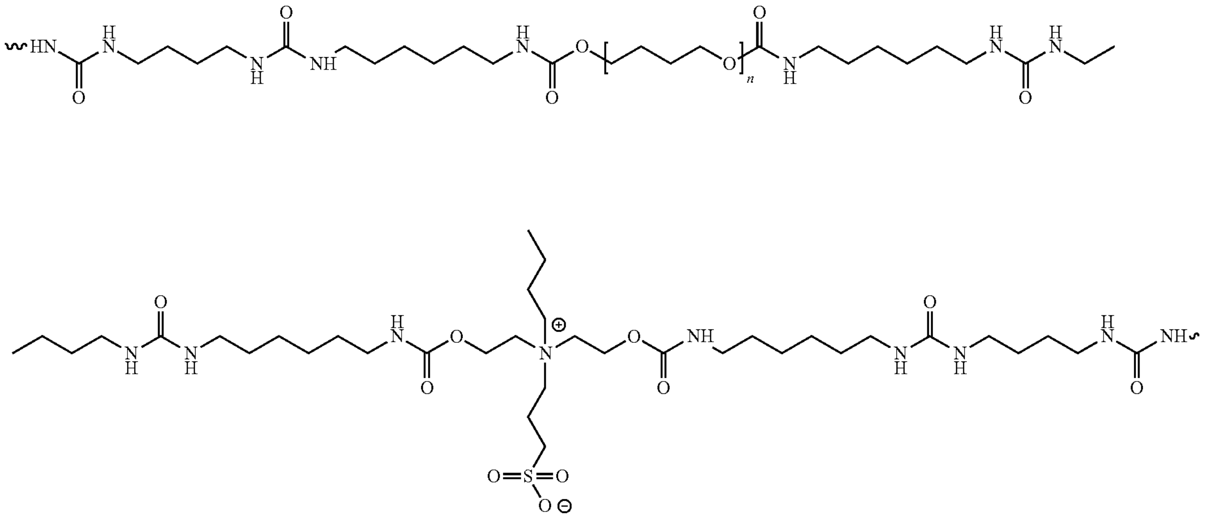

wherein n is an independently selected integer from 1 to 20.

3. The implantable therapeutic delivery system of claim 2, wherein the housing is an elongate hollow porous tube extending between first and second ends with the fibers being wound around the chamber.

4. The implantable therapeutic delivery system of claim 3, wherein the elongate hollow porous tube has a sealed first end.

5. The implantable therapeutic delivery system of claim 3, wherein the chamber of elongate hollow porous tube contains a hydrogel.

6. The implantable therapeutic delivery system of claim 5, wherein the hydrogel comprises alginate.

7. The implantable therapeutic delivery system of claim 5, wherein the hydrogel and elongate hollow porous tube are crosslinked.

8. The implantable therapeutic delivery system of claim 5, wherein the elongate hollow porous tube is sealed at the first and second ends so that the chamber is closed.

9. The implantable therapeutic delivery system of claim 8 further comprising:

a preparation of cells within the closed chamber which release a therapeutic agent from the chamber through the elongate hollow porous tube.

10. The implantable therapeutic delivery system of claim 9, wherein the cells are islet cells.

11. The implantable therapeutic delivery system of claim 9, wherein the cells are stem cells.

12. The implantable therapeutic delivery system of claim 3, wherein the elongate hollow porous tube has pores of a diameter of 10 nm to 1 mm.

13. The implantable therapeutic delivery system of claim 3, wherein the chamber of the elongate hollow porous tube has a diameter of 0.1 mm to 10 cm.

14. The implantable therapeutic delivery system of claim 3, wherein the elongate hollow porous tube has a wall thickness of 10 μm to 1 cm.

15. The implantable therapeutic delivery system of claim 3, wherein the elongate hollow porous tube has a length of 1 cm to 10 m.

* * * * *